US005422090A

United States Patent [19]

Stephens et al.

[11] Patent Number: 5,422,090
[45] Date of Patent: Jun. 6, 1995

[54] HUMAN PAI-2

[75] Inventors: Ross W. Stephens, Oslo, Norway; Jeffrey P. Golder, Mona Vale; Toni M. Antalis, Toowong, both of Australia; Thomas M. Barnes, Boston, Mass.; Michell A. Clark, Crows Nest, Australia; Peter L. Devine, Helensvale, Australia; Neil H. Goss; Philip R. Lehrbach, both of Wahroonga, Australia

[73] Assignees: Biotechnology Australia, Pty., Ltd., New South Wales; Australian National University, Acton, both of Australia

[21] Appl. No.: 911,531

[22] Filed: Jul. 15, 1992

Related U.S. Application Data

[60] Continuation-in-part of Ser. No. 765,495, Sep. 26, 1991, abandoned, and Ser. No. 693,542, Apr. 30, 1991, abandoned, which is a division of Ser. No. 25,815, Mar. 13, 1987, abandoned, said Ser. No. 765,495, is a continuation of Ser. No. 860,336, Jun. 13, 1986, abandoned.

[30] Foreign Application Priority Data

Aug. 13, 1984 [AU] Australia .............................. PG6531
Mar. 13, 1986 [AU] Australia .............................. PH5017
May 22, 1986 [AU] Australia .............................. PH6033
Sep. 18, 1986 [AU] Australia .............................. PH8100
Nov. 21, 1986 [AU] Australia .............................. PH9104

[51] Int. Cl.$^6$ .............................................. C07K 13/00
[52] U.S. Cl. .................................... 424/1.69; 530/350; 530/380; 530/381; 514/12
[58] Field of Search ..................... 530/350, 380, 381; 424/85.91, 1.1, 1.69; 514/12

[56] References Cited

U.S. PATENT DOCUMENTS

| | | | |
|---|---|---|---|
| 4,632,981 | 12/1986 | Bock ................................. | 530/393 |
| 4,711,848 | 12/1987 | Insley et al. ...................... | 435/91 |
| 4,849,349 | 7/1989 | Ragg et al. ....................... | 435/68.1 |
| 4,923,807 | 5/1990 | Webb et al. ...................... | 435/69.1 |
| 4,952,512 | 8/1990 | Loskutoff ......................... | 435/320.1 |
| 5,028,534 | 7/1991 | Sadler et al. ..................... | 435/69.1 |

FOREIGN PATENT DOCUMENTS

86/01212 2/1986 WIPO .

OTHER PUBLICATIONS

Aoki et al., "Inhibition of Plasminogen Activators by Naturally Occurring Inhibitors in Man", *American Journal on Physiology*, 1334–1447 (Dec. 1974).

Astedt et al., "Different Inhibition of One and Two Chain Tissue Plasminogen Activator by a Placental Inhibitor . . . ", *Scand. J. Clin. Lab. Invest.* 45: 429–435 (1985).

Astedt et al., "Purification of a Specific Placental Plasminogen Activator Inhibitor by Monoclonal Antibody (List continued on next page.)

Primary Examiner—Richard A. Schwartz
Assistant Examiner—Gary L. Brown
Attorney, Agent, or Firm—Foley & Lardner

[57] ABSTRACT

Minactivin (also known as Plasminogen Activator Inhibitor-2 [PAI-2]), a protein inactivator of urokinase-type plasminogen activator, has been shown to be a natural inactivator of this plasminogen activator which is associated with invasive tumors, and is therefore indicated as a crucial element in the body's normal defense against tumor invasion and metastasis. It may be produced by the cultivation of minactivin-producing cells in vitro, and recovery of the cell culture supernatant. By controlling the culture conditions, the protein minactivin may be produced in a partially purified form which may be used for diagnosis and treatment of tumors. The specification discloses purification of biologically active native minactivin, as well as peptides derived from minactivin and their amino acid sequences. The specification also discloses methods for production of PAI-2 by recombinant DNA technology, characterization of a PAI-2 gene sequence, and expression and purification of large quantities of biologically active PAI-2 from a recombinant host.

20 Claims, 60 Drawing Sheets

OTHER PUBLICATIONS and its Complex Formation with Plasminogen Activator", *Thrombosis & Haemostasis*, 122–125 (1985).

Auron et al., "Nucleotide Sequence of Human Monocyte Interleukin 1 Precursor cDNA", *Proc. Natl. Acad. Sci.*, 81:7907–7911 (1984).

Chapman et al., "Macrophage Fibrinolytic Activity: Identification of Two Pathways of Plasmin Formation by Intact Cells and of a Plasminogen Activagor Inhibitor", Cell, vol. 28: 653–662 (1982).

Chapman et al., "Characterization of a Macrophage-derived Plasminogen-activator Inhibitor", *Biochem. J.*, 230:109–116 (1985).

Golder et al., "Minactivin: A Human Monocyte Product Which Specifically Inactivates Urokinase-type Plasminogen Activators", *Eur. J. Biochem.*, 136:518–522 (1983).

Holmberg et al., "Purification of Urokinase by Affinity Chromatography", *Biochem. of Biophysica Acta*, 445:215–222 (1976).

Holmberg et al., "An Inhibitor from Placenta Specifically Binds Urokinase and Inhibits Plasminogen Activator Released from Ovarian Carcinoma...", *Biochimica et Biophysica Acta*, 514:128–137 (1978).

Kruithof et al., "Partial Primary Structure of a PA Inhibitor Homologies with Other Serine Protease Inhibitors", *10th Int'l. Congress on Fibrinetysis*, Vienna 1986.

Kruithof et al., "Purification and Characterization of a Fast-acting Inhibotor of Urokinase (UK) from the Histiocytic Lymphoma Cell-line U-937", *10th Int'l. Congress on Thrombosis & Haemotosis* (1985).

Kruithof et al., "Partial Purification and Characterization of Plasminogen Activator Inhibitor (PAI-1) mRNA", *10th Int'l. Congress of Thrombosis & Haemotosis*, 1985.

Kruithof et al., "Studies on Prourokinase and Plasminogen Activator Inhibitor Biosynthesis in Phorbol Ester Induced U-937", *10th Int'l. Congress of Thrombosis & Haemotosis*, 1985.

Kruithof et al., "Purification and Characterization of a Plasminogen Activator Inhibitor from the Histiocytic Lymphoma Cell Line U-937", *J. Biological Chem.*, 261(24):11207–11213 (1986).

Kopitar et al., "Human Leucocyte Urokinase Inhibitor—Purification Characterization and Comparative Studies Against Different Plasminogen Activators", *Thrombosis & Haemostasis*, 54(4):750–755 (1985).

Lecander et al., "Differential Inhibition of Two Molecular Forms of Melanoma Cell Plasminogen Activator by a Placental Inhibitor", *British J. Haematology*, 57:407–412 (1984).

Lecander et al., "Isolation of a New Specific Plasminogen Activator Inhibitor from Pregnancy Plasma", *British J. Haematology*, 62:221–228 (1986).

Philips et al., "Immunological Relationship Between the Fast-Acting Plasminogen Activator Inhibitors from Plasma, Blood Platelets and Endothelial Cells...", *Thrombosis & Haemostasis*, 55(2):213–217.

Sakasela et al., "Urokinase-Type Plasminogen Activator and Its Inhibitor Secreted by Cultured Human Monocyte-Macrophages", *J. Cellular Physiology*, 132:122–125 (1985).

Van Mourik et al., "Purification of an Inhibitor of Plasminogen Activator (Antiactivator) Synthesized by Endothelial Cells", *J. Biol. Chem.*, 259(23):14914–14921 (1984).

Vassalli et al., "Human Monocytes-Macrophages and U-937 Cells Synthesize and Secrete a Plasminogen Activator-Specific Protease Inhibitor", Abstract, 7th International Congress on Fibrinolysis, Venice, Italy, Mar. 27–30, 1984, Hemostasis, 14(1):95.

Vassalli et al., "Concomitant Secretion of Prourokinase and of a Plasminogen Activator-Specific Inhibitor by Cultured Human Monocytes-Macrophages", *J. Exp. Med.*, 1653–1668 (1984).

Webb et al., "Sequence, Chromosomal Assignment, and Homology to Plasminogen Activator-Inhibitor", *J. Exp. Med.*, 166:77–91 (1987).

Wohlwend et al., "Plasminogen Activator-Specific Inhibitors Produced by Human Monocytes/Macrophages", *J. Exp. Med.*, 165:320–339 (1987).

Wun et al., "An Inhibitor of Plasminogen Activation from Human Placenta", *J. Biol. Chem.*, 262(8):3546–3653 (1987).

Ye et al., "cDNA Cloning and Expression in *Escherichia coli* of a Plasminogen Activator Inhibitor from Human Placenta", *J. Biol. Chem.*, 262(8):3718–3725 (1987).

Young et al., "Efficient Isolation of Genes by Using Antibody Probes", *Proc. Natl. Acad. Sci.*, 80:1194–1198 (1983).

FIG. 40

HPA 55

HPA 33

HMW LMW UK | HMW UK | LMW UK | PLASMINOGEN TREATED LMW UK

ELUTION PROFILE OF
IMMUNOAFFINITY COLUMN

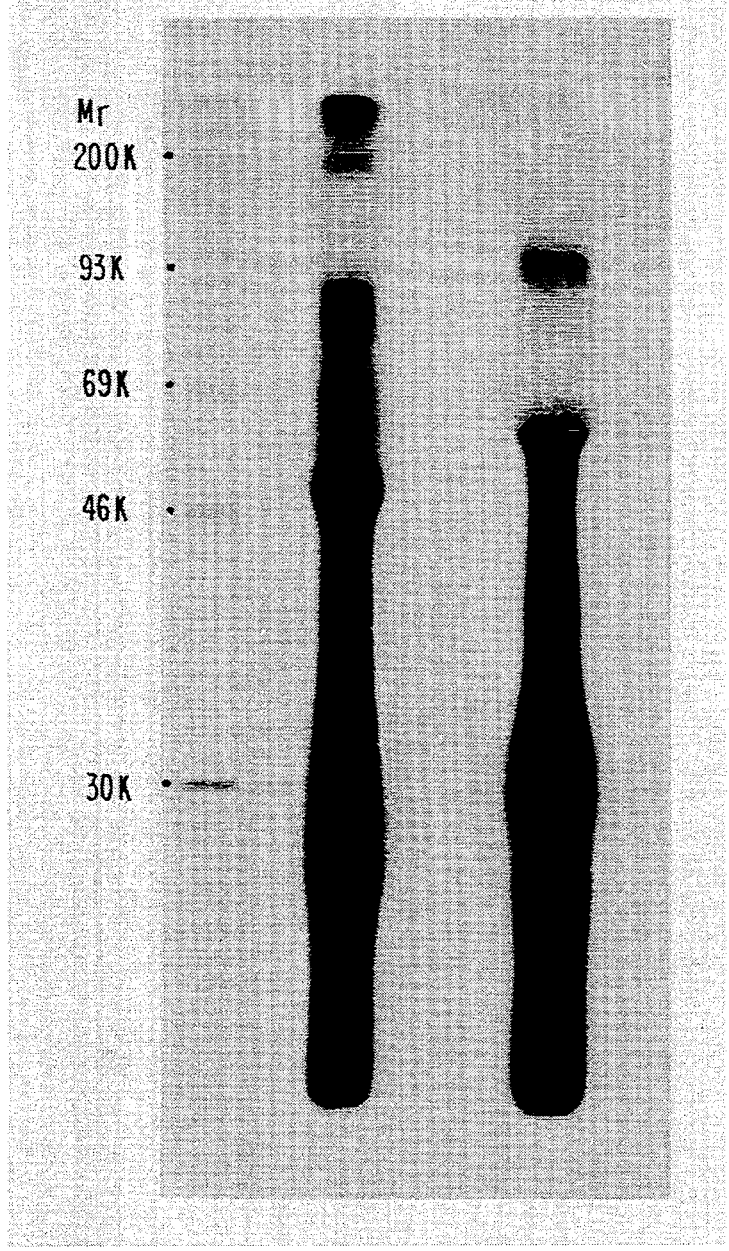

```
FROM FIG. 56A                                                                                      FROM FIG. 56A 1069                                    1099
      GAC GCC TTC AAC AAG GGA CGG GCC AAT TTC TCA GGG ATG TCG GAG AGG AAT GAC CTG TTT CTT TCT GAA GTG TTC CAC CAA GCC ATG GTG
1039  Asp Ala Phe Asn Lys Gly Arg Ala Asn Phe Ser Gly Met Ser Glu Arg Asn Asp Leu Phe Leu Ser Glu Val Phe His Gln Ala Met Val
                             1159        PEPTIDE 11                 1189
      GAT GTG AAT GAG GAG GGC ACT GAA GCA GCC GCT GGC GCA GGA GGT GTT ATG GGA AGA GGA CAT GGA ACT GGA GGC CCA CAG TTT GTG GCA
1129  Asp Val Asn Glu Glu Gly Thr Glu Ala Ala Ala Gly Ala Gly Gly Val Met Gly Arg Gly His Gly Thr Gly Gly Pro Gln Phe Val Ala
                                   1249                                   1279
      GAT CAT CCT TTT CTT CTT TTT ATT ATG CAT AAG ATA ACC AAC TGC ATT TTA TTT TTC GGC AGA TTT TCC TCA CCC TAA AAC TAA GCG TGC
1219  Asp His Pro Phe Leu Phe Leu Ile Met His Lys Ile Thr Asn Cys Ile Leu Phe Phe Gly Arg Phe Ser Ser Pro ***
1309                                          1339                                  1369                                  1399
      TGCTTCTGCAAAAGATTTTGTAGAATGAGCTGTGTGCCTCAGAATTGCTATTTCAAATTGCCAAAAATTTAGAGATGTTTTCTGCTCTTCTGAACAACTTCTGCTACCA
1429                                  1459                                  1489                                  1519
      CTAAATAAAACACAGAAATAATTAGACAATTGTCTATTATAACATGACAACCCTATTAATCATTTGGTCTTCTAAAATGGGATCATGCCCATTTAGATTTCCTTACTATCAGTTTATT
1549                                  1579                                  1609                                  1639
      TTTATAACATTAAACTTTTACTTTGTTATTTATTATTTGTATTGTGAGTTTAATTATTGCTCACTGCCTCCATGCCCTTCTGTAATAAATATCTGGAAAAAACATTAAACAATAGCCAAATATGTTATG
1669                                  1699                                  1729                                  1759
      TTCCTATCTAATAAATGCCTTTAATGTCTCATAAATGAAGAATAAGTAGGTATCCCTCCATGCCCTTCTGTAATAAATATCTGGAAAAAACATTAAACAATAGCCAAATATGTTATG
1789                                  1819                                  1849                                  1879
      TGCATTTCTAGAAATATACATAACACATATATGTCTGTATCTTATATTCAAGTATTATTCAAGATTCATAATTTCAAGACCAGGACCCTGGCCAACATGGCGAAACCCTACCTCCACTAAA
1909                                  1939                                  1969                                  1999
      AATACAGAAATGAGCCGGGAGTGGTGGCAAAGTGGTGAGCCACTGTGAGGGCCGAGCCAGGACCAATCACTTGAACCCAGGAGGCCGAGCCTGCAGTGAGCTGAGA
2029                                  2059                                  2089                                  2119
      TCGCTCCACTGCACTCCAGCCTGGGCAACAGAGCAAGATTCCATCTCAAATACATTAAAAAAAACCTATCTGAGGACTCTGAAAGTAAGCAGATAGATTTGAGAAGGGA
2149                                  2179                                  2209                                  2239
      ACTAGAACTTGAAGCACACAATCTATCTGGTGCTCTCTTTCTACTTTTGCTTGTTTCTCCCAATTCTACAGTTCTTCCAGTTCTTCCCAATTCTAGAAATGTATACCAGCCATGAAGA
2269                                  2299                                  2329                                  2359
      GATAAAGCTCCAAGAGAGGAGATTTCTTTCTTCTCGTATAAGGTATGTGTGTGTATAATGGGGGGCGATAAGGTTGGGAGTGTGAGGAATACAGAGTCCGGAGAATACCATTATTTCCACCCTCT
2389
      CTCTTGCCATTGCAACCAGAC
2409
```

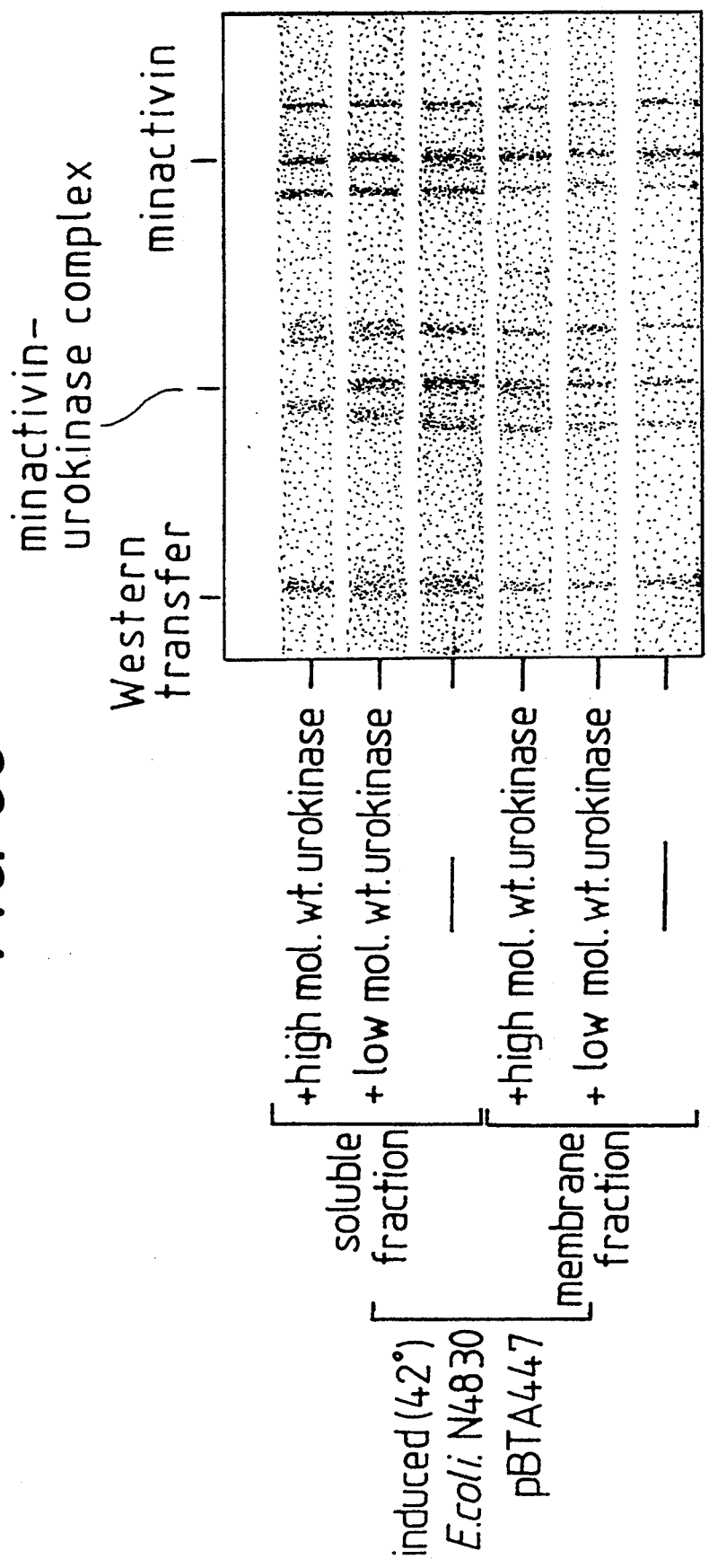

CELL ENVELOPE PREPARATIONS OF E. COLI N4830 pBTA586 FROM UNINDUCED (30°c) AND INDUCED (42°c) CULTURES SDS-PAGE

HUMAN PAI-2

The present application is a continuation-in-part of application Ser. No. 07/765,495, filed Sep. 26, 1991, now abandoned, which is a continuation of application Ser. No. 06/860,336, filed Jun. 13, 1986, now abandoned. The present application is also a continuation-in-part of application Ser. No. 07/693,542, filed Apr. 30, 1991, now abandoned, which is a divisional of application Ser. No. 07/025,815, filed Mar. 13, 1987, now abandoned.

The present invention relates to a new protein isolated from certain cells, which protein acts as a specific inactivator of urokinase-type plasminogen activator.

This invention relates to a specific inactivator of urokinase-type plasminogen activator which has been identified and isolated in adherent monolayer cultures of human blood monocytes, certain macrophages and transformed cells of monocytic origin. The inactivator has been given the name "minactivin", and this name will be used throughout this specification to refer to this product.

Plasminogen activators are proteolytic enzymes present in many animal tissues and secretions. The most widely known function of plasminogen activator is to catalyse the conversion of plasminogen to its active form, plasmin. The main role of plasmin is that of fibrinolysis, or the dissolution of blood clots. Two types of mammalian plasminogen activator, differing in molecular weight, amino acid sequence and immunological reactivity have been characterised in humans; urokinase-type plasminogen activator and tissue-type plasminogen activator. Several major types of human cancers, including carcinomas of the breast, lung, colon and prostate have been shown to produce abnormally high levels of the urokinase-type plasminogen activator, and several lines of evidence indicate that this factor is involved in the process by which tumours invade surrounding tissues.

GENERAL DESCRIPTION OF THE INVENTION

The present invention is based upon the discovery that the culture supernatant from adherent monolayer cultures of human blood monocytes contains minactivin, a potent inactivator of urokinase-type plasminogen activator. Minactivin has been shown to be a natural inactivator of this plasminogen activator which is associated with invasive tumours, and is therefore indicated to be a crucial element in the body's normal defence against tumour invasion and metastasis. Minactivin furthermore has a range of potential applications as a clinical reagent in the area of human medicine, in the in vitro and in vivo diagnosis of various types of carcinomas, as well as in the treatment of these conditions. Minactivin has also been isolated and indentified from cultures of macrophages and transformed cells of monocytic origin.

According to a first aspect of the present invention, there is provided as a substantially purified product, minactivin, a specific inactivator of urokinase-type plasminogen activator. This invention also provides a culture supernatant containing minactivin, a specific inactivator of urokinase-type plasminogen activator, this culture supernatant having been derived by the culture of minactivin-producing cells in vitro. The invention further provides a product derived from a culture supernatant containing minactivin, in which the minactivin has been at least partially purified. Further features characteristic of minactivin are described in detail hereinafter.

In another aspect of the present invention, there is provided the process for the production of minactivin, which process comprises the cultivation of minactivin-producing cells in vitro, and recovery of the culture supernatant. Minactivin may be recovered from the culture supernatant as an at least partially purified product. The cells which may be cultured to produce minactivin include human blood monocytes, certain macrophages and a transformed human cell line as disclosed in greater detail hereinafter. Culture supernatant containing minactivin secreted by the cells can be treated so as to concentrate the minactivin contained therein, and then treated so as to produce minactivin in an at least partially purified form, from which other components of the culture supernatant have been removed. This concentration and purification may be achieved, for example, by hydrophobic interaction chromatography on phenyl-Sepharose, or ion exchange chromatography using DEAE-Sepharose, followed by elution of the desired product therefrom. This product may be further purified by affinity chromatography, for example on Cibacron Blue-Sepharose or hydroxylapatite to remove further impurities from the minactivin-containing product.

Investigations have shown that minactivin is a protein characterized by an apparent molecular size of approximately 60–70,000 (by gel chromatography), and that its inhibitory effect is specific for plasminogen activators (such as urokinase) of $M_r$ 52,000 (HPA52) and 36,000 (HPA36) as shown by (i) inhibition of plasminogen-dependent fibrinolysis, (ii) inhibition at the level of plasminogen activation in a colorimetric assay, and (iii) irreversible loss of plasminogen activating activity, as evidenced by electrphoresis, after preincubation with culture media. Complex formation by minactivin and the HPA36 form of plasminogen activator was shown to be detergent resistant and characterized by a $M_r$ in the range of 70–75,000 (minactivin-HPA36 complex).

It has further been shown that minactivin preferentially inhibits urokinase-type plasminogen activator, and not trypsin, plasmin or "tissue" type plasminogen activator (HPA66 or 66,000 $M_r$ activator).

Minactivin has been found to be produced not only by human monocytes, but also by certain macrophages and transformed cells of macrophage lineage. In particular, peritoneal macrophages and bone marrow macrophages, when cultured in adherent monolayer cultures, have been found to produce and secrete appreciable amounts of minactivin. The human macrophage cell line, U937, has also been found to produce minactivin when cultured in the presence of dexamethasone. In a further development of this aspect of the invention, it has been discovered that the production of minactivin by blood monocytes in adherent monolayer culture can be stimulated or enhanced by the activation of the cells by use of muramyl dipeptide (adjuvant peptide), bacterial lipopolysaccharide or the lymphokine-containing supernatants from cultures of activated human lymphocytes.

When added to cultures of the human colon carcinoma cell line, COLO394, minactivin was found to specifically inactivate plasminogen activator (HPA52) as evidenced by colorimetric assay and electrophoresis. Furthermore, minactivin was capable of specifically inhibiting plasminogen activator activity in human tumour tissue homogenates obtained following surgical resection. It has been demonstrated that plasminogen activator levels are considerably elevated in tumour tissues compared with normal tissues from corresponding colons. Similar observations have been documented by other investigators with respect to a wide range of solid tumours.

Therefore, in view of minactivin's specificity for urokinase-type plasminogen activator and the markedly enhanced levels of this plasminogen activator in tumour tissues, this product has application as a reagent for locating and defining the boundaries of tumours in histological specimens and in vivo. Thus, minactivin can be used to image tumours in vivo. In particular, solid tumours such as breast, prostate, colon and lung, which produce plasminogen activator, can be targeted by minactivin. While such cancers are generally redressed by surgical intervention, the use of minactivin in imaging such tumours can be of particular benefit in the identification of small metastatic cancers arising after surgical intervention. It will, of course, be appreciated that since minactivin is a natural product, it has the advantage of a lack of antigenicity and the avoidance of clearance problems within the body. In imaging such tumours in vivo, minactivin may be used in a labelled from, for example, labelled with an appropriate radioactive isotope (such as technetium$^{99}$), and after administration the location and boundaries of tumours imaged by minactivin may be determined by known radioisotopic procedures.

In the location and definition of boundaries of tumours in histological specimens, minactivin can be conjugated either with a radioactive isotope as described above, or it may be labelled by conjugation, using standard procedures, with an appropriate enzyme (or other suitable reagent such as fluorescein). On contacting a histological specimen with a minactivin-enzyme complex, the minactivin will react with the urokinase of its place of secretion and high concentration, thereby identifying the tumour boundaries. Detection of the minactivin-enzyme complex found at these locations of high concentration can be effected by known means, for example, by applying a substrate for the enzyme, followed by an indicator to detect action of the enzyme on the substrate.

In addition to the imaging of tumours, minactivin is also indicated for use in direct treatment of tumours by decreasing tumour plasminogen activator activity and, since this activity is implicated in the process by which the tumours invade surrounding tissues, regulation and particularly inhibition of tumour invasion can be achieved.

The present invention also relates to the production of a novel human protein, minactivin, by recombinant DNA technology, the characterization of the DNA sequence of the gene, and the expression and purification of large quantities of biologically active minactivin from a recombinant host. It also relates to the purification of biologically active native minactivin, as well as peptides derived from minactivin and their amino acid sequences.

Minactivin (PAI-2) is a naturally occurring inactivator of urokinase-type plasminogen activators. This type of plasminogen activator is found in abnormally high levels in many major human carcinomas, most notably lung, colon, breast and prostate. Plasminogen activators are serine proteases which are thought to mediate the proteolytic cascade involved in cellular translocation, migration and invasion. As such, they appear to be associated with tissue destruction and remodelling, and have been implicated in tumor growth and metastasis. They may also have a role in inflammatory reactions.

Plasminogen activators are generally found to be of two types: 1) urokinase-type and 2) tissue-type. Tissue-type plasminogen activator is mainly found in the blood and blood vessel walls and where it is responsible for activating the fibrinolytic defence system against thrombosis. Urokinase-type plasminogen activators do not appear to play a role in normal thrombolytic processes but have been implicated in those pathological events associated with invasion and tissue destruction, in particular, tumor metastasis and inflammatory reactions.

Several inhibitors specific for plasminogen activators have been described which include one isolated from placenta (Holmberg, L. Biochim. Biophys. Acta 544, 128–137 (1978)) and another (PAI-1) which is produced in cultured vascular endothelial cells (Van Mourik, J. A., Lawrence, D. A., Loskutoff, D. J., J. Biol. Chem. 259, 14914–14921 (1984)). Minactivin was found to be produced by blood monocytes and U937 cells and appears to be immunologically related to the placental inhibitor. The relationship between these various inhibitors is presently unknown.

As is the case with most other potent biologically active proteins, minactivin is produced in very small amounts in vivo, and as such, is difficult to purify and characterise by conventional biochemical approaches. Therefore, as large quantities of purified minactivin are required for further evaluation of its properties and biological efficacy in clinical applications, it is desirable to produce the protein using recombinant DNA techniques; that is, by cloning the minactivin gene into an alternate host, such as bacteria or animal cells. In order to clone minactivin it is desirable to purify to homogeneity the small amounts that can be so purified of naturally occurring minactivin in order to produce antibodies, amino acid sequences, peptide fragments and synthetic oligonucleotides derived from said purified minactivin. These reagents are of use in cloning strategies.

ABBREVIATIONS

HPLC—High pressure liquid chromatography
$M_r$—relative molecular mass
MW—molecular weight
PMA—4-phorbol-12-myristate-13-acetate.
SDS-PAGE—sodium dodecyl sulfate polyacrylamide gel electrophoresis
TFA—trifluoroacetic acid
HPA—human plasminogen activator
bp—base pairs
kb—kilobase pairs.
PU—Ploug In a first embodiment, the invention provides a DNA sequence comprising a first DNA sequence which acts as a coding sequence for amino acid sequences of all, part, analogues, homologues, derivatives or combinations thereof of minactivin, a DNA sequence which hybridizes to said first DNA sequence, a DNA sequence related by mutation, including single or multiple base substitutions, deletions, insertions and inversions, to said first DNA sequence or hybridizing sequence of a DNA sequence which on expression codes for all, part, analogues, homologues, derivatives or combinations thereof of a polypeptide which is minactivin or which displays similar immunological or biological activity to minactivin.

A preferred DNA sequence and fragments and derivatives thereof, according to the invention codes for a polypeptide displaying an immunological or biological activity of minactivin.

Such DNA sequences can be prepared for example from mammalian cells by extracting total DNA therefrom and isolating the sequences by standard techniques for preparation of recombinant molecules.

Also within the scope of the invention is a process for selecting a DNA sequence coding for a polypeptide displaying an immunological or biological activity of minactivin from a group of DNA sequences, which process comprises the step of: determining which of said DNA sequences hybridises to a DNA sequence known to code for a polypeptide displaying said activity.

The selected sequence may be, for example from natural sources, synthetic DNA sequences, DNA sequences from recombinant DNA molecules and DNA sequences which are a combination thereof.

A preferred embodiment of the invention provides a process for the manufacture of a cDNA sequence which acts as a coding sequence for amino acid sequences of minactivin, which process comprises the steps of: stimulating cells to produce minactivin; obtaining RNA from said stimulated cells; isolating mRNA therefrom; and producing said cDNA from said mRNA. Preferably the cells are U937 cells.

The more preferred process for molecular cloning of the cDNA for minactivin and expression of the protein in a recombinant host includes the following methods:
1. induction of a cell line for stimulated minactivin production and expression.
2. isolation of mRNA from the appropriate cell line.
3. in vitro translation of the mRNA and immunoprecipitation of the minactivin translation product by complex formation with urokinase.
4. fractionation of mRNA from (2) and identification of the fraction containing minactivin translational activity.
5. construction of cDNA libraries from the mRNA from (2) and (4).
6. cloning of the cDNA libraries from (5) into suitable hosts, for example, E. coli or bacteriophage lambda.
7. identification of clones containing the minactivin gene by:
   a) hybrid-select translation employing (3);
   b) hybridization to a chemically synthesized DNA sequence probe, especially a probe comprising a synthetic oligonucleotide probe according to the invention;
   c) differential hybridization using labelled cDNA synthesized from induced and noninduced mRNA;
   d) immunological screening of cDNA expression libraries using antibodies directed against minactivin or other immunologically related molecules;
   e) screening of cDNA expression libraries for biological activity using labelled urokinase or urokinase and antibodies to urokinase.
8. extension of the cloned gene by generation cDNA libraries using oligonucleotide primers obtained from partial minactivin gene sequences, especially oligonucleotide sequences disclosed within the scope of the invention.
9. determination of the nucleotide sequence of the minactivin gene.
10. expression of the minactivin gene in E. coli and refolding to obtain biologically active product.
11. expression of biologically active recombinant minactivin by cloning into alternate hosts, for example, eukaryotic cells.
12. purification of recombinant minactivin and clinical assessment of its biological properties.

In a second embodiment, the invention provides a recombinant DNA molecule which includes a first DNA sequence comprising a first DNA sequence which acts as a coding sequence for amino acid sequences of all, part, analogues, homologues, derivatives or combinations thereof of minactivin, a DNA sequence which hybridizes to said first DNA sequence, a DNA sequence related by mutation, including single or multiple base substitutions, deletions, insertions, and inversions, to said first DNA sequence or hybridizing sequence or a DNA sequence which on expression codes for all, part, analogues, homologues, derivatives or combinations thereof of a polypeptide which is minactivin or which displays similar immunological or biological activity to minactivin.

Preferred recombinant DNA molecules of the invention include an expression control sequence operatively linked to a first DNA sequence comprising a first DNA sequence which acts as a coding sequence for amino acid sequences for all, part, analogues, homologues, derivatives or combinations thereof of minactivin, a DNA sequence which hybridizes to said first DNA sequence, a DNA sequence related by mutation, including single or multiple base substitutions, deletions, insertions and inversions, to said first DNA sequence or hybridizing sequence or a DNA sequence which on expression codes for all, part, analogues, homologues, derivatives or combinations thereof of a polypeptide which is minactivin or which displays similar immunological or biological activity to minactivin.

A preferred recombinant DNA molecule of the invention is a plasmid which acts as a coding sequence for amino acid sequences of minactivin.

A preferred plasmid of the invention has a first DNA sequence coding for a means of controlling expression of the DNA sequence of the invention linked to the DNA sequence of the invention.

The invention also provides a fused gene comprising a portable promoter, a translation start site, and a gene coding for human minactivin.

Also within the scope of the invention is a process for the manufacture of a recombinant DNA molecule, which process comprises the step of: introducing into a cloning vehicle, a first DNA sequence comprising a first DNA sequence which acts as a coding sequence for amino acid sequences of all, part, analogues, homologues, derivatives or combinations thereof of minactivin, a DNA sequence which hybridizes to said first DNA sequence, a DNA sequence related by mutation, including single or multiple base substitutions, deletions, insertions and inversions, to said first DNA sequence or hybridizing sequence or a DNA sequence which on expression codes for all, part, analogues, homologues, derivatives or combinations thereof of a polypeptide which is minactivin or which displays similar immunological or biological activity to minactivin.

Preferably the process also includes the step of introducing an expression control sequence into the cloning vehicle.

The invention further provides a process for the manufacture of a plasmid which acts as a coding sequence for amino acid sequences of all, part, analogues, homologues, derivatives or combinations thereof of minactivin, which process comprises combining a plasmid with a DNA sequence which acts as a coding sequence for said amino acid sequences, and preferably with an expression control sequence. The DNA sequence is preferably a cDNA sequence.

In a third embodiment, the invention provides a host transformed with at least one recombinant DNA molecule which includes a first DNA sequence comprising a first DNA sequence which acts as a coding sequence for amino acid sequences of all, part, analogues, homologues, derivatives or combinations thereof of minactivin, a DNA sequence which hybridizes to said first DNA sequence, a DNA sequence related by mutation, including single or multiple base substitutions, deletions, insertions and inversions, to said first DNA sequence or hybridizing sequence or a DNA sequence which on expression codes for all, part, analogues, homologues, derivatives or combinations thereof of a polypeptide which is minactivin or which displays similar immunological or biological activity to minactivin.

Suitable hosts include bacteria, yeasts, other fungi, mice or other animal hosts, plant hosts, insect hosts and other eukaryotic hosts e.g. mammalian, including human tissue cells. Suitable bacteria include *E. coli*, Pseudomonas species, and Bacillus species.

Especially preferred is a microorganism with the genetic information for the biosynthesis of minactivin.

Also included within the invention is a process for transforming a host, which process comprises the steps of: introducing into a host a recombinant DNA molecule which includes a first DNA sequence comprising a first DNA sequence which acts as a coding sequence for amino acid sequences of all, part, analogues, homologues, derivatives or combinations thereof of minactivin, a DNA sequence which hybridizes to said first DNA sequence, a DNA sequence related by mutation, including single or multiple base substitutions, deletions, insertions and inversions, to said first DNA sequence or hybridizing sequence or a DNA sequence which on expression codes for all, part, analogues, homologues, derivatives or combinations thereof of a polypeptide which is minactivin or which displays similar immunological or biological activity to minactivin.

The invention also provides a process for the manufacture of a microorganism with the genetic information for the biosynthesis of all, part, analogues, homologues, derivatives or combinations thereof of minactivin, which process comprises transforming a microorganism with a plasmid or other vector which acts as a coding sequence for amino acid sequences of all, part analogues homologues, derivatives or combinations thereof minactivin.

In a fourth embodiment, the invention provides a process for the preparation of peptides derived from purified minactivin which process comprises purifying minactivin to homogeneity then obtaining amino acid sequences unique to minactivin.

A preferred embodiment of this process comprises:
a) Culturing a cell line capable of expressing minactivin;
b) harvesting the supernatant;
c) concentrating the supernatant;
d) dialysing and supernatant, then centrifuging said culture supernatant to remove residual cell debris and protein which may have precipitated during dialysis;
e) fractionating the culture supernatant chromatographically and electrophoretically;
f) concentrating the fraction containing minactivin activity;
g) analysing the fraction containing minactivin activity to demonstrate purity;
h) obtaining amino acid sequences unique to minactivin.

In a preferred form the process comprises:
a) culturing a minactivin producing culture or cell line;
b) harvesting the culture supernatant and concentrating said culture supernatant;
c) dialysing the culture supernatant, then centrifuging said culture supernatant to remove residual cell debris and protein which may have precipitated during dialysis;
d) fractionating the culture supernatant by ion exchange chromatography;
e) pooling and concentrating the eluates of highest minactivin specific activity;
f) fractionating the pooled, concentrated eluates by gel filtration chromatography;
g) concentrating the eluate then isoelectrofocussing said eluate;
h) probing fractions isolated from the isoelectrofocussing gel with antibodies reactive with minactivin, to locate the minactivin band;
i) concentrating the fraction containing minactivin activity;
j) further fractionating the fraction containing minactivin activity by partition chromatography then analysing the purified fraction containing minactivin activity by gel electrophoresis;
k) digesting the purified minactivin and separating the resulting peptides by partition chromatography.

In a more preferred form the culture is of the human macrophage cell line U937. Preferred culture conditions include culturing in the absence of serum and/or in the presence of a sufficient amount of a substance or substances which will inhibit urokinase production or induce constitutive production of minactivin. A suitable substance for this purpose is dexamethasone which is preferably used at a concentration of 1 $\mu$M. The culture may also be grown in the presence of PMA. A preferred concentration range of PMA in the culture is 1–300 ng/ml, more preferably 10–30 ng/ml.

A preferred volume of harvested culture supernatant is 4–5 liters. The initial concentration step is preferably a 10-fold concentration step. A suitable apparatus for this concentration is an Amicon DC2 Hollow Fibre Dialysis/Concentration unit equipped with a 30 000 MW cut off cartridge.

The dialysis according to step c) is preferably with a dialysate such as 50 mM glycine, pH7.8. More preferably the 50 mM glycine pH7.8 dialysate should be used at at least equal volume to the volume of the sample being dialysed against said dialysate.

The ion exchange chromatography according to step d) is preferably performed on a phenyl-sepharose column, the elution being preferably a step pH elution. More preferably, for the pH step elution, the ionic strength of the supernatant should be adjusted to 2M, especially this may be by the addition of solid NaCl, then the pH should be adjusted to 5.5 preferably with citric acid. A preferred equilibrant for the phenyl-sepharose column is a solution of 50 mM Na citrate pH5.5 2M NaCl and 1 mM EDTA. The column may be eluted initially with equilibration buffer, then with 50 mM Na citrate pH5.5 containing 0.5M NaCl and 1 mM EDTA and finally with 50 mM glycine pH9.0.

The concentration of the sample according to step g) is preferably performed on an Amicon YM10 membrane, with a final concentrate volume of 3 ml. The isoelectrofocussing step is preferably performed on a preparative flatbed gel of Ultrodex containing Ampholines in the pH range 4.5 to 6.0. More preferably the gel is electrofocussed at 10° C. for 23 hours, on an LKB Multiphor isoelectrofocussing apparatus. A preferred elutant for proteins from the electrofocussing gel is 1M glycine containing 1 mM EDTA pH9.0, more preferably in a 10 ml volume. Suitable antibodies according to step h) include goat anti-placental inhibitor antibodies.

The concentration according to step i) may be performed on an Amicon YM10 membrane.

The partition chromatography according to step j) is preferably HPLC, more preferably performed on a Vydac C-4 reverse phase column using a Waters high pressure liquid chromatograph. The elution gradient is preferably acetonitrile in 0.1% TFA. Gel electrophoresis according to step j) is preferably SDS-PAGE.

Digestion of the purified minactivin, according to step k) is preferably with endoproteinase LysC. Suitable digestion conditions include 3–5 μg minactivin with 0.1 μg endoproteinase LysC in 20 mM Tris-Cl pH8.5, 5M urea, at a volume of 50 μl and 22° C. for 8 hours. A suitable form of partition chromatography is reverse phase HPLC, particularly employing a Synchropak RP-P(C-8) column with a gradient of acetonitrile in 0.1% TFA.

In a fifth embodiment the invention provides minactivin in substantially pure form. Preferably said minactivin is purified to homogeneity.

In a sixth embodiment the invention provides purified minactivin when prepared by a process according to the invention.

In a seventh embodiment the invention provides peptides derived from purified minactivin and peptides displaying similar immunological or biological activity to said peptides.

Preferred peptides according to the invention include peptides of the following sequences and which are also set forth in SEQ. ID. NOs. 1, 2, 3, 4 and 5, respectively:

```
AQILELPY—GDV—MFLLLP—E ...
GRANFSGMSE—NDLF ...
MAE—EVEVYIPQFKLEE—Y ...
LNIGYIEDLK
IPNLLPEG—V
```

The invention also provides peptides according to the invention when prepared by a process according to the invention.

In an eighth embodiment, the invention provides a microbiologically prepared peptide, all or part of which contains the amino acid sequence of all, part, analogues, homologues, derivatives or combinations thereof minactivin.

A peptide and fragments and derivatives thereof which display an immunological or biological activity of minactivin are also within the scope of the present invention.

The preferred peptide or fragments or derivatives thereof are coded for by a DNA sequence which hybridises to a DNA sequence which acts as a coding sequence for amino acid sequences of minactivin and displays the biological or immunological activity of minactivin, which activity is destroyed by antisera to minactivin.

The invention also provides a process for the manufacture of all, part, analogues, homologues, derivatives or combinations thereof of unglycosylated minactivin, which process comprises the steps of: obtaining the genetic information for the biosynthesis of minactivin using mRNA from cells of monocytic lineage; incorporating the resulting gene into a microorganism; selecting and culturing said microorganism to produce said minactivin; and collecting said minactivin.

The invention further provides a process for the manufacture of a peptide displaying an immunological or biological activity of minactivin, which process comprises the steps of: culturing a host which has been transformed with a recombinant DNA molecule which includes a first DNA sequence comprising a first DNA sequence which acts as a coding sequence for amino acid sequences of all, part, analogues, homologues, derivatives or combinations thereof of minactivin, a DNA sequence which hybridizes to said first DNA sequence, a DNA sequence related by mutation, including single or multiple base substitutions, deletions, insertions and inversions, to said first DNA sequence or hybridizing sequence or a DNA sequence which on expression codes for all, part, analogues, homologues, derivatives or combinations thereof of a polypeptide which is minactivin or which displays similar immunological or biological activity to minactivin.

The invention also provides a reagent for locating and defining the boundaries of tumours in histological specimens or in vivo which reagent comprises suitably labelled minactivin, especially recombinant DNA derived minactivin, or fragments of minactivin and the associated method of locating and defining the boundaries of tumours in histological specimens or in vivo which comprises applying or administering suitably labelled minactivin or fragments thereof and subsequently imaging to determine the site of concentration of the label.

The invention further provides a method of inhibiting tumour invasion and treating tumours comprising administering to a patient requiring such treatment a therapeutically effective amount of minactivin, suitably labelled minactivin, fragments of minactivin or labelled fragments of minactivin; a method of treatment of chronic inflammation such as rheumatoid arthritis comprising administering to a patient requiring such treatment a therapeutically effective amount of minactivin or fragments of minactivin; and a method of monitoring chronic inflammation comprising the detection of minactivin in samples of body fluids and tissues using antibodies prepared against minactivin or fragments of minactivin.

Also included within the invention are antibody preparations prepared against minactivin including recombinant minactivin, purified natural minactivin and fragments thereof. The invention also provides therapeutic, diagnostic or prophylactic compositions which comprise minactivin, especially recombinant DNA derived minactivin, fragments of minactivin or antibodies to minactivin or fragments of minactivin and a pharmaceutically acceptable non-toxic carrier or diluent therefor.

The invention further provides synthetic oligonucleotide probes, the sequence of said probes comprising a first nucleotide sequence which on expression codes for the amino acid sequence of a peptide according to the invention, a nucleotide sequence sufficiently related to said first nucleotide sequence to hybridize to said first nucleotide sequence or a DNA sequence related by mutation including single or multiple base insertions, inversions deletions or substitutions to said first nucleotide sequence.

Included within the scope of the invention is a process for the production of said synthetic oligonucleotide probes which process comprises determining the amino acid sequence of peptide fragments derived from purified minactivin and synthesizing corresponding oligonucleotides. In a preferred form said synthesis is performed on an Applied Biosystems 380A DNA synthesizer.

The invention provides formulations comprising synthetic oligonucleotide probes according to the invention.

Preferably said formulations are diagnostic reagents.

The invention also provides a method for the detection of human carcinomas and inflammatory conditions and susceptibility thereto which method comprises using a formulation comprising said synthetic oligonucleotide probe in an assay designed for the detection of DNA coding for minactivin. Deficiency in ability of tissues to produce minactivin may be related to susceptibility to carcinomas and inflammatory conditions. Detected deficiencies may be treated by administration of purified minactivin to the patient, and may also serve as a marker for tissues affected by carcinomas and inflammation.

BEST MODE OF CARRYING OUT THE INVENTION

Induction of U937 Cell Line for Enhanced Minactivin Synthesis

Minactivin has been found to be produced by induced human monocytes, certain macrophages, and transformed cells of monocytic lineage (refer to international patent application WO86/01212). The transformed cell line U937 (ATCC CRL 1593) was found to produce minactivin constitutively in the presence of dexamethasone. The level of minactivin secreted by these cells under serum free conditions was found to be only about 0.06% of the total protein secreted by these cells. It was found that this level could be enhanced by approximately an order of magnitude of 0.4% with the addition of 4-phorbol-12-myristate-13-acetate (PMA). The effect of PMA on minactivin secretion with time followed by a biphasic course with an initial lag period of 6 hours, followed by a linear increase in minactivin activity up to 60 hours (FIG. 34). No differences were observed by increasing the PMA concentration from 10 ng/ml to 30 ng/ml. Furthermore, it was determined that the phorbol esters were tightly associated with the cells, as radiolabelled PMA could be detected only in small amounts (less than 10%) in the culture supernatants even after 17 hours.

The following examples illustrate preferred embodiments of the invention. They should not be construed as limiting on the scope of the invention. Unless otherwise stated, all parts and percentages are by weight.

Figure 1A:
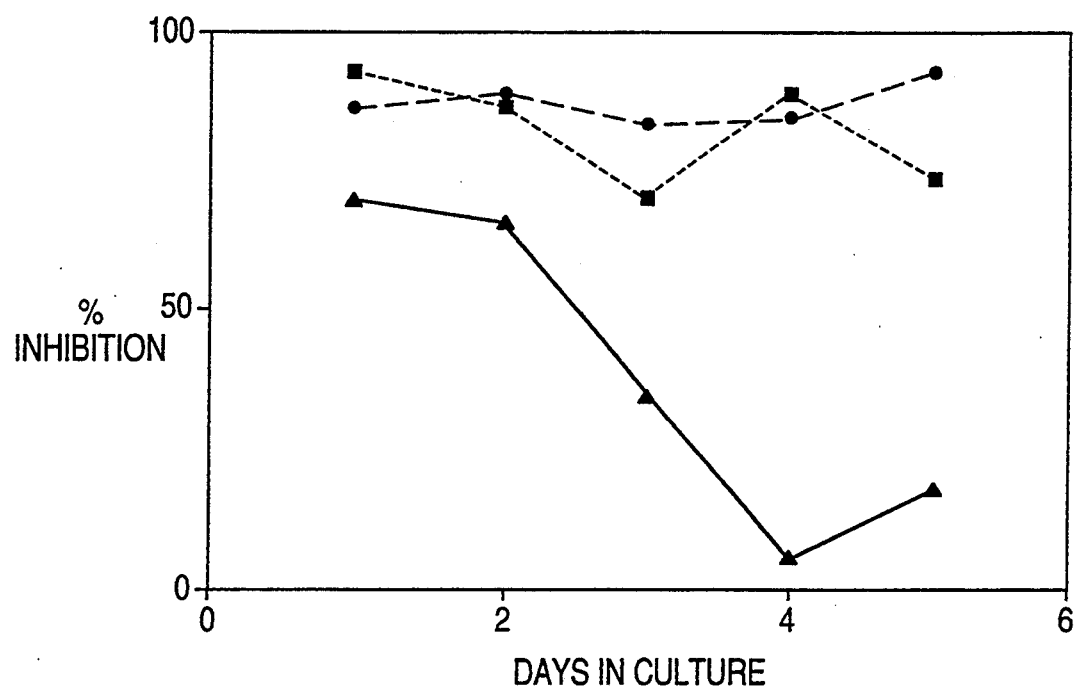
FIGS. 1A and 1B

Production of minactivin by blood monocyte cultures. Adherent monocytes were cultured in: control media △—△ with lipopolysaccharide (0.1 ug.ml) --- or with muramyl dipeptide (10 ug/ml) □ . . . □ A. Culture supernatants were harvested, assayed with urokinase and replaced with fresh media every 24 hrs. B. Content of minactivin in cell lysates.

FIG. 2

Dependence of minactivin activity on monocyte cell number in culture. Supernatants from 24 hr cultures with cell numbers shown were assayed undiluted △—△, diluted 1:5 □ . . . □, 1:10 - - -, or 1:20 - - -.

FIG. 3

Production and secretion of minactivin by human peritoneal macrophage culture. Adherent macrophages were grown in control media △—△, or with muramyl dipeptide (10 ug/ml) □ . . . □. The lower two curves represent lysates and the upper two curves, supernatants.

FIG. 4

Production and secretion of minactivin by human bone marrow macrophages in secondary culture. Conditions as for FIG. 3.

FIG. 5

Effect of Minactivin on Fibrinolysis

Protease solutions (10 ul) were preincubated with (upper two rows) or without (lowest row) minactivin culture supernatant (10 ul) and the mixture (5 ul) applied to wells cut in a plasminogen supplemented fibrin-/agarose gel. The enzymes and the amounts used per 20 ul of preincubation were: 2. trypsin, 100 ng; 3. plasmin, 600 ng; 4. CUK. (Calbiochem Urokinase) 50 mPU; 5. SUK, (Sigma Urokinase) 100 mPU; and 6. melanoma culture supernatant undiluted. The control wells 1 and 7 contained assay buffer and minactivin supernatant respectively. The gel was incubated for 20 hrs at 37°.

FIG. 6

SDS-PAGE after Preincubation with Minactivin

Plasminogen activators from CUK (30 mPU, lanes 1 and 2), MLA144 (30 ul undiluted culture supernatant, lanes 3 and 4), human melanoma (20 ul culture supernatant, lanes 5 and 6), and rat 13762 tumour (20 ul 1% homogenate, lanes 7 and 8) were preincubated with (even numbers) and without (odd numbers) minactivin culture supernatant (30 ul) before application to SDS-PAGE. The bands were developed in a fibrin overlay gel by incubation for 20 hours at 37°.

FIG. 7

Inactivation of CUK by preincubation with minactivin. Aliquots of urokinase (4 mPU) were preincubated with monocyte culture supernatant (6 ul) at 23° for the times shown, then assayed colorimetrically as described in the test. The upper curve is for urokinase preincubated with buffer.

FIG. 8

Titration of CUK with minactivin. Aliquots of urokinase (4 mPU) were preincubated with dilutions of the minactivin supernatant (20 ul), then assayed colorimetrically as described in the text.

FIG. 9A

Protease inhibitor controls for CUK inactivation by minactivin. Aliquots of urokinase (20 mPU) were preincubated with the following protease inhibitors: lane 1, buffer control; lane 2, Trasylol (0.2 mg/ml); lane 3, alpha₁ antitrypsin (16 ug/ml); lane 4, tranexamic acid (3 mM); lane 5, iodoacetamide (3 mM); lane 6, EDTA (6 mM); lane 7, soybean trypsin inhibitor (0.16 mg/ml); lane 8, SDS (0.6%); lane 9, benzamidine (3 mM); and lane 10, minactivin culture supernatant (20 ul).

FIG. 9B

Inactivation of CUK by minactivin in the presence of protease inhibitors. The preincubations in FIG. 9a above were repeated with minactivin culture supernatant (20 ul) included in each protease inhibitor preincubation (lanes 2–9).

FIG. 10

Elution profile of 2.5 ml of minactivin culture supernatant without albumin supplement —, and 1.0 ml of unconditioned RPMI with 1% human serum albumin - - - assayed for urokinase inhibition and protein respectively. The column was packed with Sephacryl S300 (95×1.5 cm) and eluted with 50 mM glycine (pH 7.8) containing 0.15M NaCl at a flow rate of 6 ml/hr. Arrows indicate void volume and bed volume.

FIG. 11

Radial diffusion fibrin gel assays of protease inhibition. Row A, human melanoma cell line supernatant containing HPA66; Row B, urokinase containing HPA52 and HPA36; Row C, trypsin and Row D, plasmin. Columns 1 and 2 included supernatants from cultures of human peritoneal macrophages and blood monocytes respectively, while columns 4–6 includes lysates of bone marrow macrophages, peritoneal macrophages and blood monocytes respectively. Columns 3 and 7 represent controls containing culture media and lysis buffer respectively.

FIG. 12

Radial diffusion fibrin gel assays of protease inhibition. Row A, Buffer control; Row B, phenyl-Sepharose purified minactivin from monocytes; Row C, phenyl-Sepharose purified minactivin from U937 cells; Row D, placental inhibitor (Calbiochem). Column 1, porcine plasmin 60 ug/ml (sigma); Column 2, urokinase containing HPA52; CUK, 5 PU/ml; Column 3, urokinase containing HPA36, SUK, 5 PU/ml; Column 4, human melanoma cell line supernatant, MM170, containing HPA66; Column 5, mouse urokinase, 1/10 dilution mouse urine.

Figure 13B:
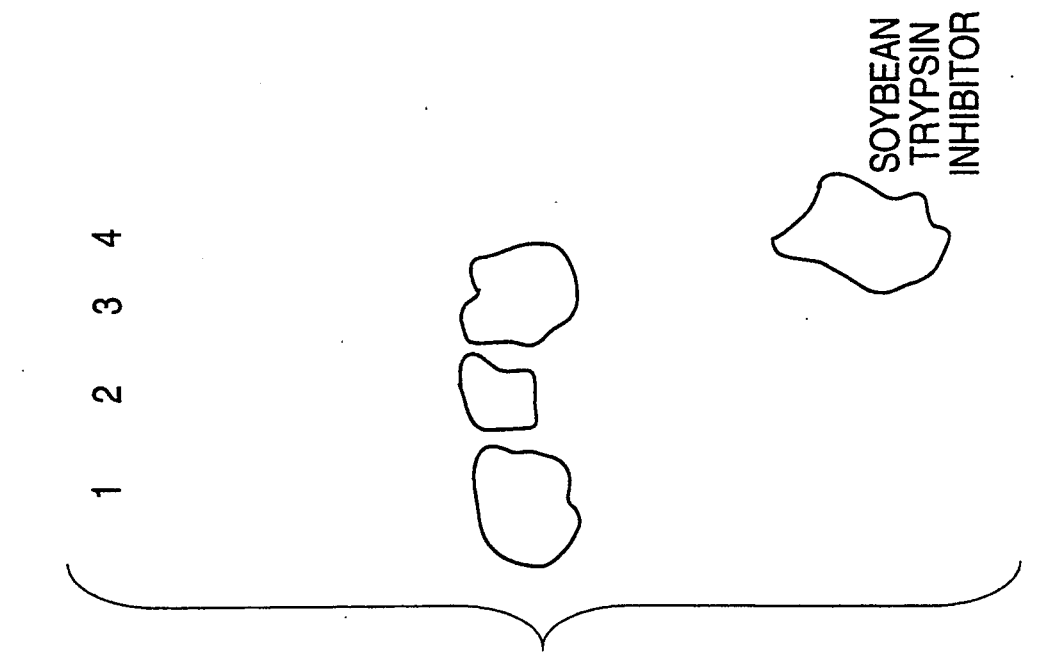
Figure 13A:
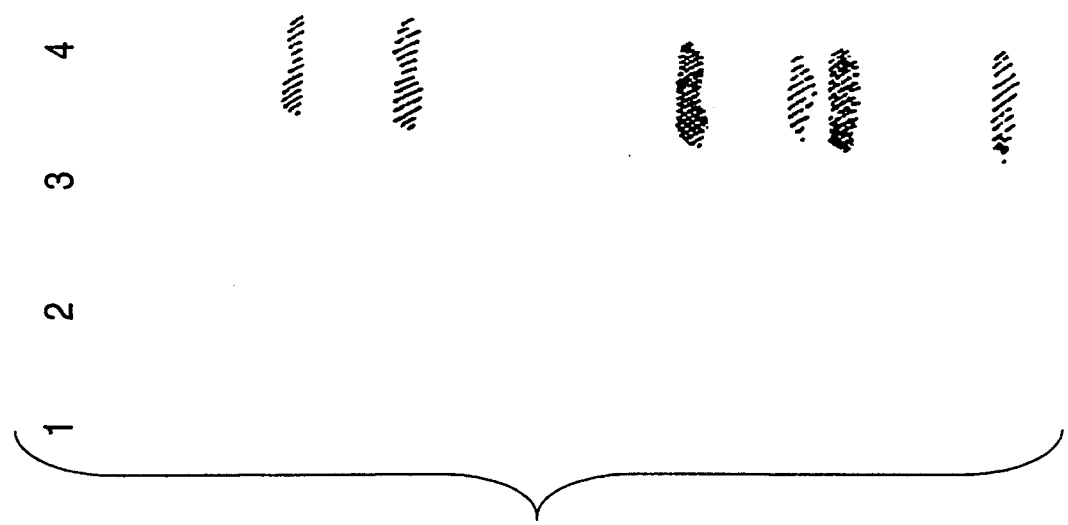

FIGS. 13A and 13B

Electrophoretic Mobility of U937 and Monocyte derived Minactivin. Samples were electrophoresed on a 6–16% gradient nondenaturing (no SDS) polyacrylamide gel, incubated with 10 mls SUK 1 PU/ml for 1 hr at 23° C., overlayed on a fibrin/agarose gel, and developed overnight. Identical samples were also electrophoresed and then stained with Coomassie Blue. Lane 4, molecular weight standards; Lane 3, phenyl-Sepharose purified U937 minactivin; Lane 2, phenyl-Separose purified monocyte minactivin; Lane 1, as lane 3.

FIG. 14

Purification Profile of Monocyte Minactivin on Phenyl-Sepharose. A column of phenyl-Sepharose (bed volume 110 ml) was first equilibrated with 50 mM glycine buffer pH 7.8 containing 2M NaCl. Monocyte supernatant adjusted to 2M NaCl was then applied, followed by washing with additional glycine-NaCl. Elution of bound minactivin occurred during a descending gradient of NaCl in glycine buffer. Traces are: Protein (by Lowry assay, OD750 nm)—NaCl concentration . . . and minactivin inhibition of urokinase (inverted peak) - - - .

FIG. 15

In vivo Labelling of Monocyte Minactivin.

Adherent monocytes were cultured in the presence of muramyl dipeptide as described in the text with the addition of $^{35}$S-Methionine (1 mCi, 800 Ci/mmol, Amersham). Aliquots of the supernatant were removed at the times indicated over the course of 3 days. Minactivin was then purified from the supernatant using phenyl-Sepharose as described in the text. Each aliquot was concentrated 50 fold using a Centricon 30 (Amicon), and 30 ul analysed by SDS-PAGE using a 5–15% acrylamide gradient. The radiolabelled proteins were detected by fluorography (Amplify, Amersham) and the gel exposed on Kodak O-MAT X-ray film for 10 days. Lanes 2–6 are samples removed at the times indicated, Lane 7 is the phenyl-Sepharose purified minactivin preparation. Lanes 1 and 8 are high and low molecular weight standards respectively.

FIG. 16

Purification of In Vivo Labelled Monocyte Minactivin and Urokinase Complex Formation.

Figure 15:
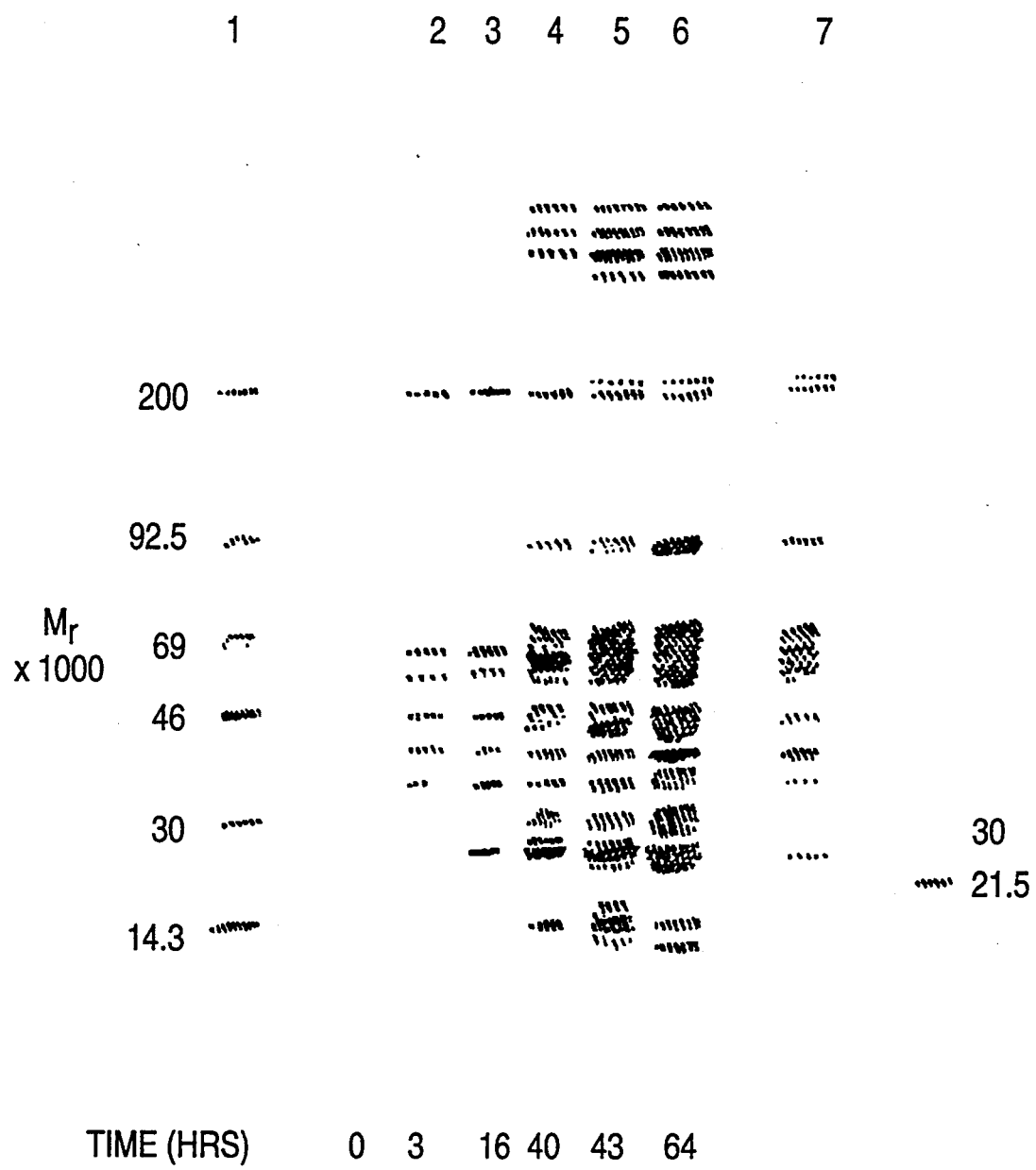

Conditions essentially as for FIG. 15 and as described in the text. Each sample was concentrated 10 fold before loading 30 ul on the gel. Exposure time was 18 days. Lanes A, phenyl-Sepharose purified minactivin; Lanes B, blue Sepharose purified minactivin; Lanes C, identical to B except 0.1% 2-mercaptoethanol added to the samples immediately prior to electrophoresis. Each sample is shown (−) or (+) preincubation with 27 PU SUK for 90 min at 23° C. Outside lanes are molecular weight standards.

FIG. 17

Effect of Gelatin on Minactivin Production.

U937 cells (1.3×10$^6$ cells/ml) were cultured in serum-free medium with dexamethasone as described in the text, in the presence (x—x) and in the absence (.—.) of 0.7% gelatin as described.

FIG. 18

Phenyl-Sepharose Chromatography using a Step pH Elution.

The chromatography was performed as described in Example 1. At position A the eluent was changed to 50 mM citrate, pH 5.0, 0.5M NaCl, and at position B the eluent was changed to 50 mM glycine, pH 7.8.

FIG. 19

DEAE-Sepharose Chromatography using Step-wise pH Elution.

Minactivin containing supernatants were fractioned on a DEAE-Sepharose column as described in Purification Example 3. Minactivin activity is shown in the open columns and protein - - - A275.

FIG. 20

Preparative Nondenaturing Gel Electrophoresis.

A phenyl-Sepharose purified minactivin preparation was further fractionated on by nondenaturing gel electrophoresis as described in Purification Example 4. Minactivin activity eluted from the gel slices is shown in the open columns. Beneath is shown an equivalent gel lane stained by the silver stain method.

FIG. 21

DEAE-Sephacel Chromatography using Salt Gradient Elution.

Minactivin containing supernatants were fractionated on a DEAE-Sephacel column as described in Purification Example 6. Units of biological activity are shown in the open columns: . . . , A275; - - - , NaCl concentration.

FIG. 22

DEAE-Sephacel Chromatography using a pH Gradient.

Minactivin containing supernatants were fractionated as described in Purification Example 7. Units of biological activity are shown in the open columns; protein content is shown in the closed columns; - - -, A275, - - -, pH.

FIG. 23

SDS-PAGE of Fractions from DEAE-Sephacel

Figure 22:
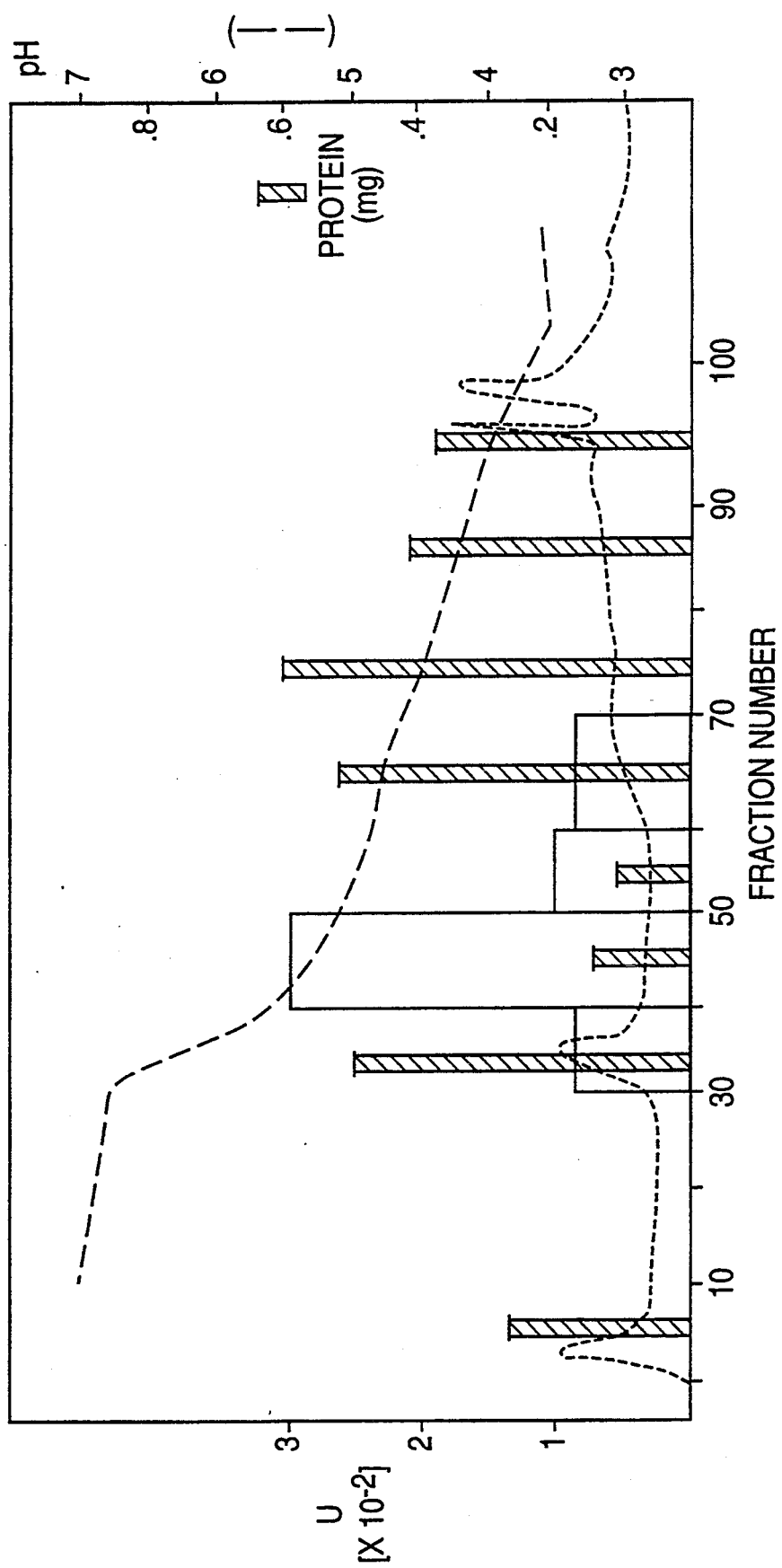

Aliquots equivalent to 70 ug of protein were removed from pooled fractions of the DEAE-Sephacel chromatography shown in FIG. 22 and analysed by SDS-PAGE as described by Laemmli (26). Lane 1, molecular weight markers; lane 4, fractions 30–40; lane 5, fractions 40–50; lane 6, 50–60; lane 7, 60–70; lane 8, 70–80; lane 9, 80–90; lane 10, 90–100.

FIG. 24

Hydroxylapatite Chromatography

Minactivin containing supernatants were fractionated as described in Purification Example 8. Units of biological activity are shown in the open columns; protein content is shown in the closed columns; . . . , A275; - - -, sodium phosphate concentration.

FIG. 25

SDS-PAGE of Fractions from Hydroxylapatite Chromatography.

Figure 24:
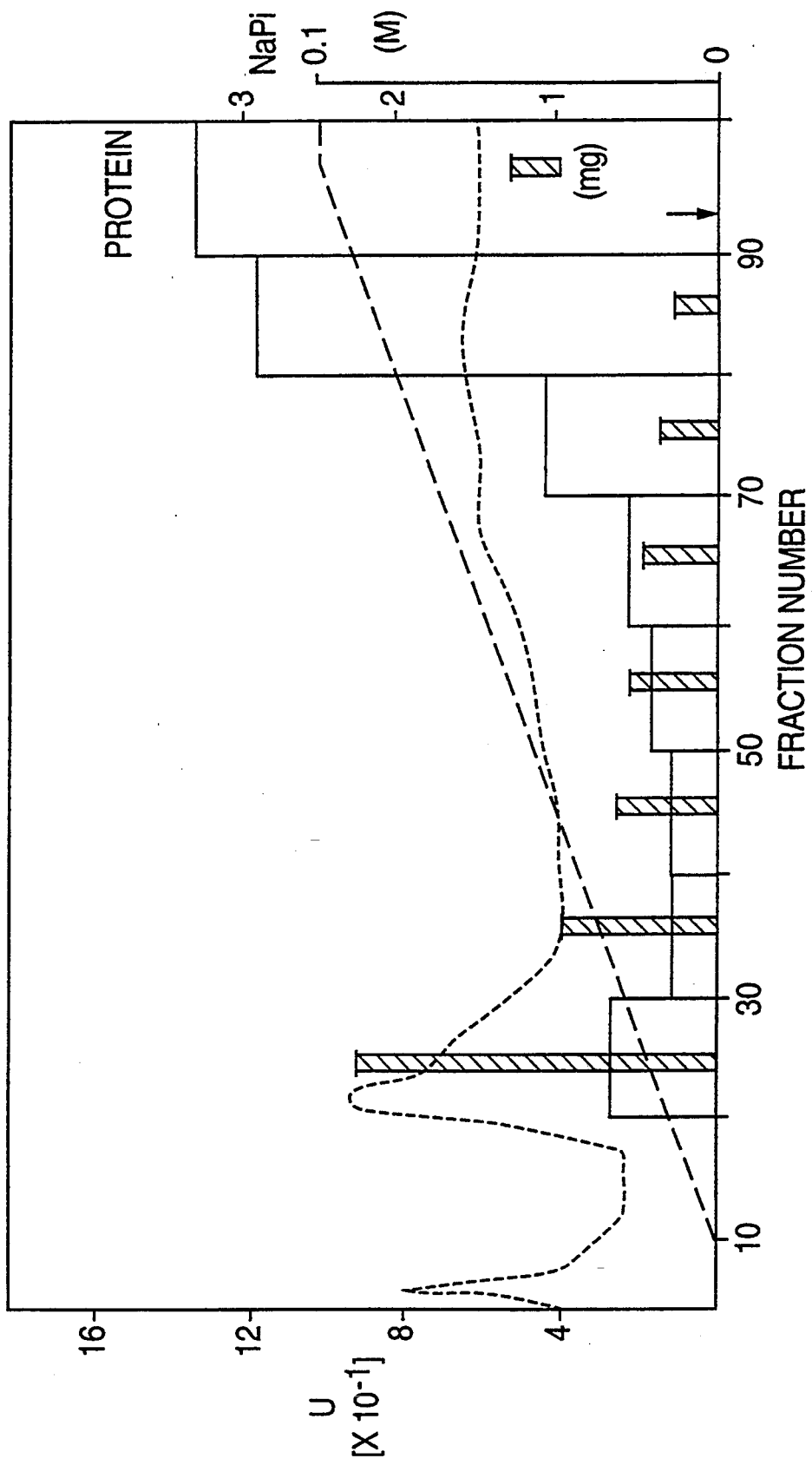

Aliquots equivalent to 70 ug of protein were removed from selected pooled fractions of the hydroxylapatite chromatography shown in FIG. 24, and analysed on SDS-PAGE as described by Laemmli (26). Lane 8, fractions 70–80; lane 9, fractions 80–90; lane 10, 90–100.

Figure 26A:
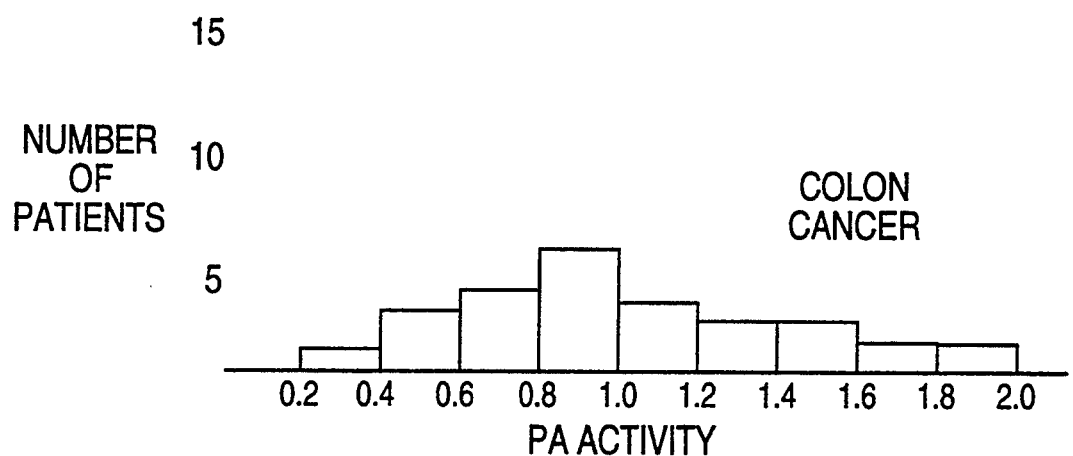
Figure 26B:
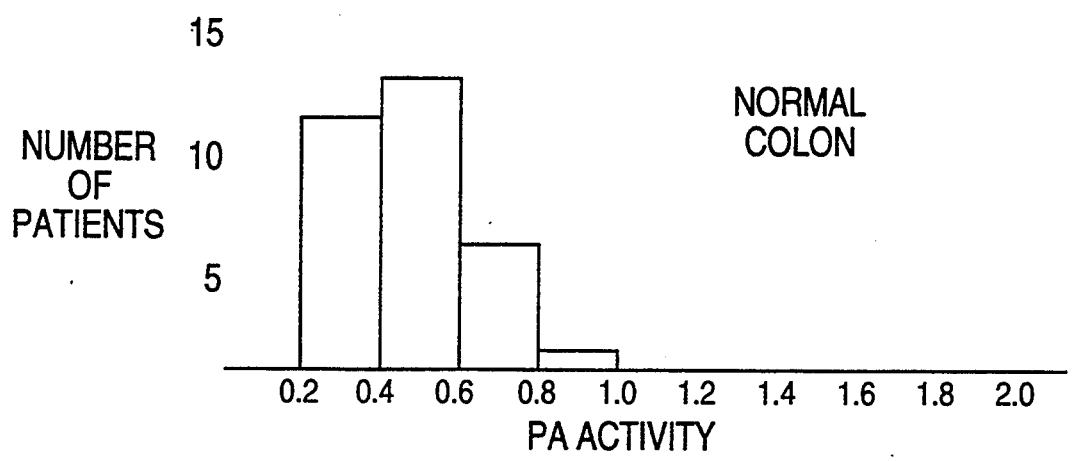

FIGS. 26A and 26B

Frequency distribution histograms showing the results from colorimetric assays of plasminogen activator in homogenates of human colonic mucosae. The plasminogen substrate contained traces of plasmin, such that results represent the sum of proenzyme and active enzyme. The activity is expressed as the absorbance at 412 nm. Under the same assay conditions, 4 mPU of commercial urokinase produced an absorbance of 0.9 at 412 nm.

FIG. 27

Plasminogen activator activity of 15 colon tumour specimens (striped rectangles) compared to the activity in normal tissue (solid rectangles) from the same colons. The samples were ranked left to right according to the increasing value of the tumour:normal ratio (T/N).

FIG. 28A

Types of plasminogen activator present in typical homogenate of normal colonic mucosa shown by fibrin agarose overlay after SDS-PAGE, Lane 1 represents untreated sample, Lanes 2–4 show the effects of incubating the homogenate for 30, 60 and 120 min at 37° with human plasminogen. Zones of lysis are: a) plasminogen activator of 110,000; b) plasminogen activator of $M_4$ 96,000; c) plasmin, $M_r$ 85,000 and d) HPA66, $M_r$ 66,000.

Figure 28A:
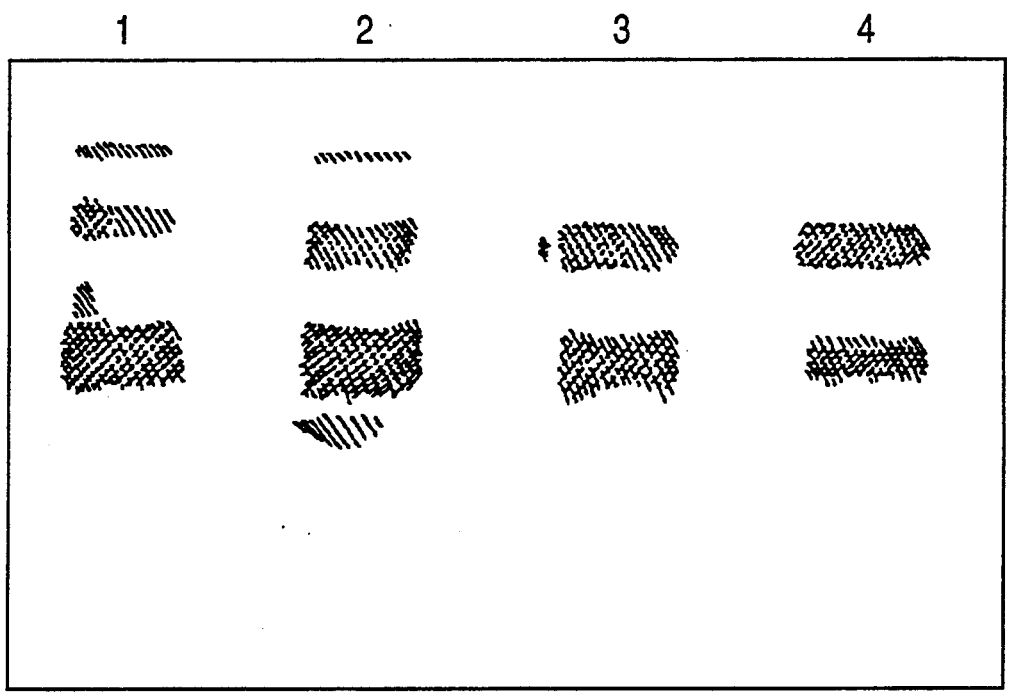
Figure 28B:
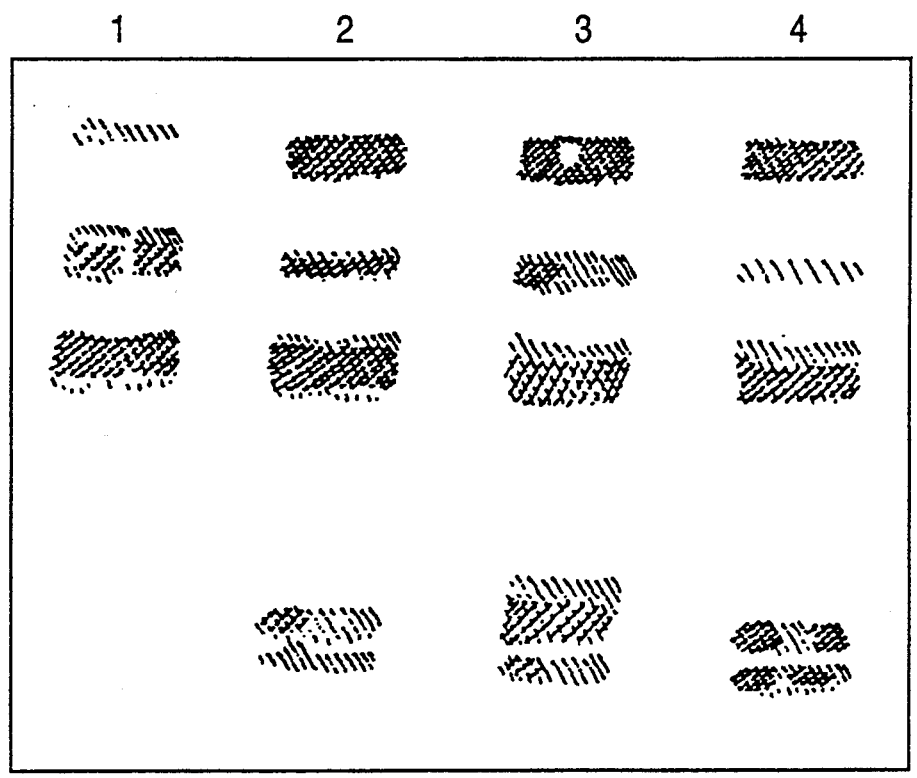

FIG. 28B types of plasminogen activator present in homogenate of a typical colon cancer specimen as shown by fibrin agarose overlay after SDS-PAGE. Lane 1 represents the untreated sample, Lanes 2–4 after 30, 60 and 120 min incubation at 37° with human plasminogen. Zones A–D as for normal colon. Zone E is HPA52 ($M_r$ 52,000) and Zone F is HPA33–35 ($M_r$ 33–35,000).

FIG. 29A

The effect of minactivin on plasminogen activators in a homogenate of a sample histologically normal colon expressing atypical levels of HPA52 activity. Lane 1 shows control treated sample. Lane 2 shows the effect of preincubation for 60 min at 23° with minactivin. Lane 3 represents the effect of preincubation for 30 min at 37° with plasminogen and then for 60 min at 23° with control buffer. In Lane 4 the homogenate was preincubated for 30 min at 37° with plasminogen, and then exposed in minactivin for 60 min at 23°. Zones of lysis are: A—plasmin, $M_r$ 85,000; B—HPA66, $M_r$ 66,000; C—HPA 52, $M_r$ 52,000 and D—HPA33–36, $M_r$ 33–36,000.

FIG. 29B

Figure 29A:
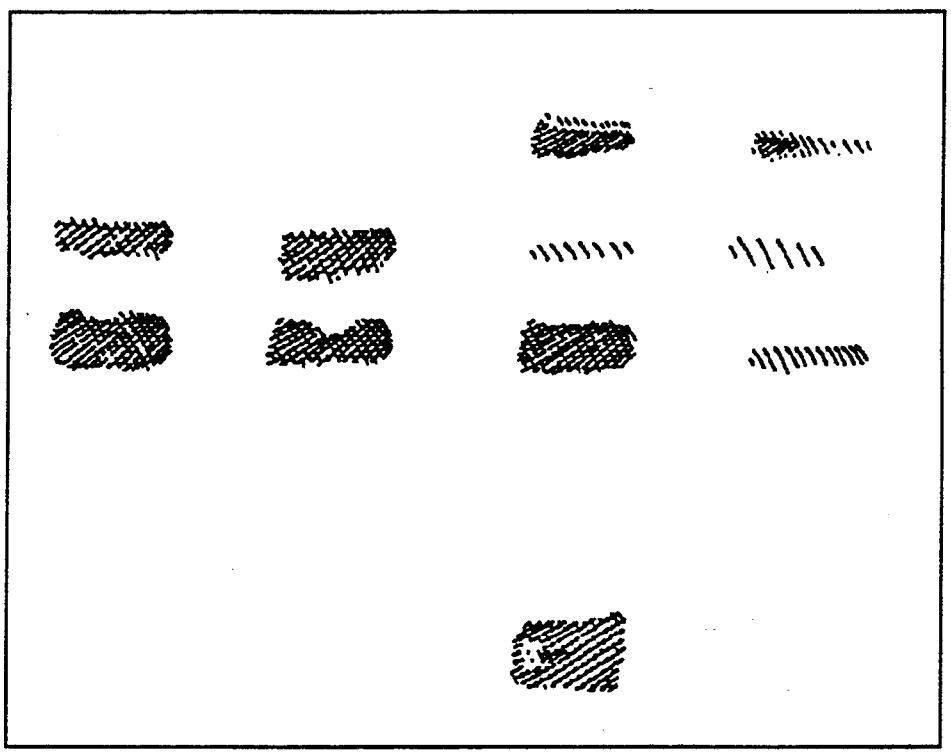

Colon tumour homogenate treated as in FIG. 29A.

FIG. 30

Titration of the colorimetric activity of human urokinase with minactivin. The urokinase was preincubated with minactivin for 90 mins at 23° before dilution to the range suitable for assay. The three curves represent, from left to right, 1000 mPU, 100 mPU and 10 mPU respectively of urokinase.

FIG. 31

Titration of the colorimetric activity of human plasminogen activators from colon cells and tissues with minactivin. The three curves represent, from left to right, an extract of normal mucosa (approx. 0.5 mPU), and extract of colon tumour (approx. 10 mPU). Note that the latter is later known to be proenzyme.

FIG. 32

Effect of minactivin on tumour cell culture plasminogen activator. Lane 1, culture with no additions; Lane 2, with plasminogen Lane 3, with plasminogen and minactivin; Lane 4, with plasminogen, trasylol and minactivin.

FIG. 33

Figure 32:
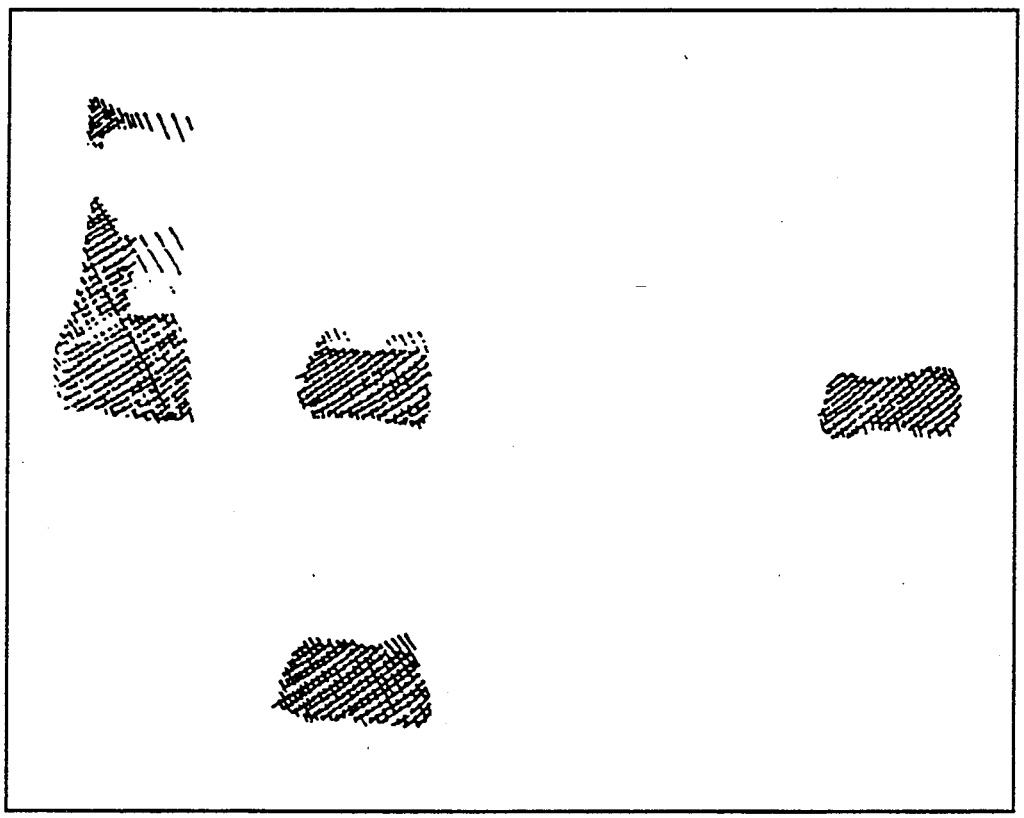

Colorimetric assays of culture supernatants from the same experiment as in FIG. 32.

Figure 34:
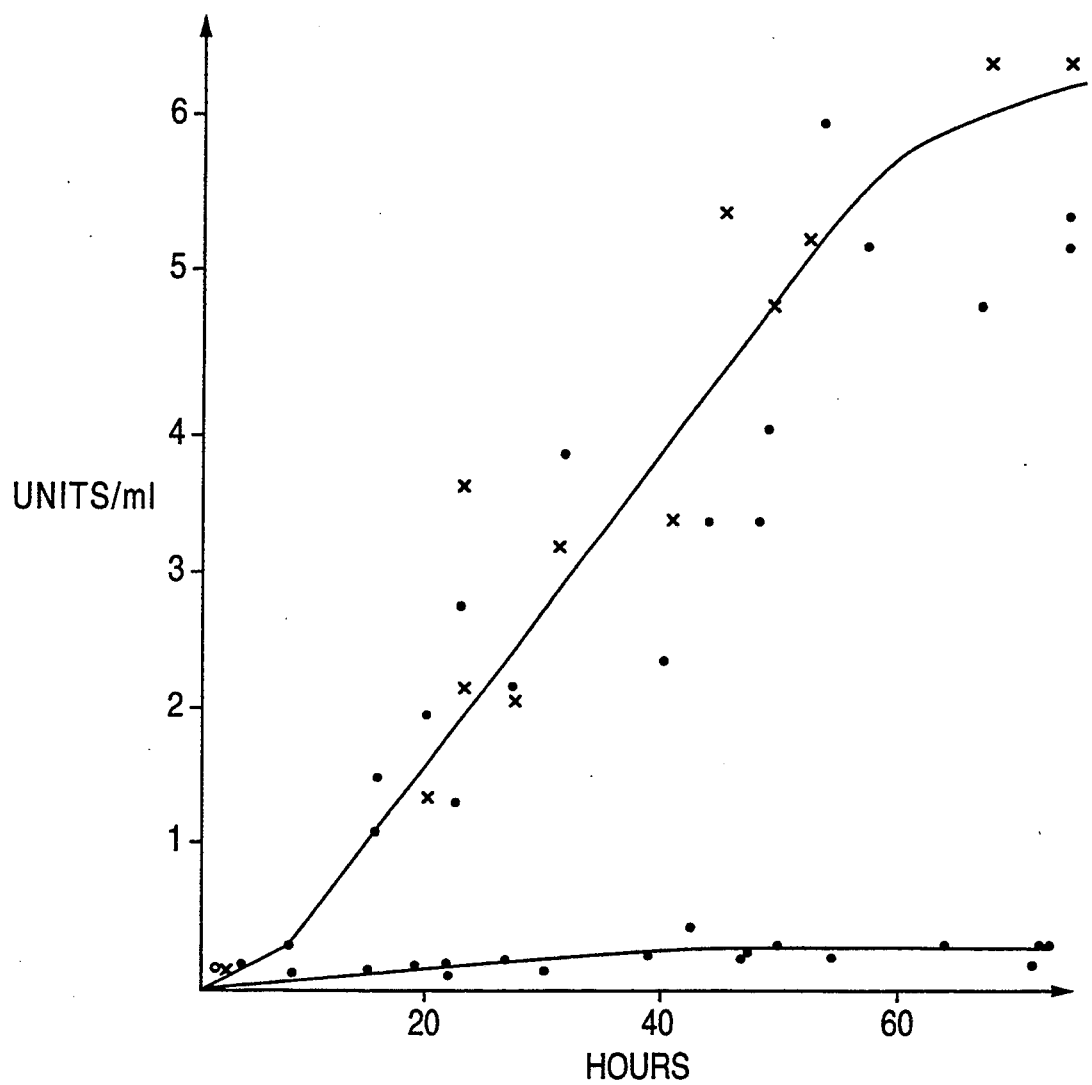

FIG. 34 is a plot of minactivin activity illustrating the effect of PMA on minactivin secretion.

Figure 35:

FIG. 35 is a gel analysis of a size fractionated minactivin mRNA preparation.

Figure 36:
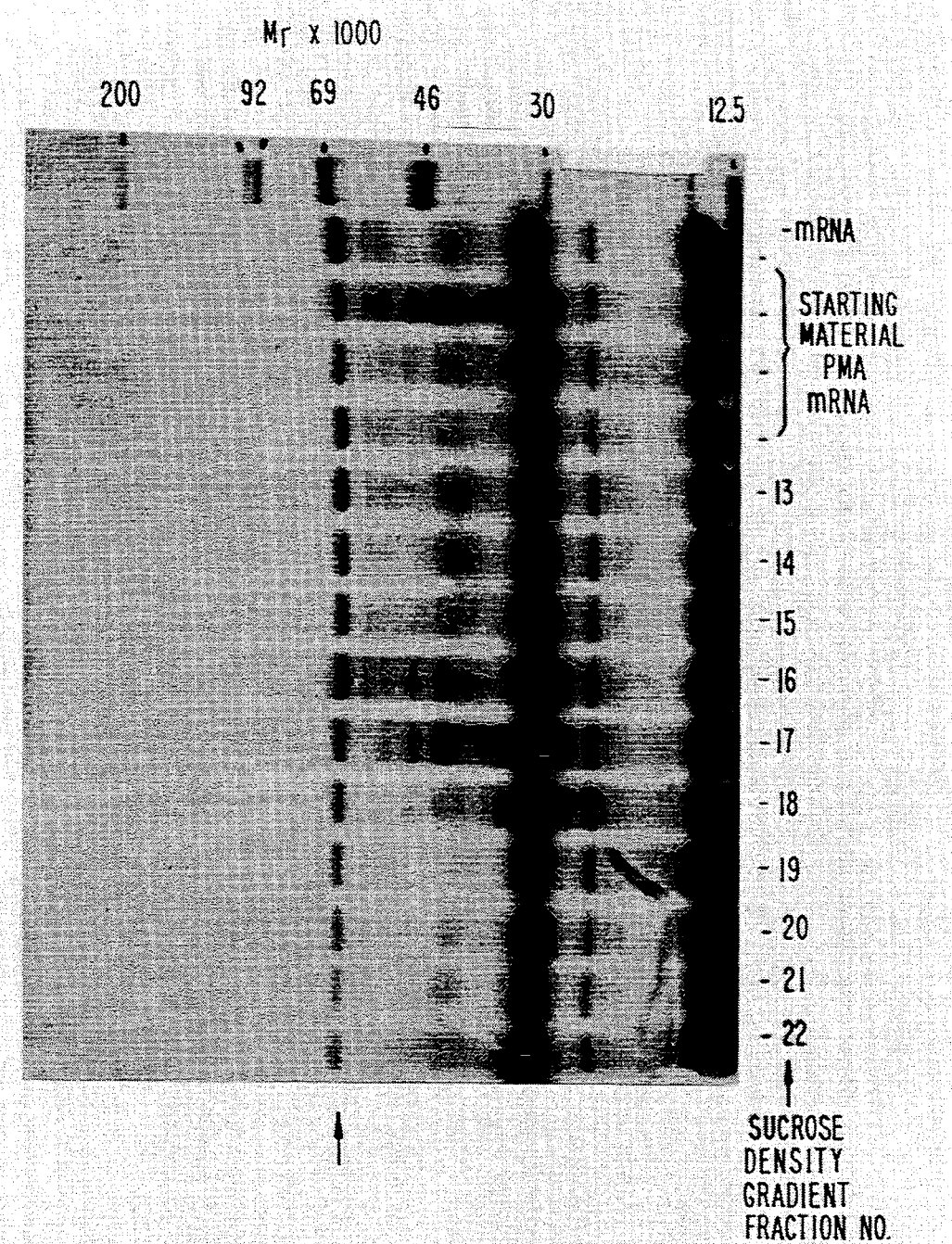

FIG. 36 is an autoradiograph of the immunoprecipitation products following in vitro translation of size fractionated mRNA showing minactivin mRNA in the fractions centred around 18S rRNA standard.

Figure 37:
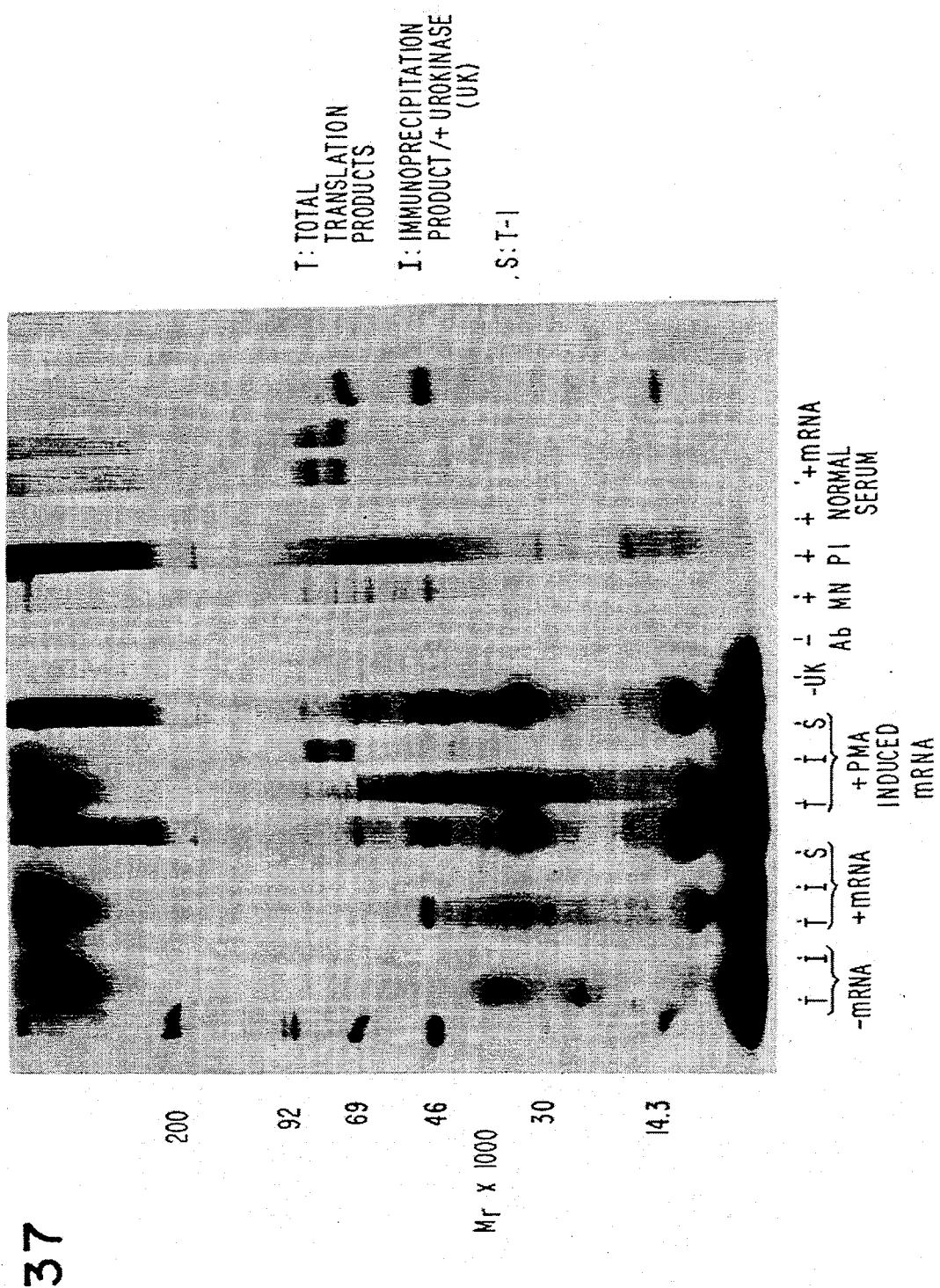

FIG. 37 is an autoradiograph of immunoprecipitated translation products showing the specificity of complex formation with urokinase using anti urokinase antibodies.

Figure 38:
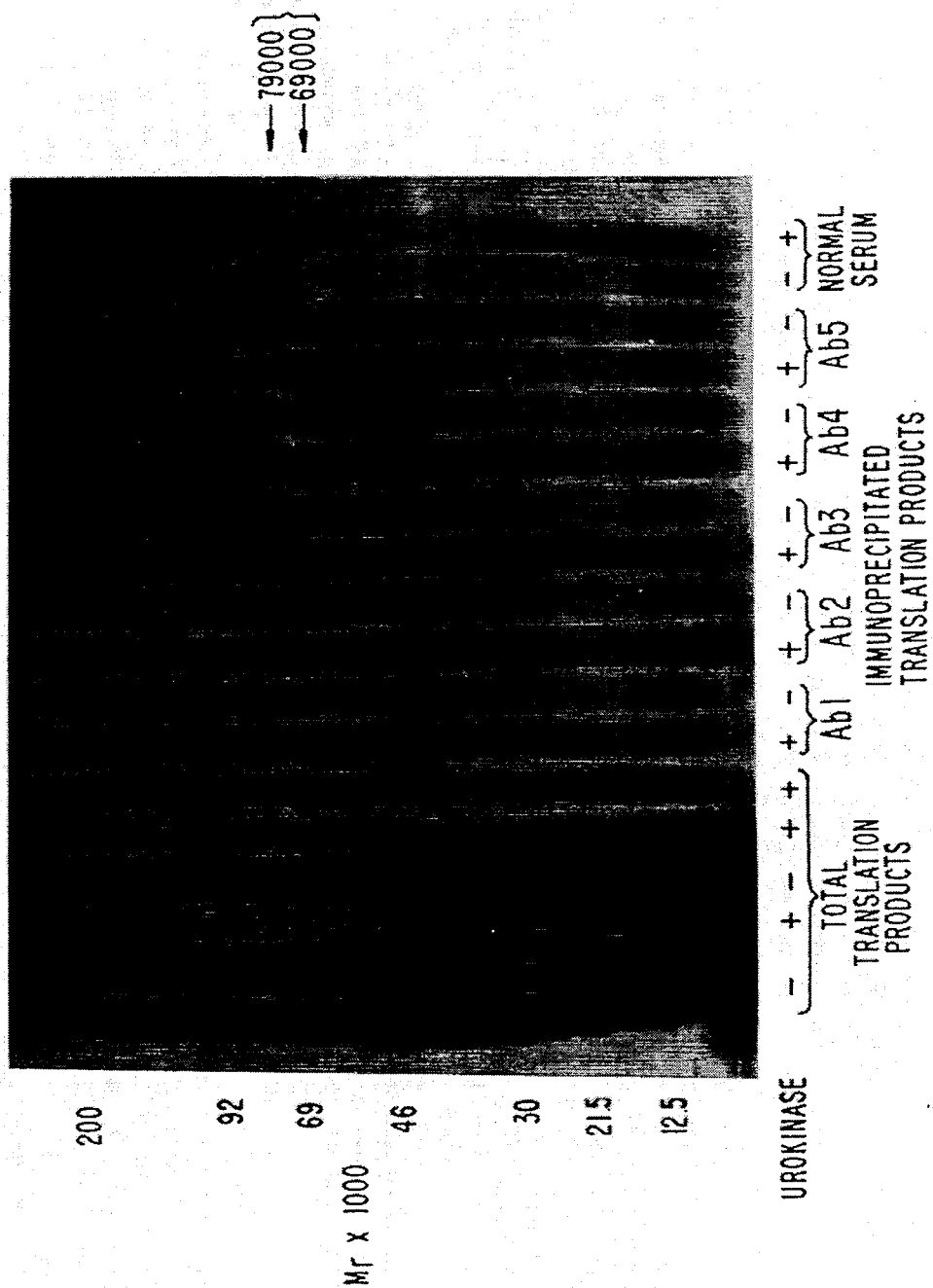

FIG. 38 is an autoradiograph of immunoprecipitated translation products showing the specificity of complex formation with urokinase using anti placental inhibitor antibodies. (autoradiograph showing identity of results using anti placental inhibitor antibodies with results using anti urokinase antibodies).

Figure 39:
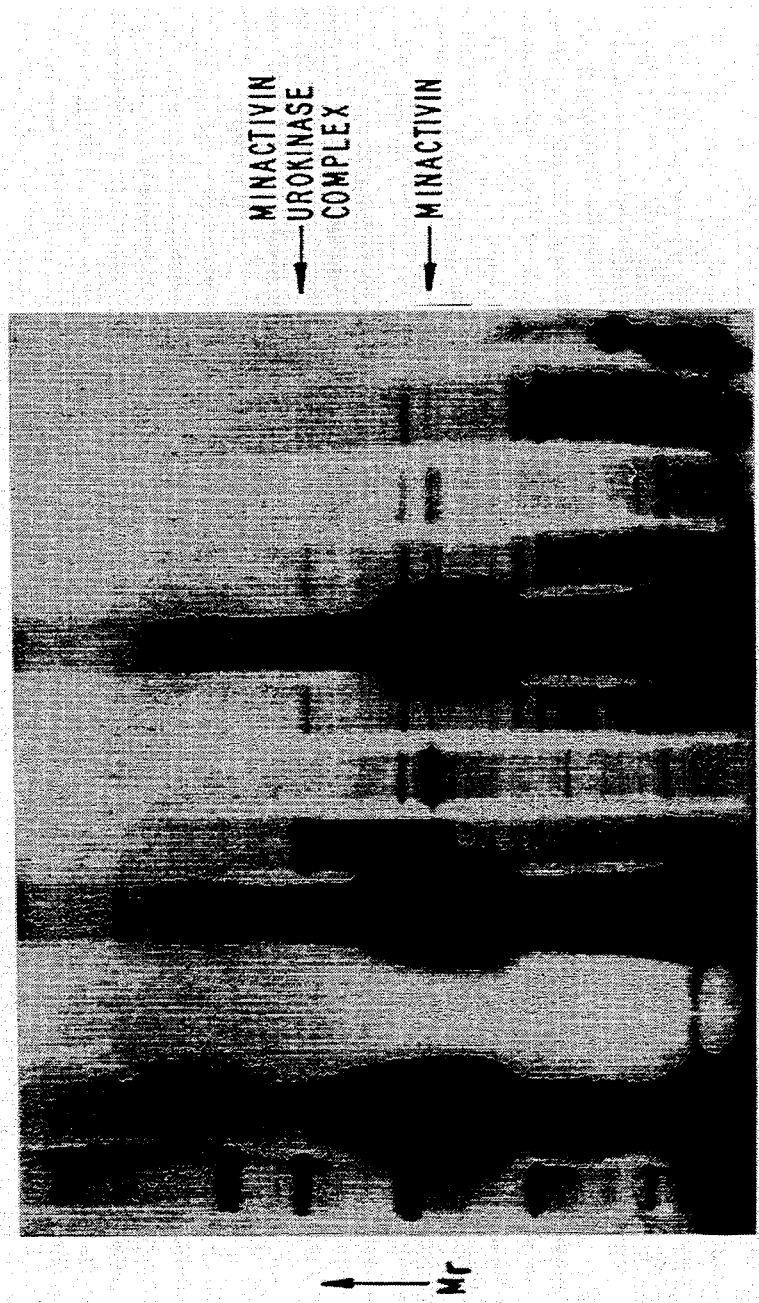

FIG. 39 is an autoradiograph showing identification of the minactivin translation product by comparison of immunoprecipitation products in the presence and absence of urokinase under reducing conditions.

FIG. 40 is a representation of a gel showing differentiation of urokinase species using the fibrin overlay technique.

Figure 41:
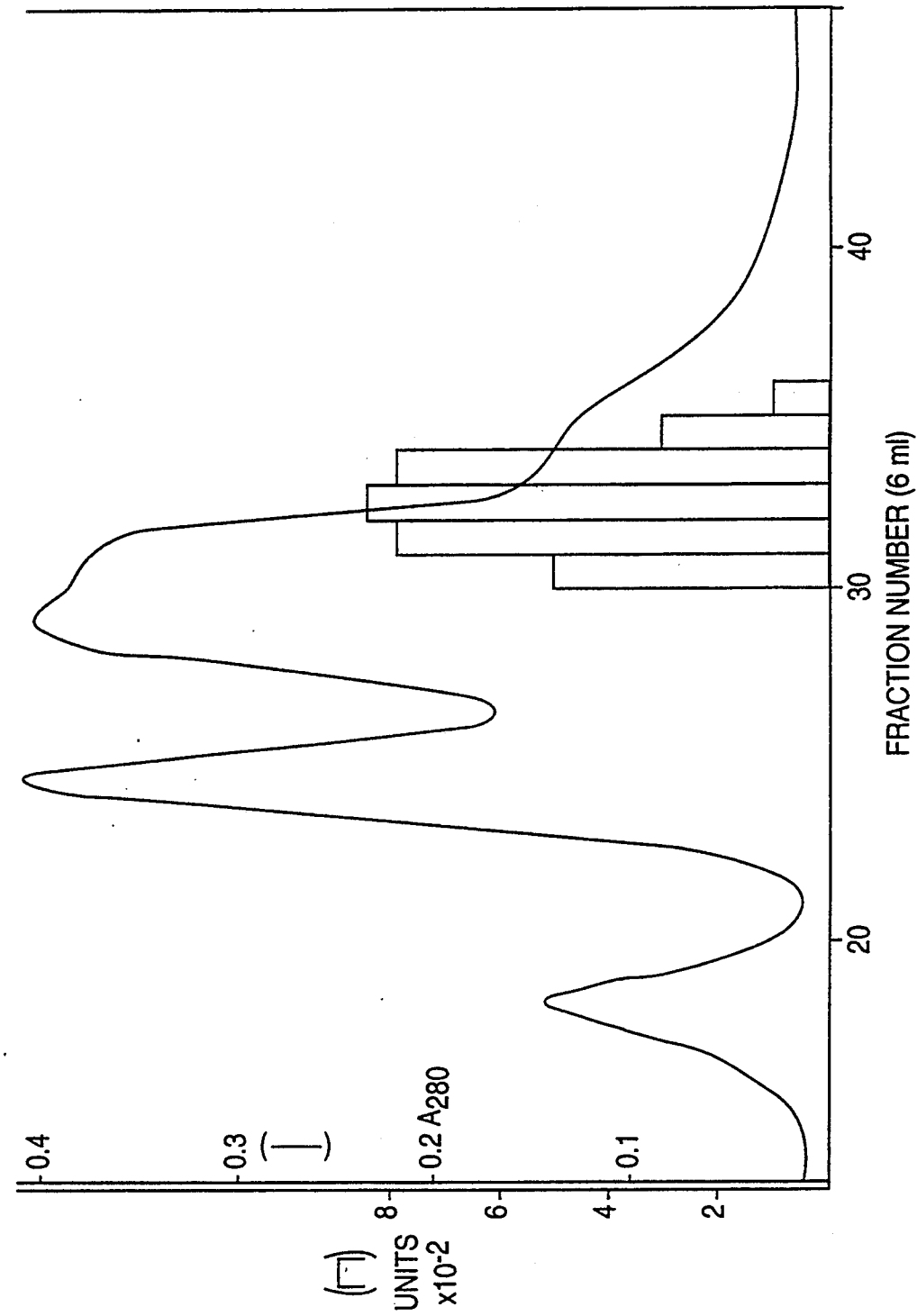

FIG. 41 is a Sephacryl S-200 chromatogram showing elution of enriched minactivin activity relative to total protein elution.

Figure 42:
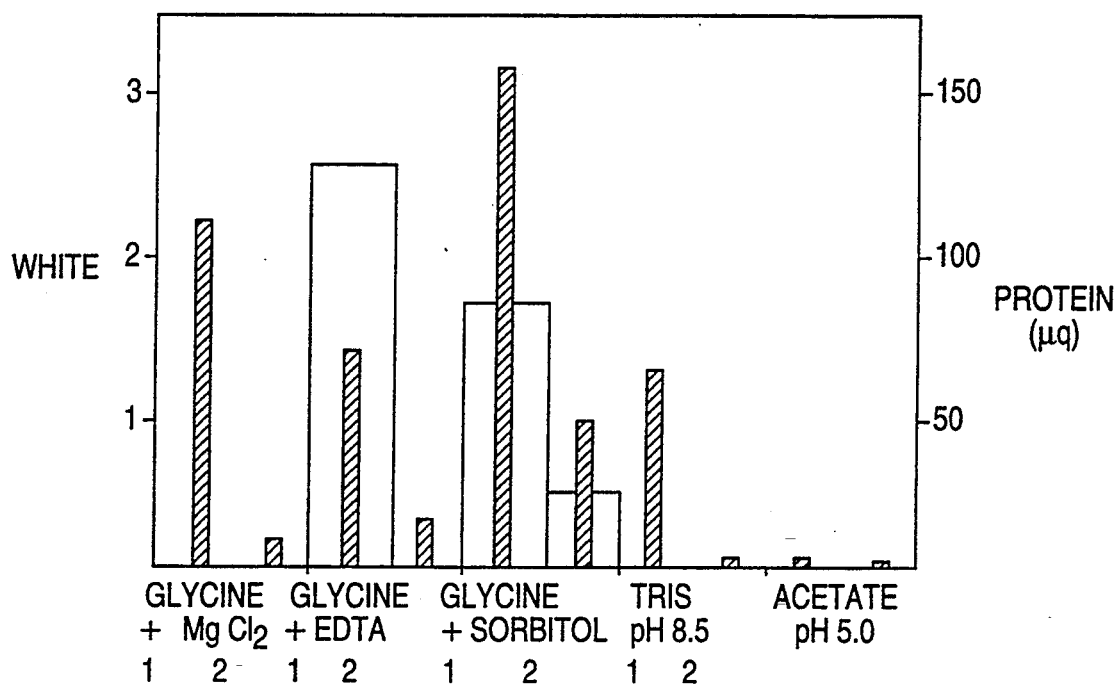

FIG. 42 is a plot showing differential elution of minactivin activity from phenyl-boronate agarose under varied elution conditions.

Figure 43:
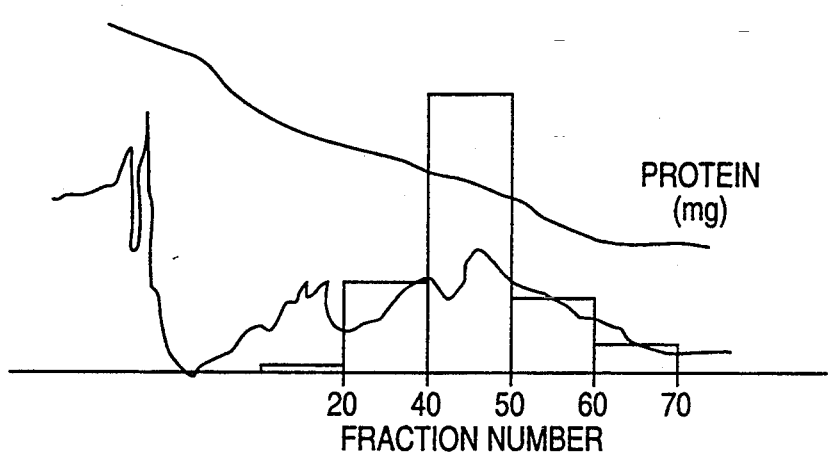

FIG. 43 is a chromatograph showing elution of minactivin activity relative to total protein eluted from a chromofocussing column as a function of pH of elution.

Figure 44:
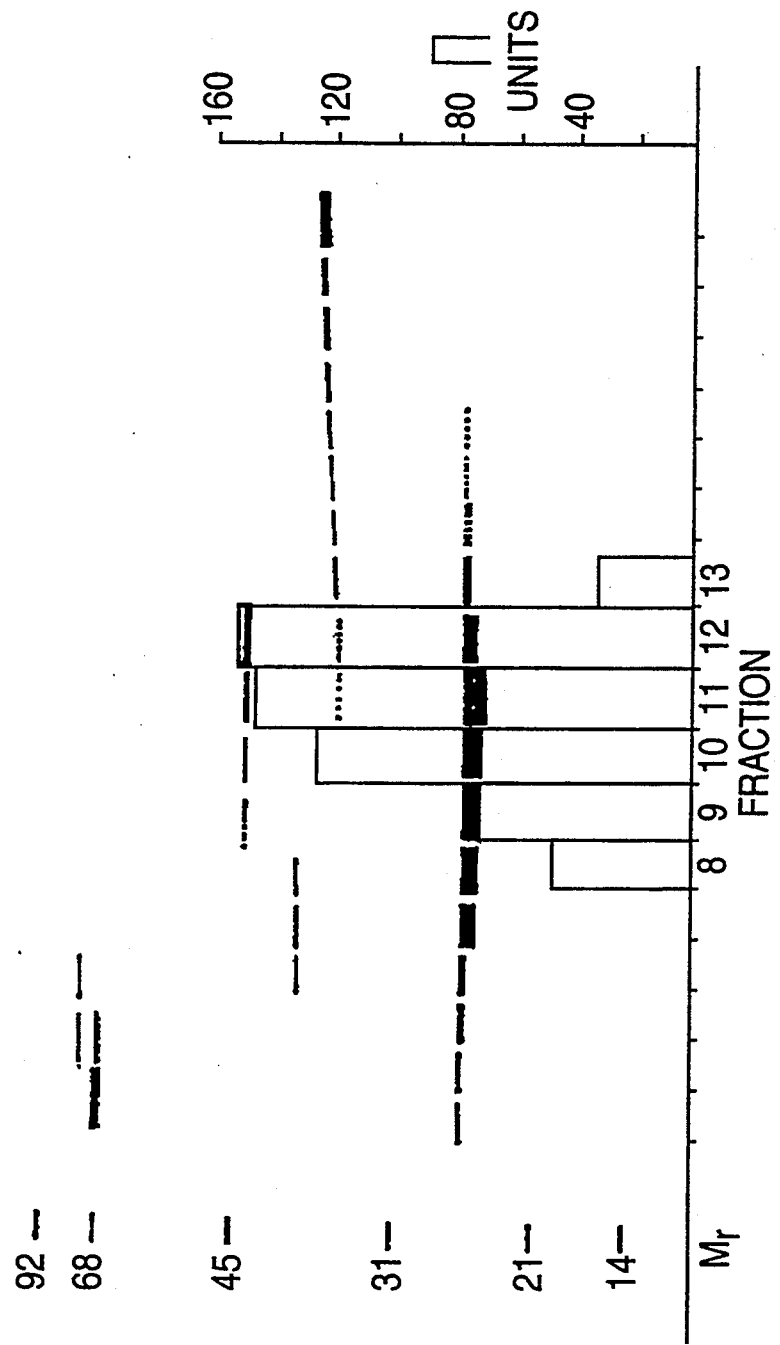

FIG. 44 is a superimposition showing minactivin activity over a gel of the protein fractions isolated from an isoelectrofocussing gel to demonstrate protein content versus minactivin activity.

Figure 45A:
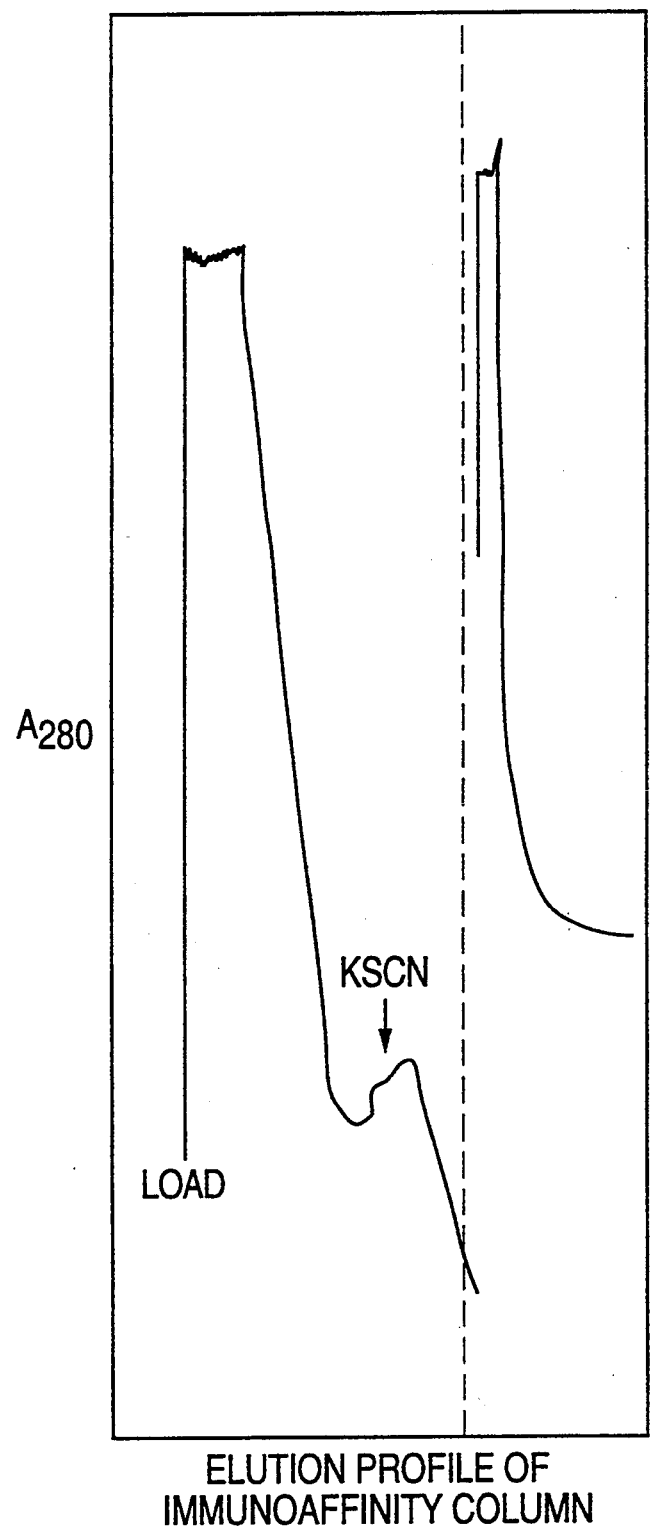

FIG. 45A is an elution profile of an immunoaffinity column showing elution of minactivin activity.

Figure 45C:
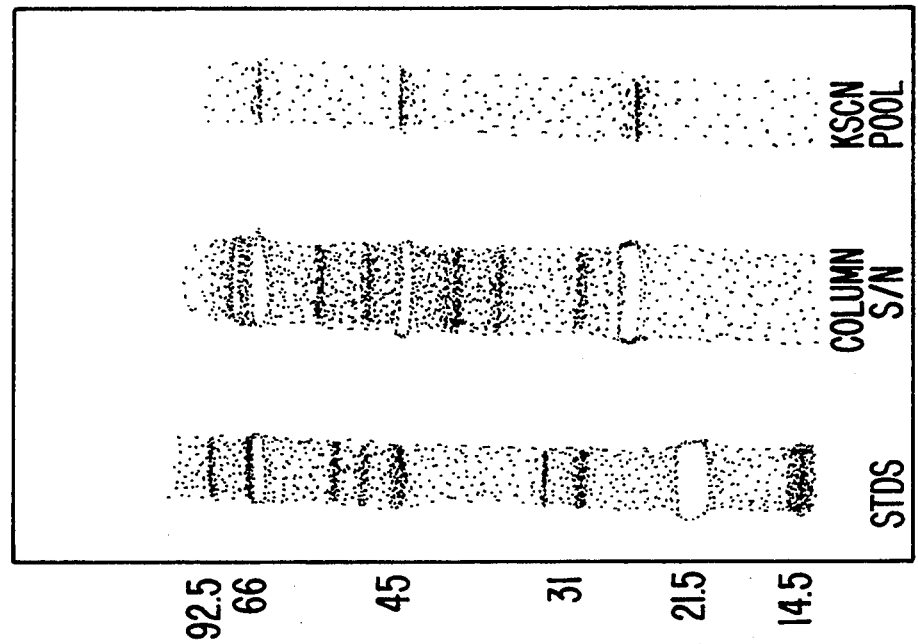
Figure 45B:
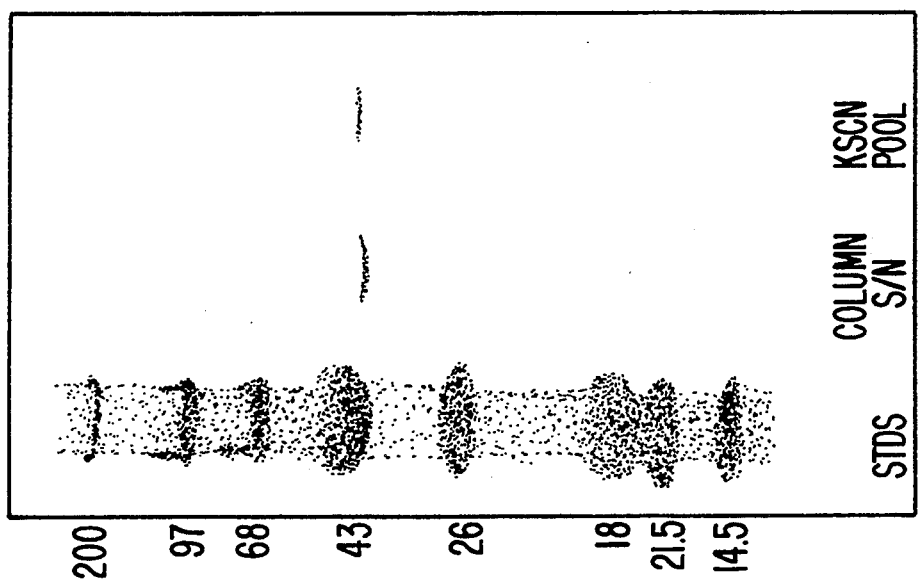

FIGS. 45B and 45C are representations of an SDS-PAGE gel of minactivin eluted from the immunoaffinity column and a Western blot of this gel.

FIG. 46 is an autoradiograph of $I^{125}$-labelled urokinase on SDS-PAGE showing high and low molecular weight forms and dissociation of high molecular weight form under reducing conditions.

Figure 47:
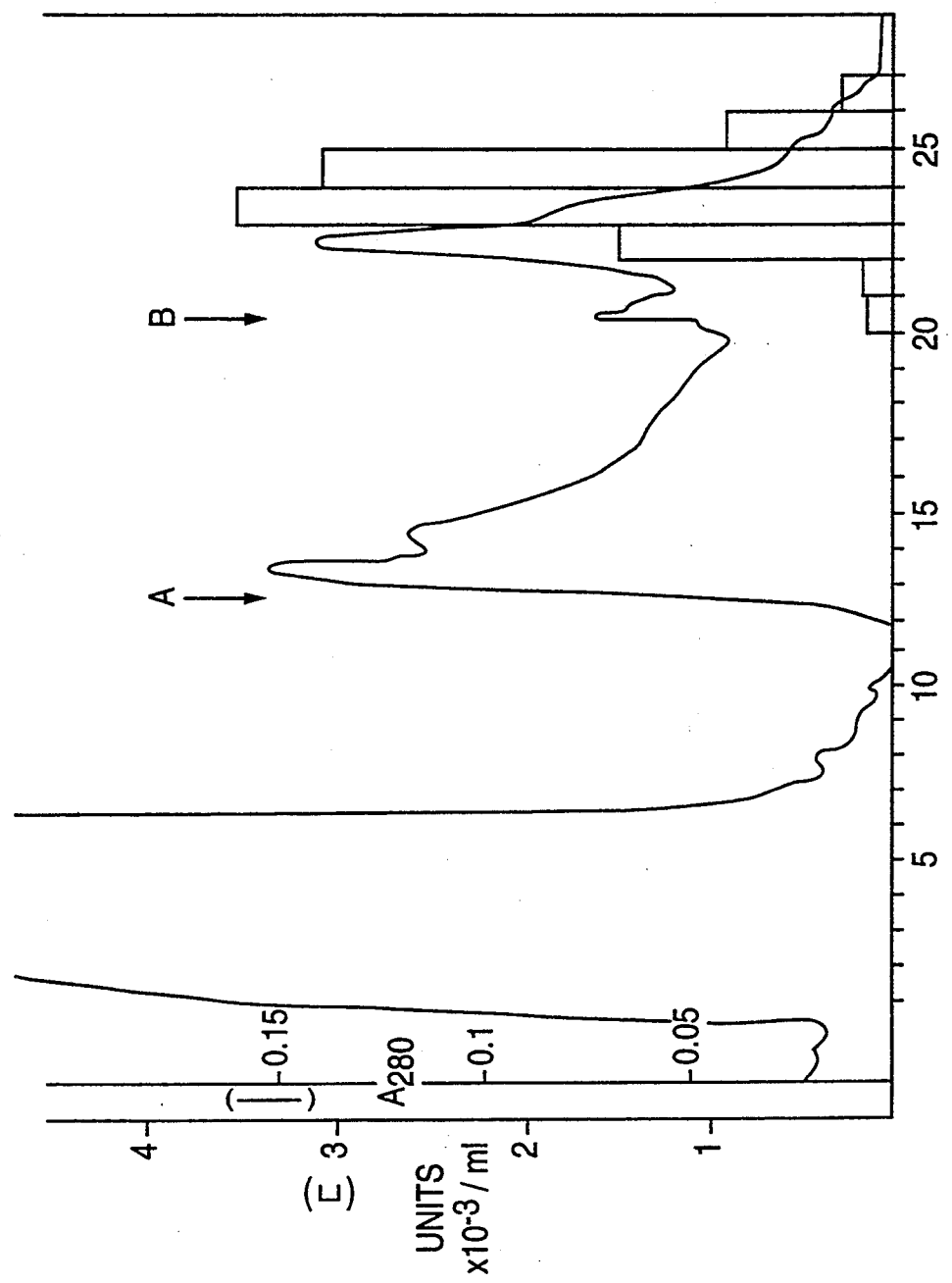

FIG. 47 shows the elution profile of minactivin activity and protein from the step pH elution of the phenyl-sepharose column.

A:elution with 50 mM sodium citrate, pH5.5, 1 mMEDTA, 0.5M sodium chloride.

B:elution with 50 mM glycine, pH9.0.

Figure 48:
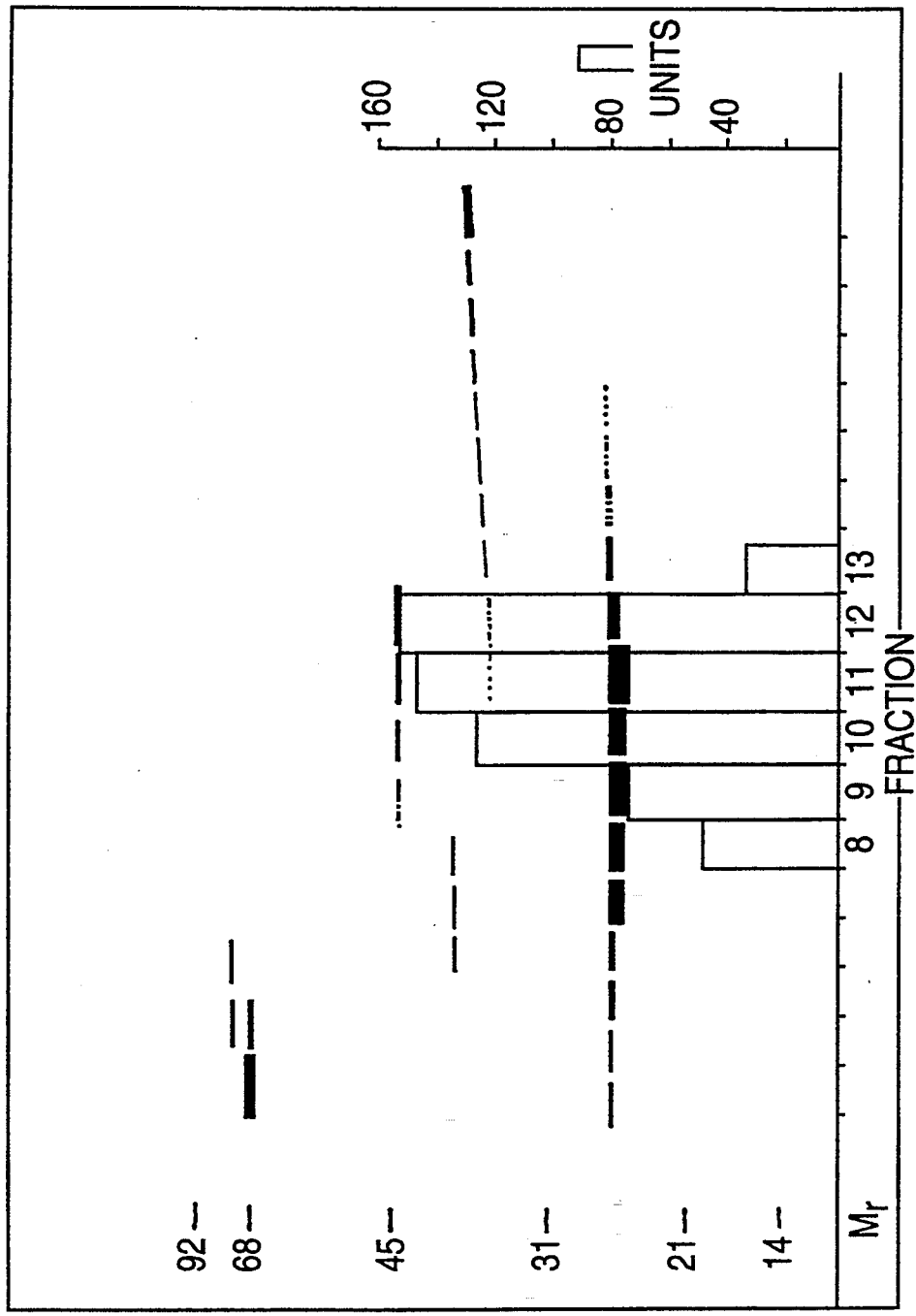

FIG. 48 is a superimposition of minactivin activity over an SDS-PAGE gel of the protein fractions isolated from an isoelectric focussing gel to demonstrate protein content versus minactivin activity.

Figure 49:
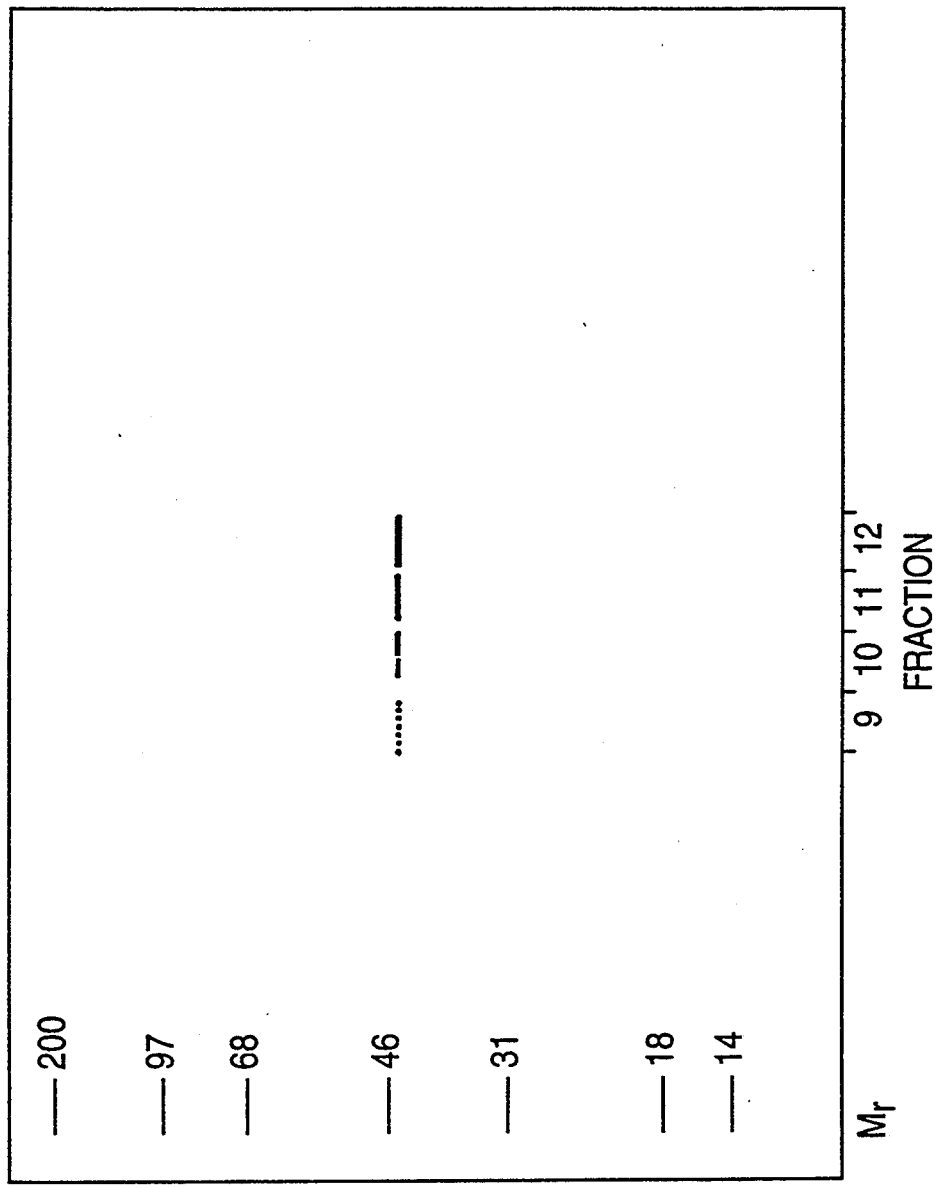

FIG. 49 is a representation of the fractions from the isoelectric focussing experiment shown in FIG. 48 after Western transfer of the protein onto nitrocellulose and immunological detection of the proteins with anti-placental inhibitor antibodies.

Figure 50:
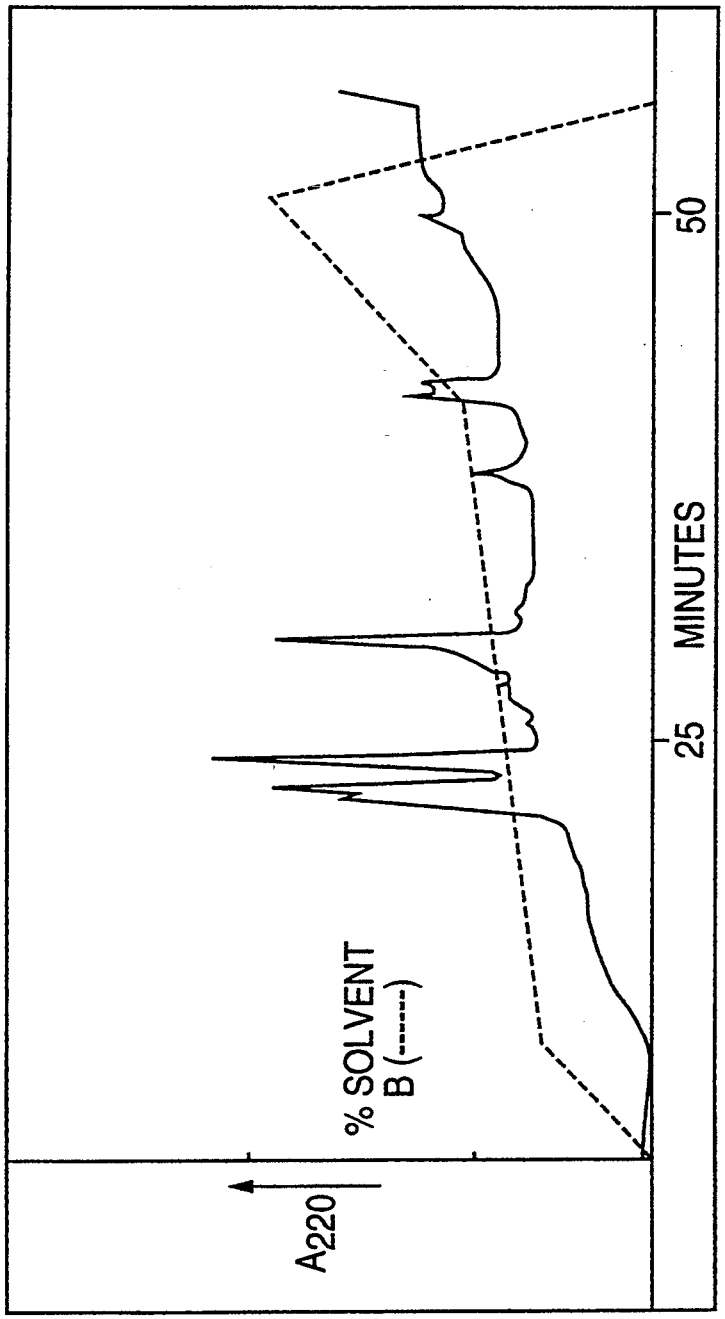

FIG. 50 shows an elution profile of the highly purified minactivin preparation from a Vydac C-4 reverse phase high pressure liquid chromatography run.

Figure 51:
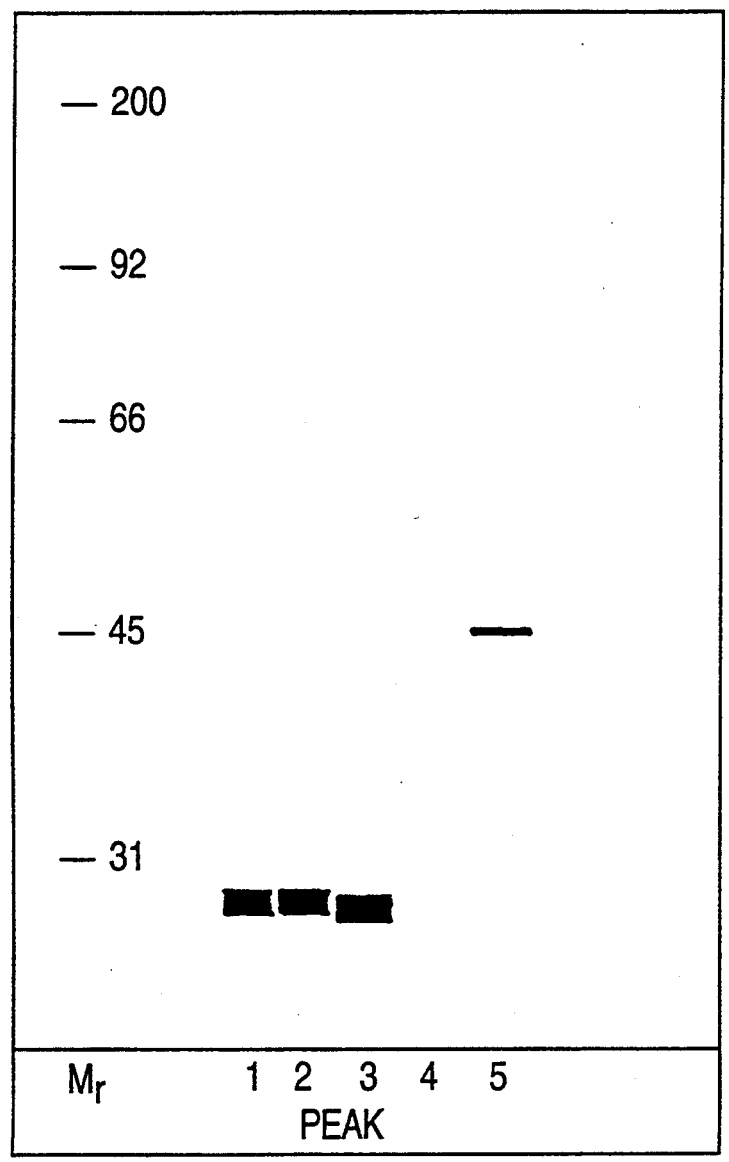

FIG. 51 is a representation of an SDS-PAGE showing homogeneous minactivin obtained from peak 5 of the HPLC run shown in FIG. 50.

Figure 52:
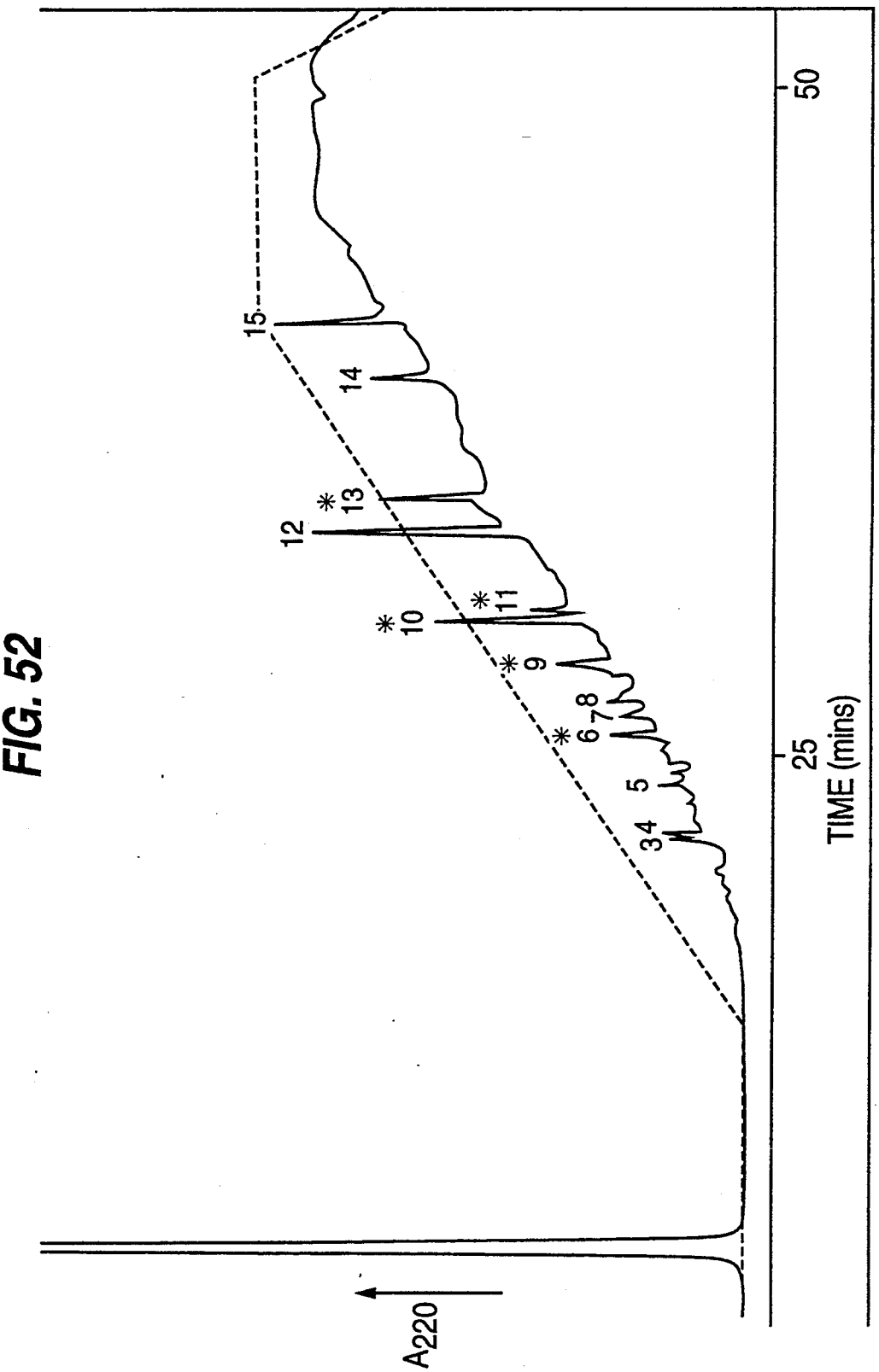

FIG. 52 shows the elution profile of peptides of minactivin eluted form a Synchropak RP-P (C-8) column high pressure liquid chromatography run.

Figure 53:
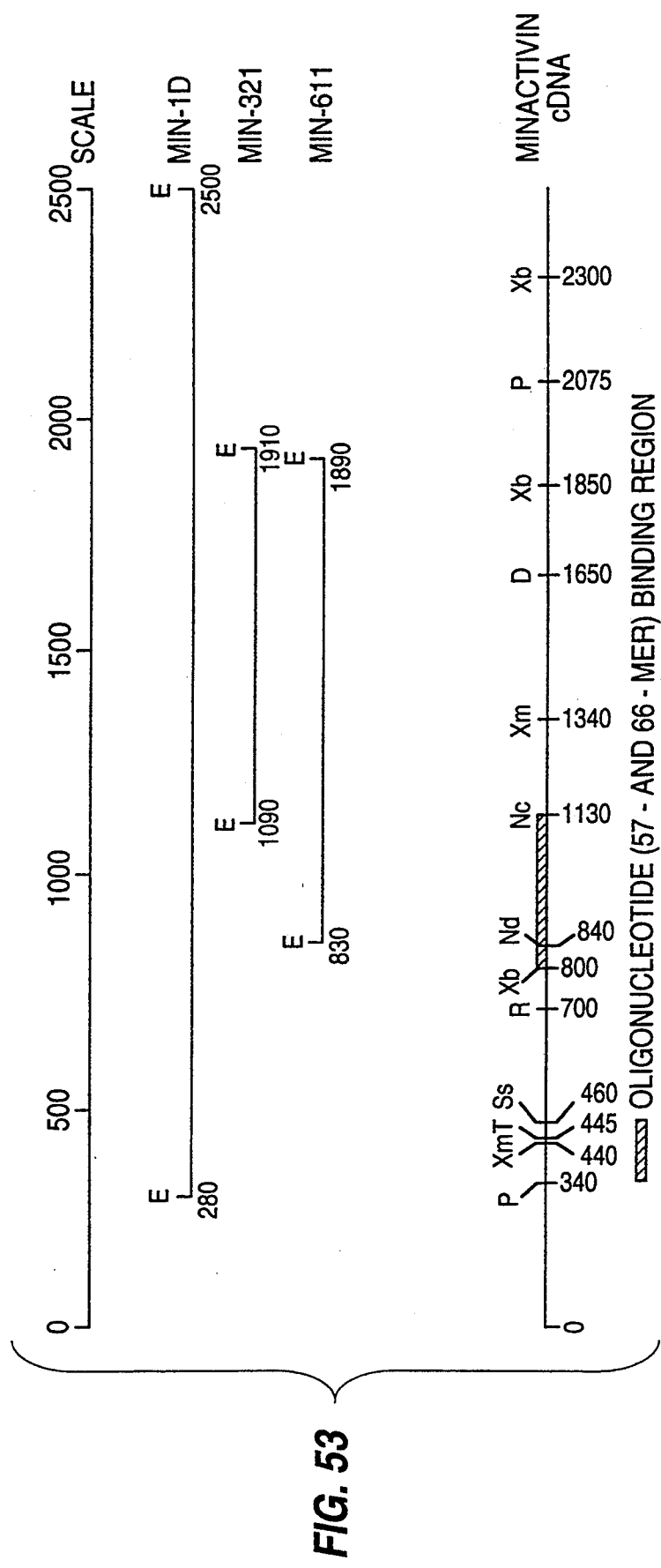

FIG. 53 depicts the endonuclease restriction map and DNA sequencing strategy of the clones containing segments of the minactivin gene.

Figure 54:
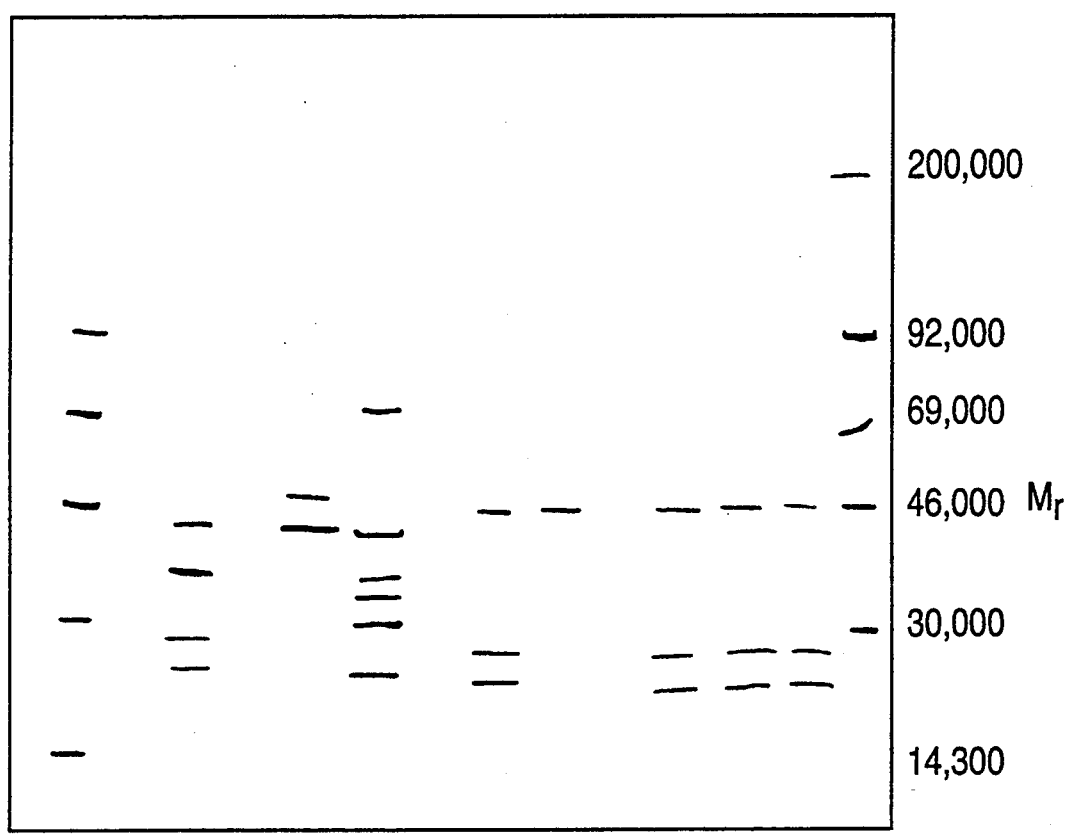

FIG. 54 shows hybrid select translation of minactivin mRNA.

Figure 55:
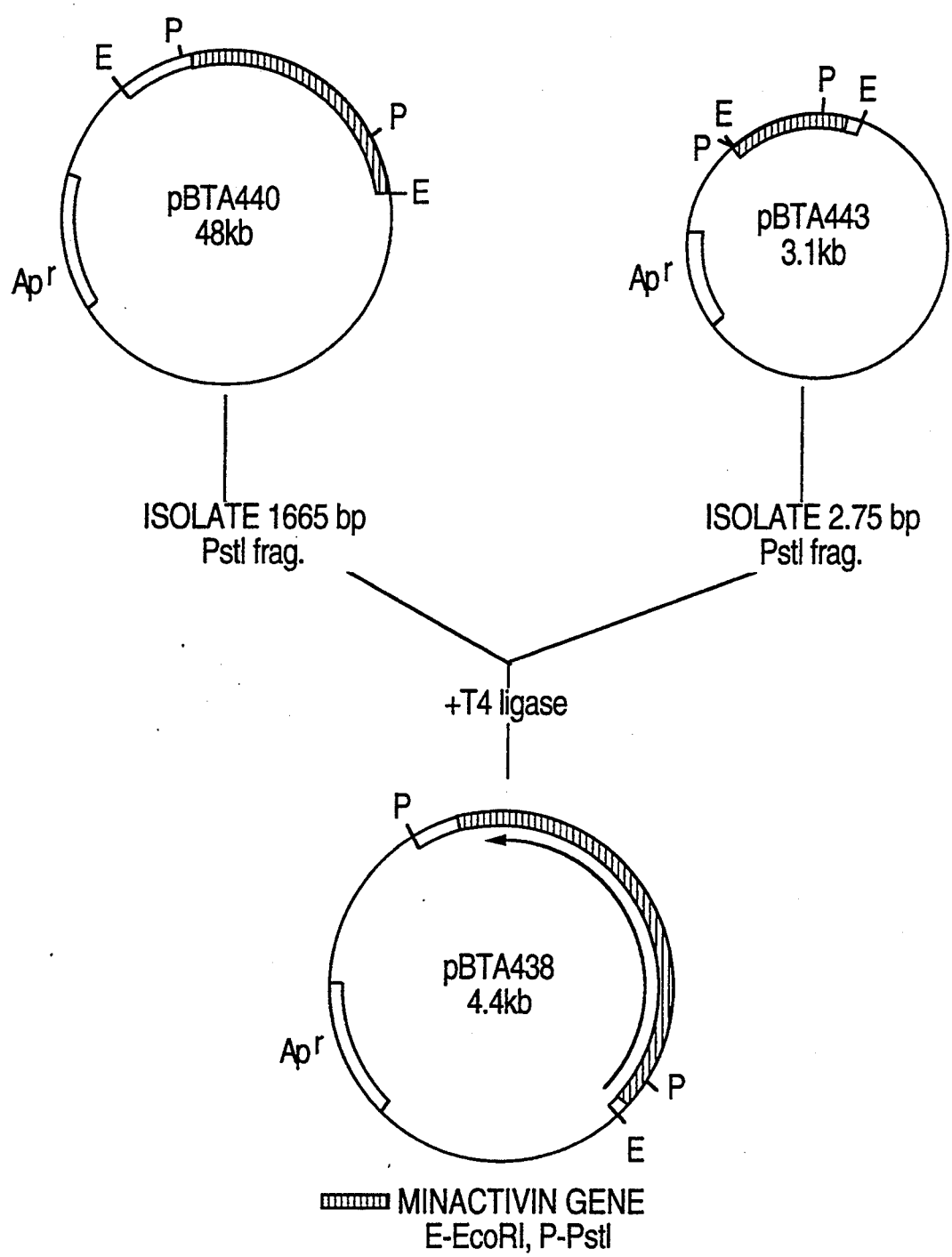

FIG. 55 shows the construction of the plasmid pBTA438 containing the contiguous minactivin gene.

Figure 56A:
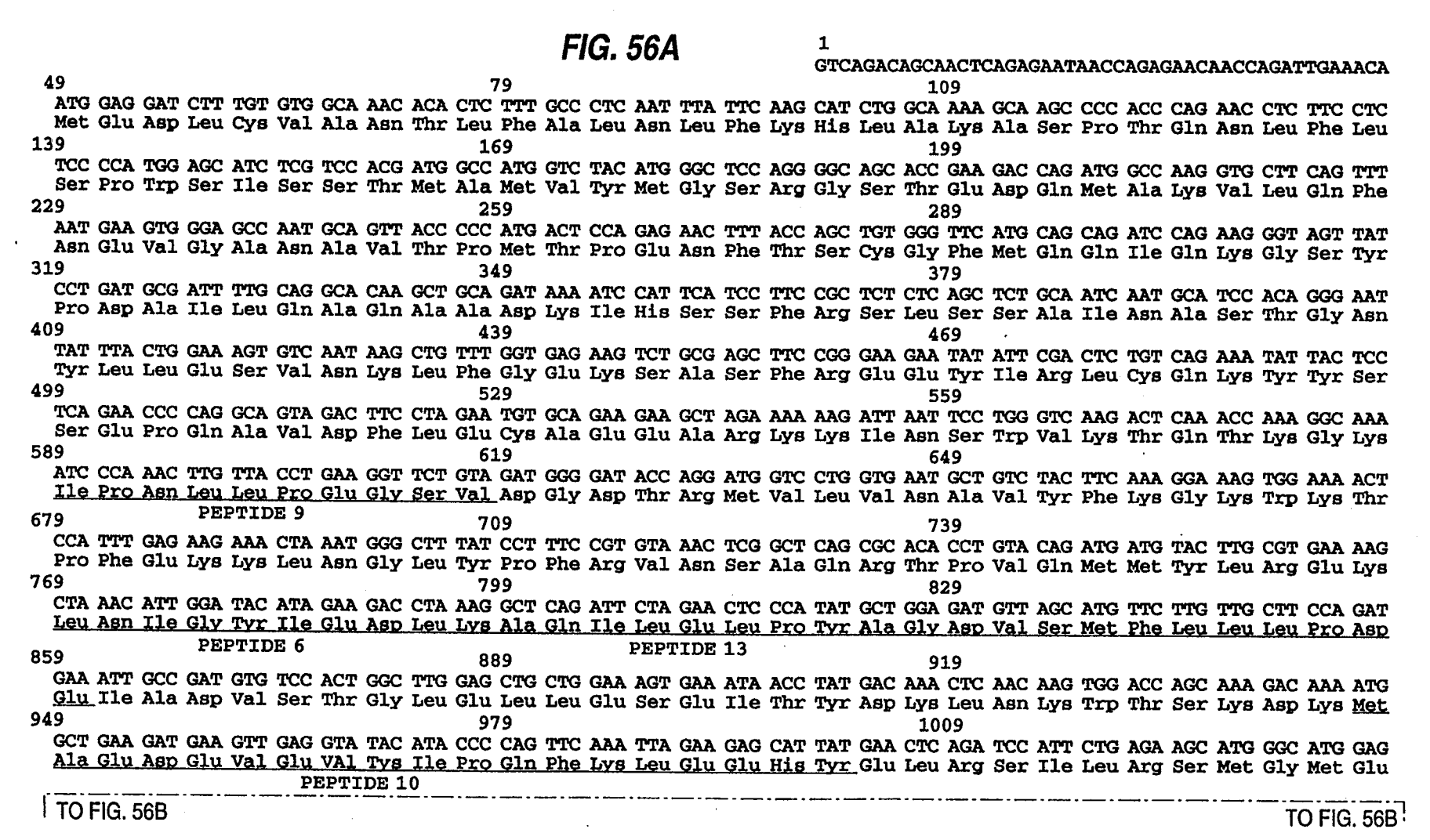

FIGS. 56A and 56B shows the complete cDNA (SEQ ID NO:18) of the minactivin gene and the deduced amino acid sequence (SEQ ID NO:19) of the minactivin protein. The 5 peptides (set forth in SEQ. ID. NOs. 1, 2, 3, 4 and 5, respectively) obtained from the amino acid sequence analysis are underlined.

Figure 57:
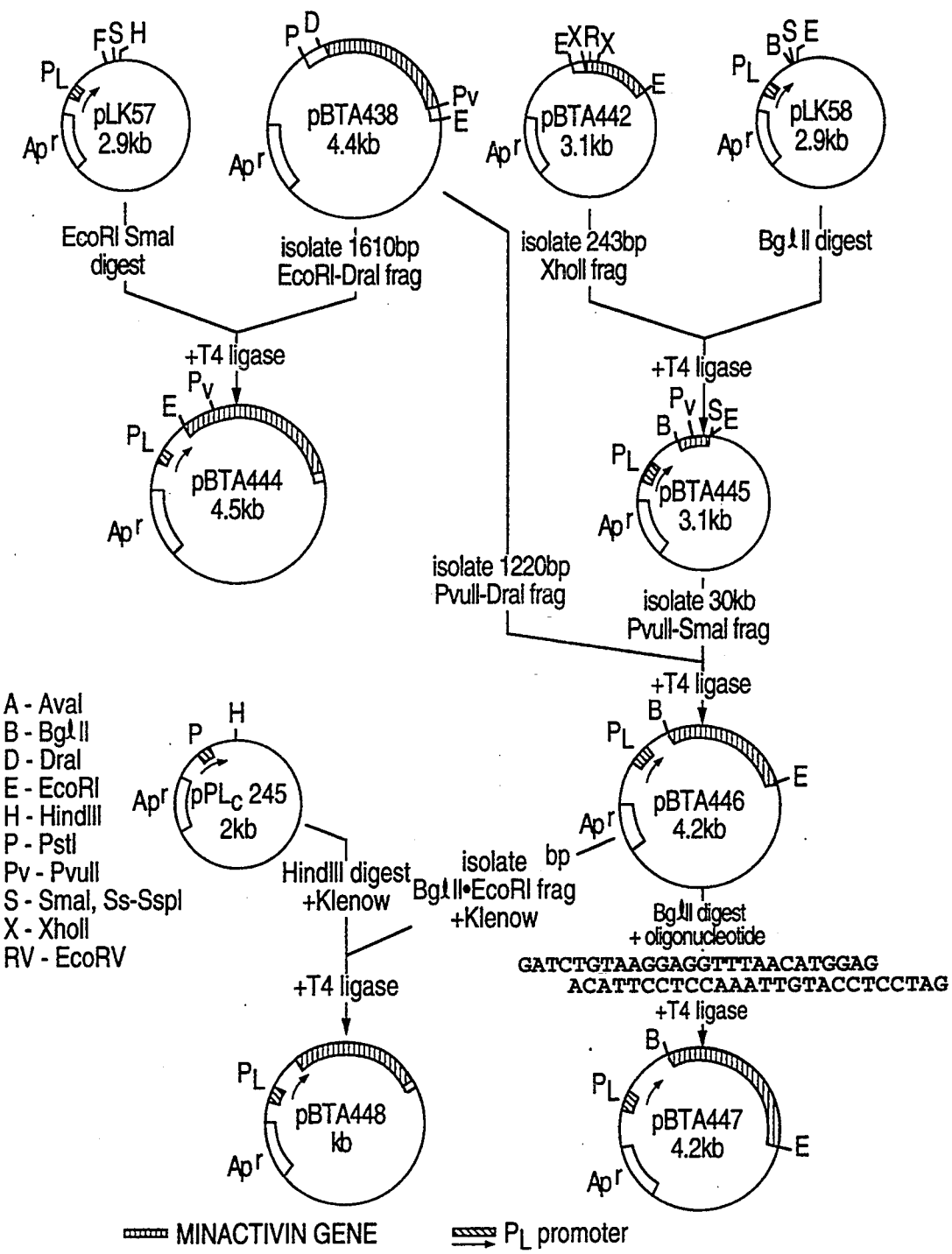

FIG. 57 shows the construction of minactivin expression vectors pBTA444 and pBTA447.

FIG. 58 shows the SDS polyacrylamide gel electrophoresis, Western analysis and $S^{35}$ pulse labelled protein analysis of minactivin expressed from pBTA444, and pBTA447.

Figure 59A:
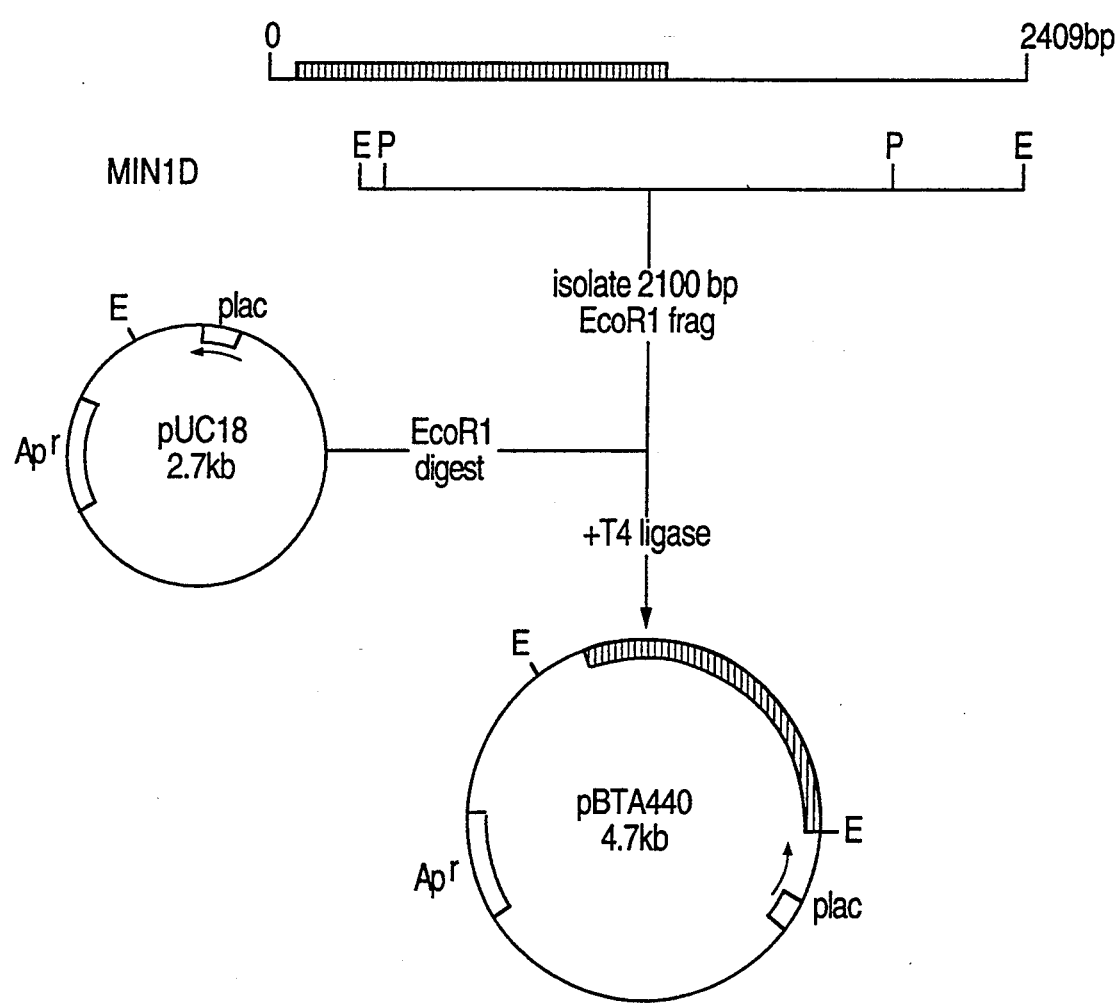
Figure 59B:
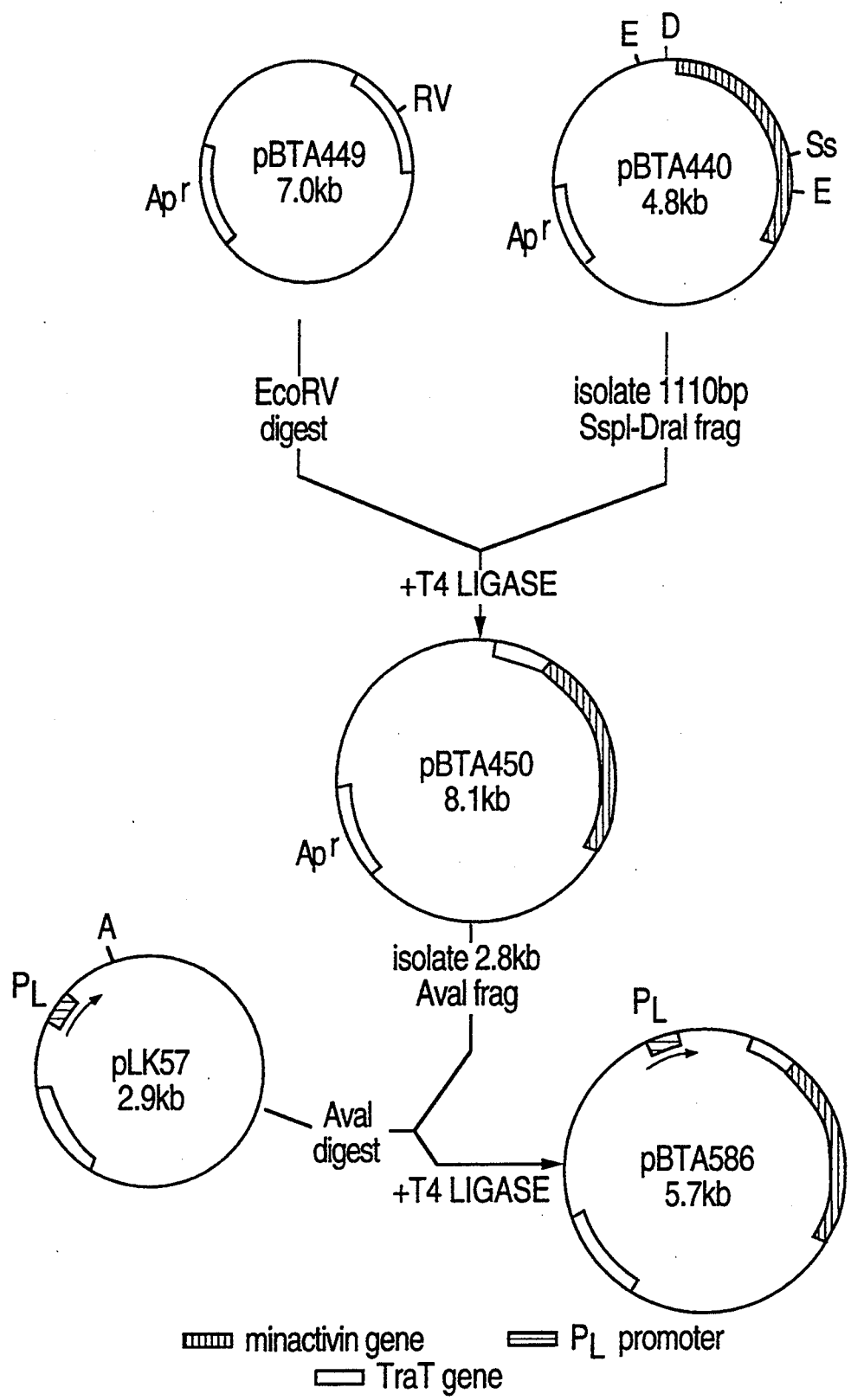

FIGS. 59A and 59B show the construction of hybrid protein expression vectors a) pBTA440 and b) pBTA586.

Figure 60:
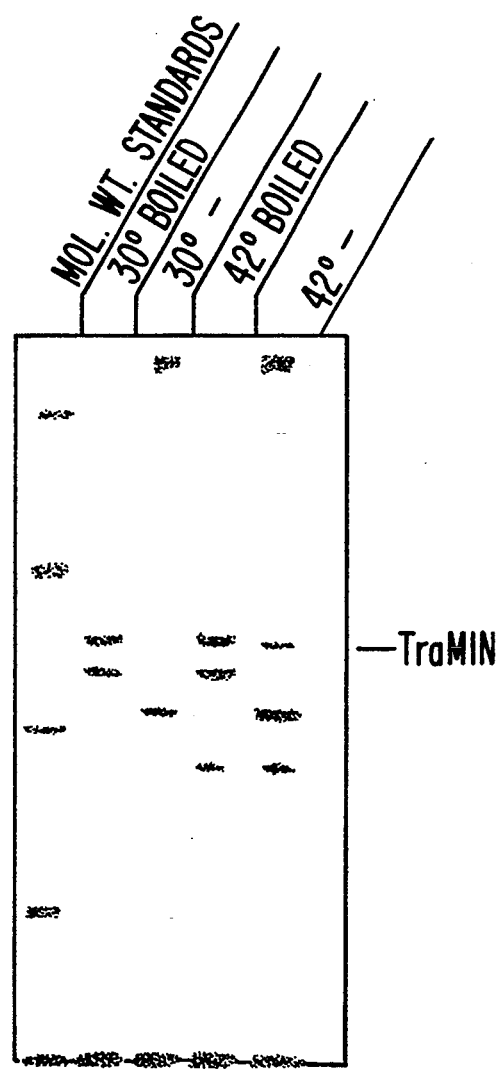

FIG. 60 shows the SDS polyacrylamide gel electrophoresis Western analysis and $S^{35}$ pulsed labelled protein analysis of hybrid minactivin proteins expressed from pBTA440 and pBTA586.

Figure 61:
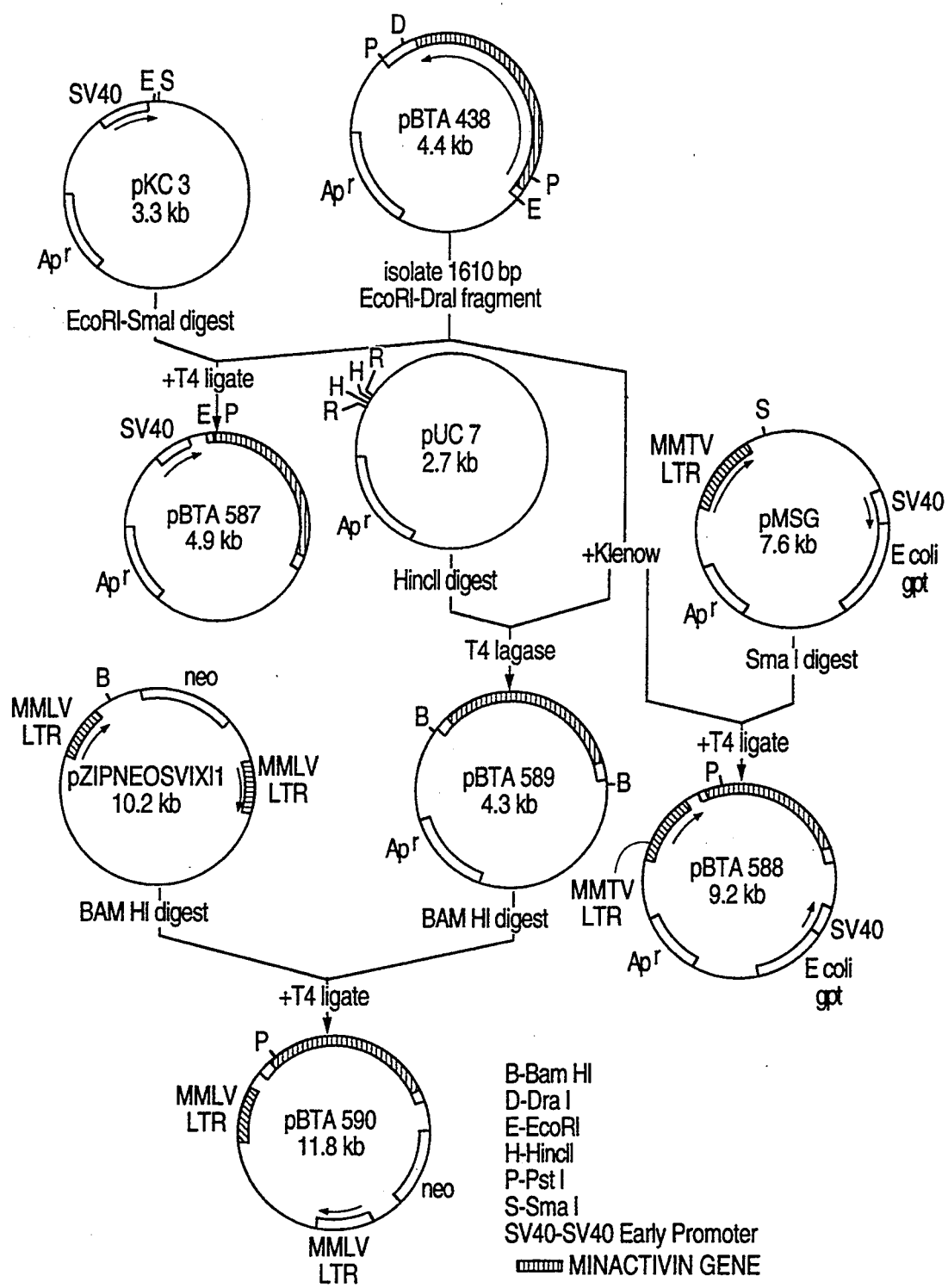

FIG. 61 shows the construction of mammalian cloning vectors pBTA587, pBTA588 and pBTA590 containing the minactivin gene.

Figure 62:
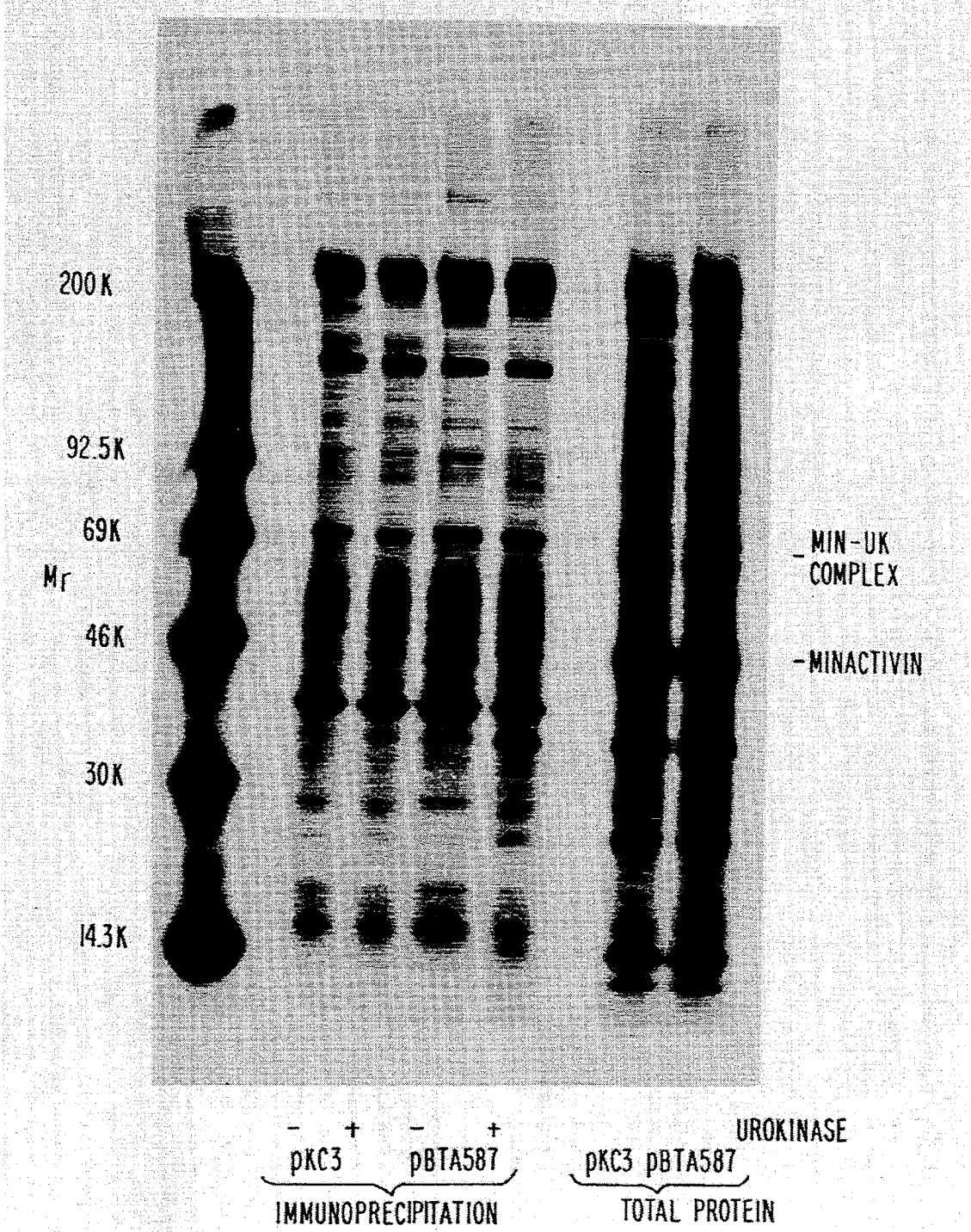

FIG. 62 is an autoradiograph showing expression of minactivin in mammalian cells following immunoprecipitation in the presence and absence of urokinase.

GENERAL PROPERTIES OF MINACTIVIN

Minactivin is heat labile above a temperature of 56° C. but is stable to freezing at −20° C. and thawing (0–5% of its activity is lost after one cycle). Minactivin containing supernatants collected under sterile conditions can be stored at 4° in the presence of gentamicin for two months without significant loss of activity.

The interaction of minactivin with plasminogen activator does not appear to be ionic strength dependent, although ionic strength does have an inverse effect on plasminogen activation (19). While the activity of urokinase in the colorimetric assay was strongly inhibited by increasing salt concentration, the effect of minactivin on the diminished urokinase activity was proportionally the same.

Minactivin is relatively stable in the pH range 5 to 9 at 4° C. Propanol and methanol (greater than 10%) completely abolish minactivin activity.

Figure 10:
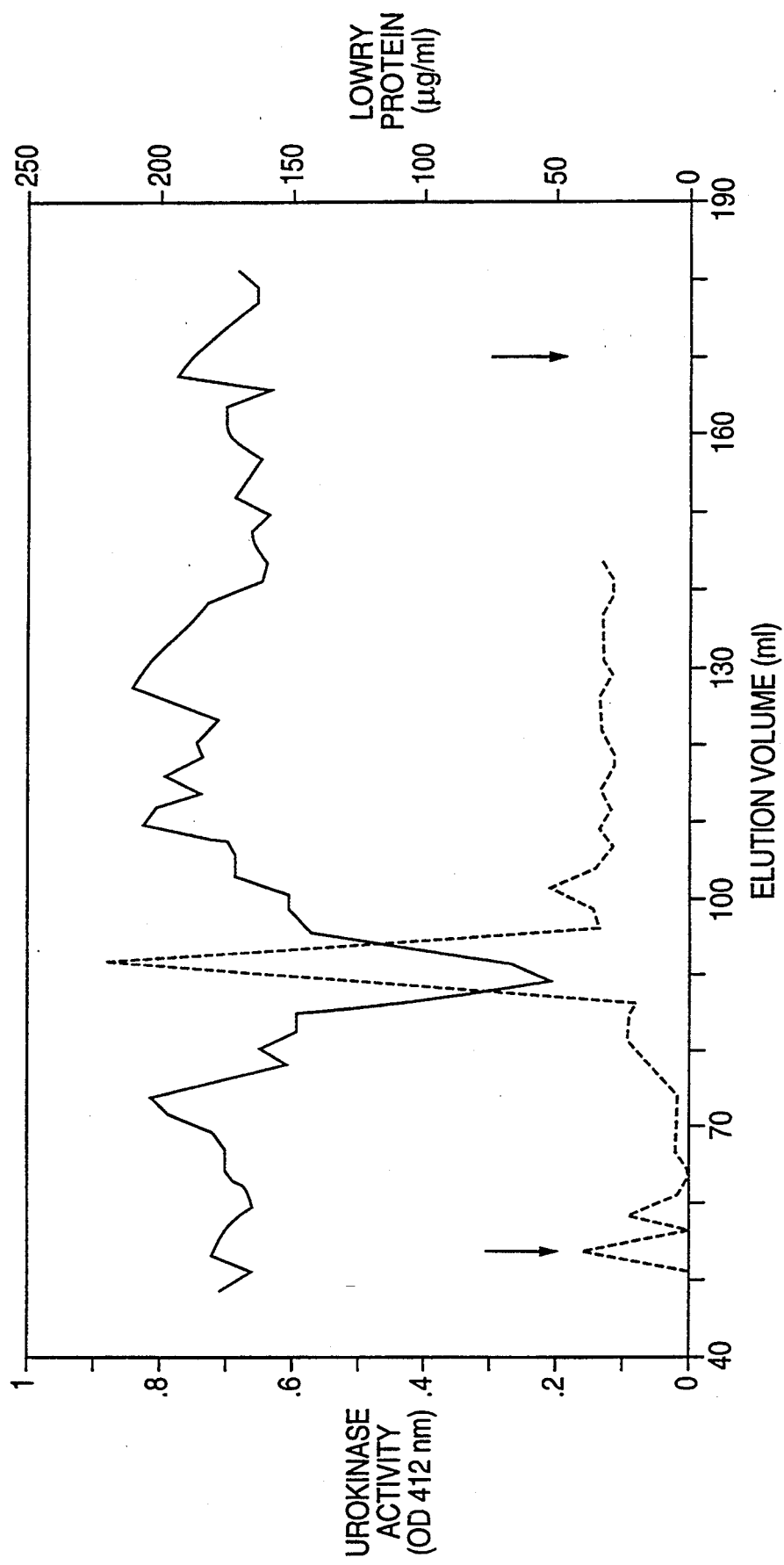

Gel filtration of minactivin preparations on Sephacryl S300 (Pharmacia) in the presence of salt show an apparent molecular size for minactivin identical to that of the serum albumin-standard, i.e.. 60–70,000 (FIG. 10). Analysis of the specificity of the enriched minactivin preparation obtained from this column by SDS-PAGE-fibrin overlay (as described above), gave identical results to those obtained in FIG. 6 for minactivin supernatants derived from monocyte culture. The observed inactivation of urokinase was not, however, a property of serum albumin since (a) human serum albumin had no effect on the colorimetric assay of urokinase, (b) the minactivin activity was not retained by an albumin affinity column of blue-Sepharose (Pharmacia), (c) the media concentration of human serum albumin would not have been expected to change with muramyl dipeptide or cell type in the induction experiments above and (d) cultures of monocytes without albumin or serum supplement also produced minactivin.

ROLE OF MINACTIVIN IN TUMOUR DIAGNOSIS AND TREATMENT

It is well established that several major human carcinomas produce significantly enhanced levels of urokinase-type plasminogen activator (HPA52) in contrast to the levels found in normal tissues. Recent extensive studies of Markus and his coworkers have included tumours of lung, prostate, breast and colon (30–32), with attention to enzyme content and type, as well as the rate of secretion by tissue explants in short-term culture (34–35). It has further been established that HPA52 is a different gene product (36), not derived by proteolytic or other modification of the tissue-type plasminogen activator (HPA66) which is ubiquitous in all vascularized tissues (37), such as colon endothelial cells. It is clear that a change of gene expression occurs in epithelial cells during development of human colon cancer, leading to higher levels of HPA52.

Biological processes in which cellular plasminogen activators have been implicated involve those physiological events associated with invasion and tissue destruction, such as inflammatory reactions and tumour metastasis (38). Specific actions in which plasminogen activators are involved which relate to its role as a mediator of tumour invasion include its ability to stimulate cell division (39), modify cell surfaces (40), enhance cellular migration (41), digest fibrin surrounding tumours (42), and also activate collagenase (43).

As minactivin has been shown to be a potent specific inactivator of urokinase-type plasminogen activator (HPA52 and HPA33), it follows then that minactivin has a range of applications as a clinical reagent, diagnosis of chronic inflammation and various types of carcinomas, as well as in the treatment of these conditions. By specific modulation of HPA 52 activity in vivo, minactivin would have no effect on the role of tissue-type plasminogen activator (HPA66) in the maintenance of haemostasis. Furthermore, as minactivin is a natural product, it has the advantage of lack of antigenicity and should avoid clearance problems within the body.

Minactivin, therefore has application as an index for inflammatory disease status. Currently chronic inflammatory conditions are treated with steroids, but it is generally difficult to monitor the progress of the treatment. Using an antibody to minactivin, the activation state of the macrophages in body fluids and tissues may be monitored and hence the progress of treatment. Inflammation or chronic ulceration and damage to the mucosal surface cell layer, or epithelium, results in the infiltration of large numbers of blood monocytes into the damaged area. In this environment, the monocytes may be stimulated to produce minactivin in amounts related to the extent of inflammation.

Furthermore minactivin has application as a reagent for identifying and defining tumour boundaries both in histological specimens and in vivo. While solid tumours are generally re-dressed through surgery, the use of minactivin would enable the identification of small metastatic cancers arising following surgical intervention. In the analysis of histological specimens, minactivin, or its antibody, may be labelled with an isotope, such as $I^{131}$, or conjugated to an appropriate enzyme or other chemical reagent. On contact with a histological specimen, minactivin will bind to the tumour-type plasminogen activator at its place of secretion, thereby identifying the tumour boundaries. Visualization of the complexed minactivin can then be effected by known procedures (44–47). For imaging tumours in vivo minactivin may be labelled with an appropriate isotope such as technetium$^{99}$, and after administration, the location and boundaries of the tumours determined by known radioisotopic methods (47–50). Moreover, as minactivin binds only to the active form of plasminogen activator, it would target tumour cells in growth or invasive stages.

In addition to its diagnostic applications, minactivin is also indicated for use in the direct treatment of tumours. As a specific inhibitor of the enzyme implicated in the process by which tumours invade surrounding tissues, regulation and, in particular, inhibition of tumour growth and metastases can be achieved. Furthermore, minactivin may be used as a drug delivery system to deliver lectins or toxins directly to growing tumours. It will be appreciated that this would offer many advantages in terms of specificity and extremely potent tumouricidal capability.

Further details of the production, purification and identification of minactivin are given in the following examples in association with the accompanying drawings and is not in any way intended to limit the scope of the invention.

PREFERRED EMBODIMENTS OF THE INVENTION

EXAMPLE 1

Biological Identification and Characterization of Minactivin

Methods

1. Colorimetric Assay of Plasminogen Activators

The method of Coleman and Green (12) was used to assay several types of plasminogen activator enzymes in an assay buffer of 50 mM glycine pH 7.8 containing 0.1% Triton X-100 and 0.1% gelatin. Dilutions were used which kept activity in the range 2–8 mPlough units (mPU) per assay. Enzyme (10 ul), plasminogen (0.1 mg/ml, 20 ul) and assay buffer (20 ul) were incubated for 45 min at 37°, then plasmin assay reagents (1 ml, see ref. 12) were added and incubated for further 30 min at 37°. The reaction was stopped by the addition of Trasylol (20 ul at 0.3 mg/ml), and the absorbance monitored at 412 nm. Human serum albumin (1%), used to supplement RPMI for monocyte culture, had no effect on the assay of urokinase by this method.

Human plasminogen was purified from pooled fresh plasma by two cycles of affinity chromatography on a lysine-Sepharose (Pharmacia) column (13), and was used in the assay at a final concentration of 0.3 uM. Tow commercially available preparations of human plasminogen activator were used: Urokinase, Calbiochem reference standard (lot 103285, 1700 Ploug units/vial) from Calbiochem-Behring Corp. La Jolla, Calif. and Sigma urokinase (lot 101F-05991, approx. 40,000 Ploug units/mg protein). These are referred to in this paper as CUK and SUK respectively. Both preparations were shown by SDS-PAGE and fibrin overlay development (see below) to be a mixture of the plasminogen activator of $M_r$ 52,000 (HPA52) with its proteolytic product of $M_r$ 36,000 (HPA36). Tumours of the rat mammary adenocarcinoma line 13762 (a gift from Dr. I Ramshaw, Dept. Experimental Pathology, JCSMR) were homogenised in 50 mM glycine pH 7.8 containing 0.5% Triton X-100. Bovine trypsin (type 1X), bovine thrombin (Grade 1) and porcine plasma were obtained from Sigma.

2. Colorimetric Assays of Minactivin

The quantity of minactivin in culture supernatants and cell lysates was determined by the inhibition produced in colorimetric assays of urokinase reference standard (12). The samples (20 ul) were preincubated with 4 mPU urokinase (20 ul) for 90 min at 23° before addition of plasminogen. Controls were included to verify that inhibition was at the level of plasminogen activation and not simply inhibition of plasmin, by direct addition of the minactivin source to the assay of preformed plasmin. One unit of minactivin was defined as that amount which inhibited 1 Plough unit of urokinase.

3. Radial Diffusion Assays

Fibrinogen (Sigma type X), human plasminogen and thrombin (Sigma grade 1) were cast in a 1.25% agarose (Sea Plaque, FMC Corp., Rockland, Me. USA) gel matrix 1.2 mm thick. After clotting at 37° C. the gel was hardened at 4° C., and 3 mm wells were cut for the application of urokinase/minactivin mixture (5 ul). The gels were incubated in a humidified box for 20 hours at 37° C., and the lysis produced was enhanced by extensive washing in saline, followed by staining with amido black.

4. SDS-PAGE and Fibrin Overlay Development of Plasminogen Activator Activity

The samples applied to SDS electrophoresis gels consisted of either the plasminogen activator enzyme alone in assay buffer, or the enzyme preincubated for 90 mins at 23° with culture supernatant and/or protease inhibitor, plus SDS sample buffer to give a final volume of 100 ul. The protease inhibitors employed were Trasylol, alpha$_1$-antitrypsin (Sigma), soybean trypsin inhibitor (Sigma), iodoacetamide, EDTA, SDS, tranexamic acid (Aldrich Chemicals, Milwaukee, Wis.) and benzamidine. The gel slabs were of 11% polyacrylamide and were run in the vertical position, washed in Triton X-100 and developed by contact lysis of a fibrin-agarose gel according to the method of Granelli-Piperno & Reich (13). The development time for the fibrin lysis was usually 5-8 hr at 37° C. The molecular weight of enzyme lysis bands was estimated by comparison with those of the commercial enzymes, and with the position of stained standard proteins (Pharmacia LMW Kit) in the acrylamide gel.

5. Morphology and Cytochemistry

For phase contrast microscopy, adherent monocyte or macrophage monolayers were washed twice and fixed in 1.5% glutaraldehyde in 0.1M cacodylate buffer (pH 7.4) for at least 30 minutes at room temperature (9) prior to examination.

Cytocentrifuge preparations were prepared in a Shandon Southern centrifuge. Briefly, 0.2 ml aliquots containing 50,000 cells in 10% foetal bovine serum were spun for 3 minutes at 500 rpm. The preparation was then dried rapidly in a hair dryer and the preparations stained with Mya-Grunwald Giemsa.

The presence of non-specific esterase was assayed using alpha-naphthyl acetate as substrate (10,11).

Phagocytic activity was assayed by incubating adherent monolayers or cell suspensions in RPMI-1640 containing 10% human AB serum and 1.1 um latex beads (Sigma) at a concentration of 100 beads per cell for 60 minutes at 37° C. Non-ingested beads were removed by washing monolayers or cell suspensions, 150×g for 10 minutes at 20°, three times with RPMI-1640. Cells ingesting two or more latex beads were judged to be phagocytic.

6. Monocyte and Macrophage Cell Preparations a) Human Blood Monocytes

Human mononuclear leukocytes were isolated on Ficoll-Hypaque (Pharmacia fine Chemicals, Sydney, Australia) gradients from buffy couts removed by the Red Cross Blood Transfusion Service of the Woden Valley Hospital. After four washes in Pi/NaCl at 4° C. to remove contaminating platelets the cell pellet was resuspended in RPMI-1640 (Gibco, Grand Island, N.Y.) containing 60 units/ml gentamicin. Purified monocyte monolayers were obtained by plating $10^7$ mononuclear cells in RPMI-1640 with 10% AB serum into 30 mm wells (Linbro multiwell plates. Cat. No. 7605805) which had been precoated for 30 min with 2 ml of human AB serum. Monocytes were allowed to adhere for 60 min at 37° C. in an atmosphere 5% $CO_2$ in air. Non-adherent cells were then removed by washing monolayers six times with RPMI-1640 prewarmed at 37° C.

Adherent monolayers were shown to be greater than 85% monocytes by several criteria. Polychromatic staining of the monolayer cells showed 94±6 percent of the cells to be monocytes having a large round or indented nucleus with basophilic cytoplasm. Staining for the cytoplasmic enzyme non-specific esterase showed monolayers to be 85±2% positive for this monocyte marker. Ninety one percent of the adherent cells phagocytosed latex beads confirming that the adherent cell population which showed the morphological and histochemical appearances of mononuclear phagocytes also exhibited this characteristic functional property.

During in vitro culture, monocytes underwent pronounced changes in cell size and morphology. Cytocentrifuge preparations of cultured monocytes showed that monocytes continued to increase in size throughout the culture period and by the end of seven days, many cells had more than doubled in apparent size. Occasional binucleated cells were also seen. As monocytes increased in size their cytoplasm became heavily vacuolated, and cytoplasmic granules also became evident. Further culture resulted in increased formation of multinucleated giant cells.

b) Peritoneal Macrophages

Two liter lots of dialysate fluid, from patients undergoing routine peritoneal dialysis for chronic renal failure, were centrifuged at 300×g for 10 minutes at 20° C. The cell pellet was resuspended in 50 ml of RPMI-1640 and recentrifuged for 10 minutes at 200×g at 20° C. The cells were then resuspended in RPMI-1640 to a final concentration of approximately $2 \times 10^6$ per ml and 6 ml aliquots of the peritoneal cell suspension were underlayed with 3 ml of Ficoll-Hypaque and centrifuged for 20 minutes at 400×g at 20° C. The cells were resuspended to a concentration of $1 \times 10^6$/ml in RPMI-1640 containing 10% human AB serum.

High yields of mononuclear cells were obtained from Ficoll-Hypaque gradients of peritoneal washings. Forty-seven percent of the cells were macrophages as judged by morphologic criteria. Cytocentrifuge preparations of the mononuclear cell fraction showed that the macrophage population was heterogeneous and included large mature cells with abundant cytoplasm and occasionally two nuclei, as well as smaller cells more characteristic of monocytes, with indented nuclei and a higher nucleus to cytoplasm ratio.

Peritoneal macrophages were further purified by adherence to plastic culture trays as described above for monocytes. Following removal of the non-adherent cell layer, viable peritoneal macrophages could be maintained in culture for up to three weeks provided that the culture media was changed every 2-3 days. Peritoneal monolayers were routinely greater than 87% macrophages as determined by non-specific esterase staining.

c) Bone Marrow-derived Macrophages

Fresh pieces of human ileac crest and rib marrow were obtained during orthopaedic procedures and dispersed in RPMI-1640 media containing 10% giant cell tumour (GCT) culture supernatant (Gibo-Biocult, Grand Island, N.Y., USA) and 10% foetal bovine serum. This primary culture was maintained for 7 days on gelatin-coated flasks (1). After this period, monocyte/macrophages were purified by adherence to culture dishes prepared as for blood monocytes and the secondary adherent culture used for minactivin measurements. The cells obtained were greater than 90% positive for non-specific esterase.

d) Colonic Mucosa Macrophages

These cells were obtained from resected colons by enzymatic disaggregation of the colonic mucosa according to the method of Golder and Doe (2). They were grown as adherent monolayers in RPMI-1640 as for monocytes. The cells obtained were greater than 85% non-specific esterase positive and phagocytosed sheep red blood cells.

7. Cell Culture a) Monocyte and Macrophage

Monocyte or macrophage monolayers were cultured in RPMI-1640 with 1% human serum albumin (Commonwealth Serum Labs., Melbourne, Australia). Cultures of cells from sources (a)-(d) above were kept as close as possible to a ratio of $3 \times 10^6$ cells/ml media.

The following agents were used in cell culture experiments:

(a) Muramyl dipeptide (N-acetyl-muramyl-L-alanyl-D-isoglutamine, Peninsula Laboratories, San Carlos, Calif., USA) at 5 ug/ml, (b) Salmonella minnesota R595 cell wall lipopolysaccharide (3). The latter was prepared by sonication of the water-insoluble extract in 0.1% trimethylamine followed by extensive dialysis against Pi/NaCl. The final concentration in cultures was 0.1 ug/ml. Dexamethasone and phorbol myrastate acetate (Sigma Chemical Co., St. Louis, Mo. USA) were used at a final concentration of 0.1 uM, and 10 ng/ml, respectively.

b) Transformed Cell Lines

The human macrophage-like cell lines U937 (4) and HL60 (5) were obtained from Drs R Ulevitch and R G Painter (Scripps Clinic, and Research Foundation, La Jolla, Calif., USA). The U937 cell line was also obtained from the American Type Culture Collection (Rockville, Md., USA). RC2A (6) was from Dr N Kraft (Prince Henry's Hospital, Melbourne, Australia). MLA144 is a Gibbon ape T-lymphocyte line (7). The human erythroid line K562 (8) was a gift of Dr H S Warren, Cancer Research Unit, Woden Valley Hospital, while COLO 394 was a human colon carcinoma cell line provided by Dr R Whitehead, Ludwig Institute of Cancer Research, Royal Melbourne Hospital, Melbourne. All of the above cells were grown in RPMI-1640 medium without serum prior to harvest of the supernatants for analysis. Cell lysates were prepared in the presence of 0.5% Triton X100 for enzyme studies.

BIOLOGICAL CHARACTERISTICS OF MINACTIVIN

Results

1. Minactivin Production in Cell Populations a) Human Blood Monocytes

Minactivin was shown to be present in serum-free conditioned media from adherent human monocytes by inhibition of the activity of urokinase in the colorimetric assay of Coleman and Green (12) (FIG. 1). This inhibition was observed whether or not the initial adherence of the cells was facilitated by human serum. The non-adherent mononuclear fraction obtained during preparation of adherent monolayers did not produce any detectable minactivin in culture.

Figure 1B:
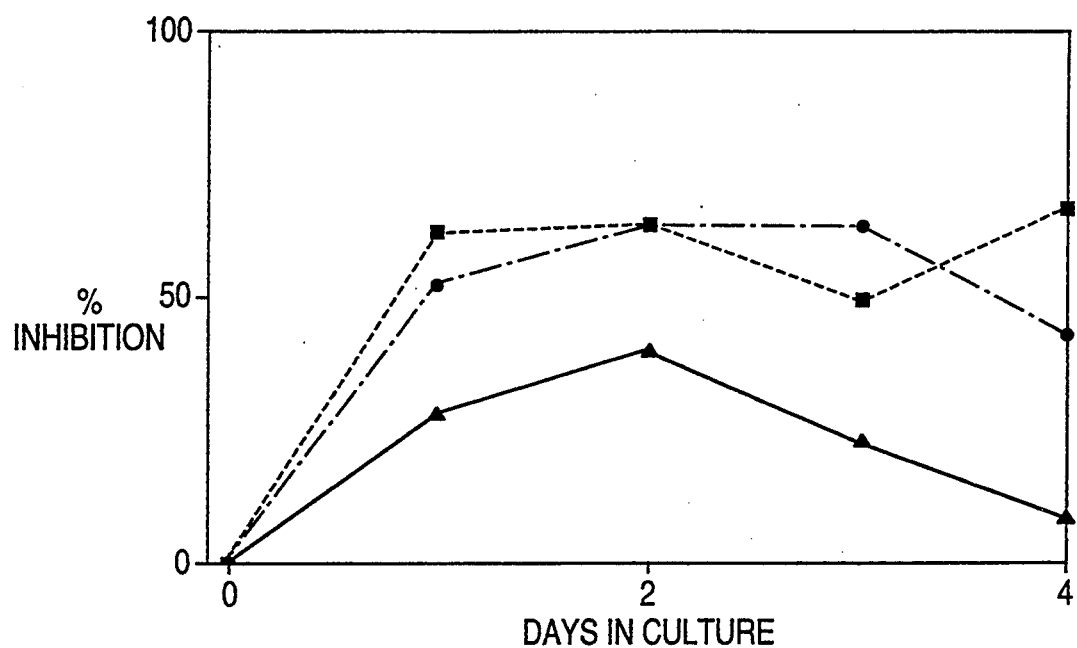
Figure 2:
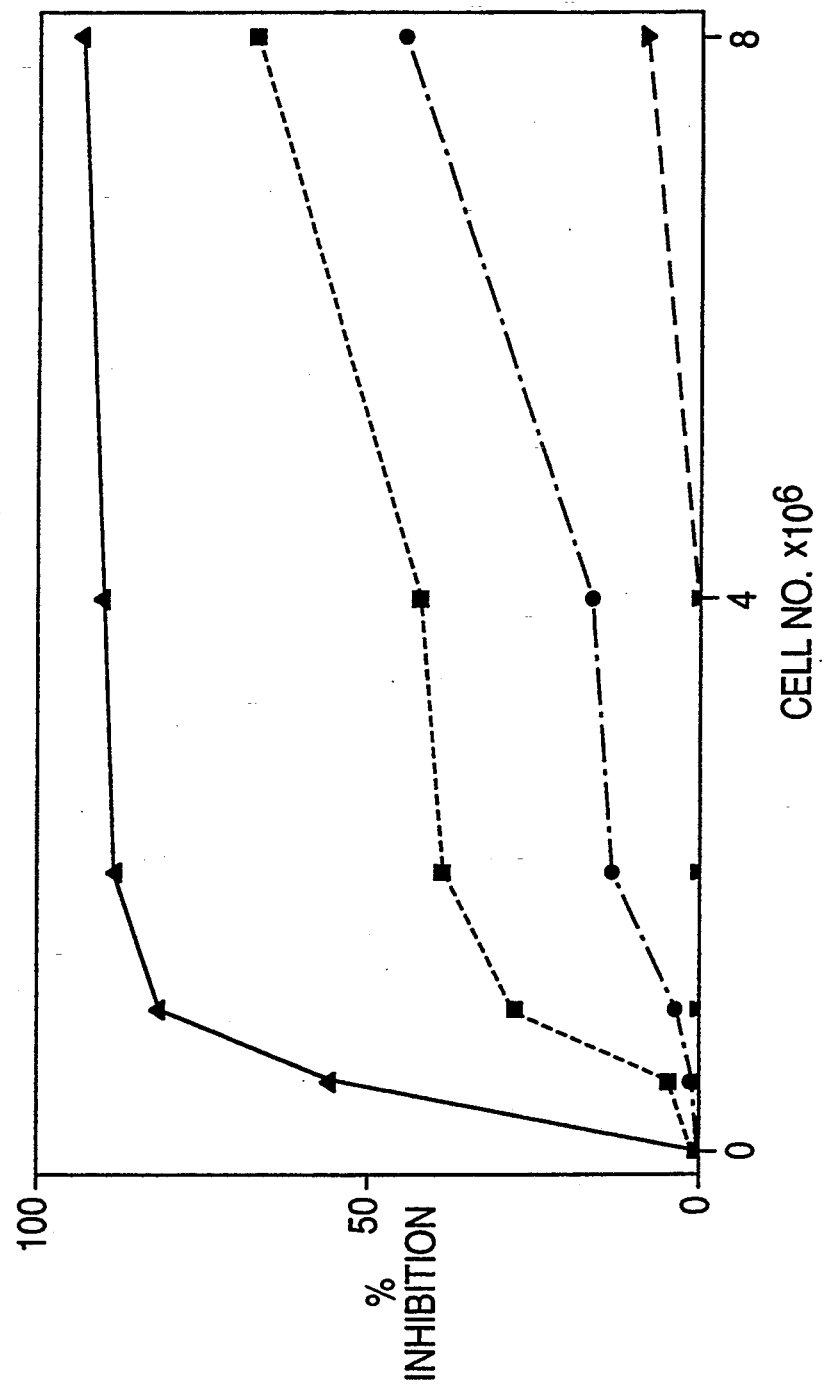

Maximal minactivin activity was obtained using culture supernatant from the first 24 hr of monocyte culture. Subsequently the rate of inhibitor production for each successive 24 hr period declined until it was insignificant after four days. This effect was observed in both the culture supernatants and cell lysates. However, activation of monocytes in vitro by muramyl dipeptide or bacterial lipopolysaccharide led to both sustained production and secretion of minactivin (FIG. 1A and 1B). The amount of inhibitor in the culture supernatant from the first 24 hr period was correlated with cell number (FIG. 2). Maximum levels of minactivin were produced in culture by cells in densities of greater than $10^6$ cells/ml. Relatively lower amounts of minactivin were produced (per cell) at higher cell densities. Treatment of monocyte cultures with dexamethasone ($10^{-6}$–$10^{-8}$M) which has previously been shown to induce synthesis of an inhibitor of plasminogen activator in human fibroblast cultures (14), had no effect on the production of minactivin.

b) Human Peritoneal Macrophages

Figure 3:
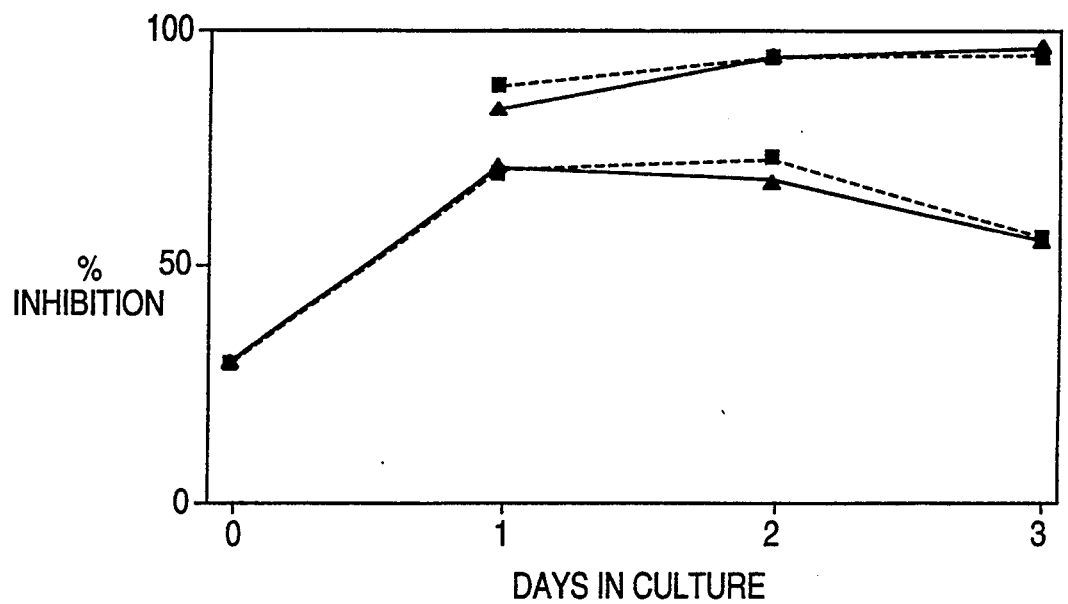

While lysates of freshly isolated blood monocytes did not contain minactivin (see FIG. 1B), all lysates of freshly isolated adherent peritoneal macrophages contained significant levels of minactivin (approx. 30% inhibition), which subsequently increased during culture (FIG. 3). This sustained production of minactivin was also reflected in the high levels of secreted product measured in the corresponding culture supernatants. Unlike control monocyte cultures, peritoneal macrophage lysate minactivin levels remained high throughout the 3 day culture period. This cell population appeared from its morphology to consist largely of newly recuited monocytes, indicating that the in vivo stimulus of mild inflammation induced by repeated dialysis was sufficient to recruit and activate monocytes to produce minactivin within the peritoneal cavity. The peritoneal macrophages appeared to be unresponsive to further activation, since addition of muramyl dipeptide did not further enhance minactivin production in either the lysates or the supernatants (FIG. 3)

c) Bone Marrow-Derived Macrophages

Bone marrow macrophages were obtained as the adherent cells after 7 days of GCT (giant cell tumour cultures supernatant) stimulated growth of primary marrow cultures. Since these cells could only be studied as secondary cultures after the 7 day primary culture of the tissue, their initial minactivin production and secretion can not be directly compared to freshly isolated blood monocytes or peritoneal macrophages.

Figure 4:
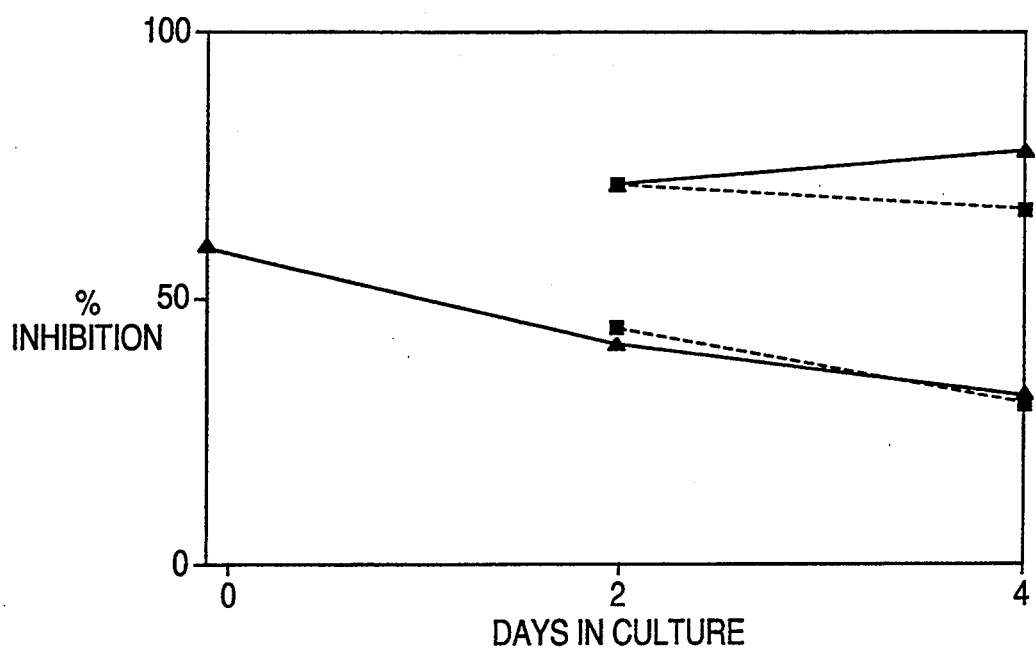

Nonetheless, after primary culture for seven days, the lysates for adherent bone marrow macrophages obtained during secondary culture showed high levels of minactivin activity which declined regardless of the presence or absence of muramyl dipeptide (FIG. 4). These bone marrow cells were also found to secrete high levels of minactivin into supernatants, and as observed with the lysates, this level was not affected by muramyl dipeptide (FIG. 4).

d) Colonic Mucosal Macrophages

Macrophages isolated from enzymically disaggregated mucosa of resected human colon had only very limited ability to produce minactivin in culture, and the levels were insignificant compared to those from the three sources above (mean value of 4% inhibition for 24 hr supernatants in four separate experiments). These low levels were not increased when Salmonella minnesota lypopolysaccharide (0.1 ug/ml) was added to cultures.

To determine if this lack of responsiveness of intestinal macrophages could be attributed to the prolonged exposure to the degradative enzymes (collagenase and DNAase) used in their isolation, some normal human blood monocytes were subjected to several hours incubation in the supernatant medium from an intestinal macrophage preparation. The enzyme treated blood monocytes retained their ability to produce and secrete minactivin in subsequent culture (see Table 1).

TABLE 1

|  | Control Monocytes | Enzyme Treated |
|---|---|---|
| Lysate | 90% | 100% |
| Supernatant | 67% | 72% |

Production of minactivin by human blood monocytes before and after incubation with colon disaggregation supernatant containing DNAse and collagenase. The results are expressed as per cent inhibition of urokinase assay by monocyte supernatant.

Thus, it appears that blood monocytes are at an ideal developmental stage for potential secretion of minactivin. This potential is realised when they are activated with muramyl dipeptide in vitro, or actively recruited to an inflammatory site in vivo. On the other hand, mature tissue macrophages isolated from intestinal mucosa appear to have lost their ability to produce to secrete minactivin, even upon stimulation.

e) Human Macrophage Cell Line U937

Minactivin activity could not be detected in supernatants obtained from the human macrophage cell line U937 when assayed by the method of Coleman and Green (12). However, when this cell line was cultured in the presence of dexamethasone (1 uM), significant levels of minactivin were measured in the culture supernatants. This result may be explained by the concomitant production of plasminogen activator by U937 cells which would effectively bind the minactivin produced, thereby masking its detection by colorimetric assay. Indeed, when the U937 cells were removed from dexamethasone containing media for 72 hours, high levels of intracellular plasminogen activator were induced as measured by assay of plasminogen activator activity in 0.5% Triton X100 cell extracts. U937 cells cultured for greater than 7 days in the absence of dexamethasone completely lost their ability to produce minactivin. Addition of dexamethasone, even to 10 uM final concentration, did not restore minactivin production.

The level of minactivin secreted constitutively by U937 cells was approximately 4-fold lower than that produced by muramyl-dipeptide induced monocytes in culture. However, the level of Minactivin Secreted by U937 cells could be enhanced 16 fold by the addition of phorbol esters, such as phorbol myrastate acetate, to the cells in culture. Minactivin activity was not detected in supernatants obtained from the human macrophage-like cell line RC2A or the T-lymphocyte cell lines of human (Jurkat) and Gibbon ape (MLA144) origin.

2. Minactivin Specificity a) Inhibition of Fibrinolysis

Figure 5:
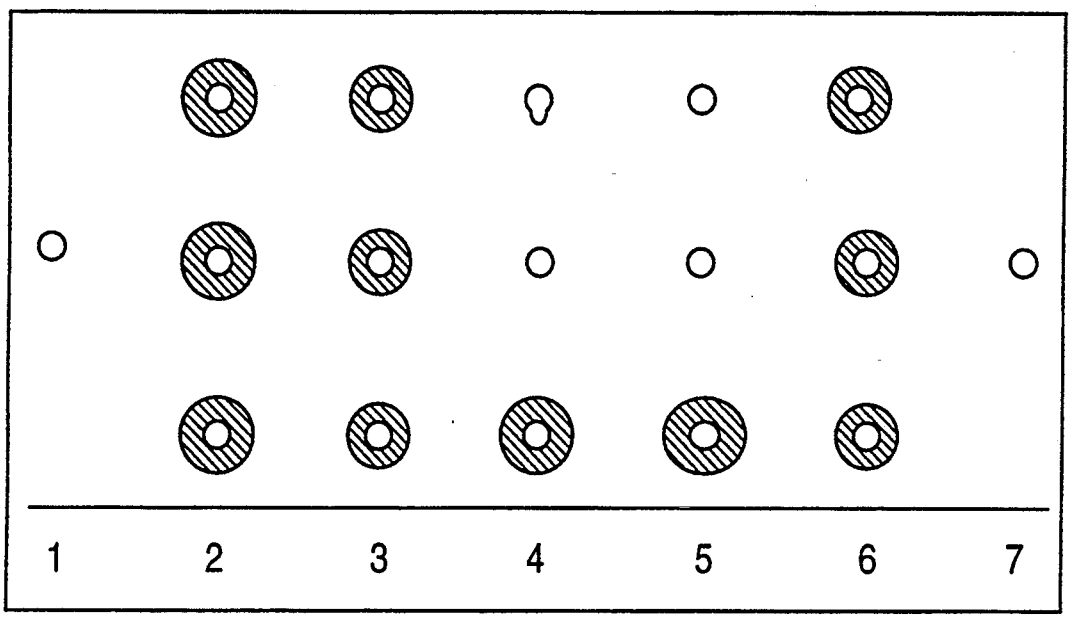

The specificity of minactivin inhibition of proteases was investigated by incubating minactivin containing monocyte culture supernatants with various enzymes added to microwells cut in a fibrin/agarose gel. Plasminogen (20 ug/ml) was included in the gel mixture to enable plasminogen activator expression, and suitable concentrations of enzyme were chosen to give comparable areas of lysis after incubation for 20 hours at 37° (see description of FIG. 5).

Minactivin was clearly not an inhibitor of plasmin or trypsin (FIG. 5), even when preincubated with these enzymes for 2 hrs at 23° before application to the wells. Among human plasminogen activators, both preparations of urokinase (CUK and SUK) lost all fibrinolytic activity when treated with minactivin. However, the fibrinolytic activity of human melanoma culture supernatant, due almost entirely to tissue-type plasminogen activator (HPA66) (see below), was not inhibited by minactivin, even after preincubation. The clotting of fibrinogen by thrombin was also unaffected by minactivin.

b) Inhibition by Colorimetric Assay

The Coleman and Green (12) assay was further applied to investigate the specificity of minactivin inhibition. In the absence of plasminogen, incubation with plasmin assay reagents (12) can be used as a highly sensitive assay for trypsin as well as plasmin, while in the presence of plasminogen several types of plasminogen activators can be assayed. A notable exception however is HPA66 in human melanoma conditioned media, which was inactive in this assay, presumable due to the lack of fibrin (16).

Minactivin did not inhibit the lysine thioesterase activity of trypsin or plasmin (Table 2). However, the plasminogen dependent activity of the urokinase-type plasminogen activators, CUK and SUK and APA52 from a Gibbon ape T-lymphocyte line (MLA 144), were strongly inhibited by minactivin. Furthermore, the inhibition of urokinase was observed only when minactivin was present during incubation with plasminogen, and did not occur if minactivin was added at the plasmin assay stage.

The activity of rat plasminogen activator (RPA48, probably homologous to HPA52) present in the diluted homogenate of rat 13762 tumour was not affected by minactivin.

| Enzyme or Source of PA | Amount | Control Activity ($A_{412}$) | Minactivin treated ($A_{412}$) | % of Control Activity |
|---|---|---|---|---|
| Trypsin | 6 ng | 0.32 | 0.31 | 97 |
| Plasmin | 180 ng | 0.94 | 0.98 | 104 |
| CUK | 4 mPU | 0.72 | 0.00 | 0 |
| SUK | 8 mPU | 0.88 | 0.00 | 0 |
| Melanoma | 20 ul supnt | 0.05 | 0.07 | — |
| MLA144 | 20 ul supnt | 0.69 | 0.08 | 12 |
| Rat tumor-13762 | 20 ul 1%-homog. | 0.53 | 0.50 | 94 |

Inhibition of Protease colorimetric assays by minactivin. Undiluted miniactivin culture supernatant (20 ul) was preincubated for 2 hrs at 23° with the enzymes indicated in a final volume of 40 ul. Plasminogen (20 ul, 100 ug/ml) was then added to the activators, plasmin assay reagents (1 ml) were added to the other proteases, and the respective assays continued to colour development.

c) SDS-PAGE and Fibrin Overlay

The fibrin overlay method of Granelli-Piperno & Reich (14) was used to verify the specificity of minactivin inhibition and to determine whether the various plasminogen activators were irreversibly inactivated by minactivin. Preincubations of enzymes with minactivin were subjected to SDS-PAGE, and residual enzyme activities were visualized as lysed areas on a fibrin-/agarose gel supplemented with plasminogen.

Figure 9A:
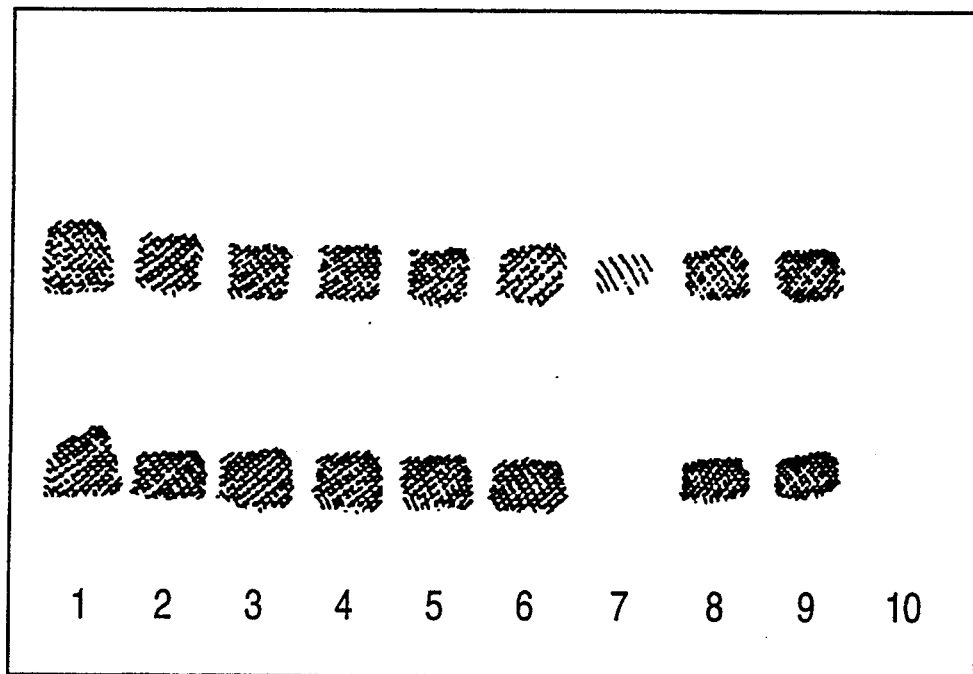

When the acrylamide and fibrin gels were incubated together for 5 hrs, the control (untreated) urokinase (CUK) gave two prominent bands: one characteristic of HPA52 and a second characteristic of its proteolytic product (17), HPA36 (FIG. lane 1). However if CUK was preincubated with minactivin before SDS-PAGE, a single weak lysis band appeared in the overlay gel after 5 hrs, and this was located at a higher molecular weight position that HPA52 (FIG. 9A, lane 10).

Figure 6:
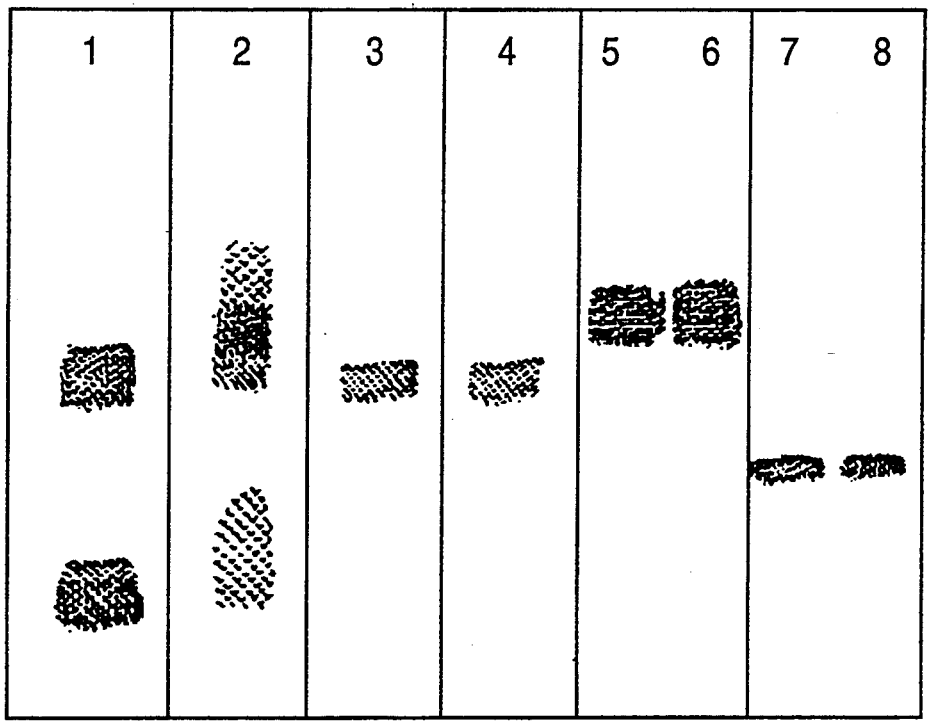

When the gels were incubated together for 20 hrs, this band increased in intensity, and an additional band became visible at a higher apparent molecular weight than that observed for HPA36 (see FIG. 6, lane 2). These results demonstrate that minactivin inactivates HPA52 and HPA36 in such a way that the final residual activities are of higher molecular weight than the untreated enzymes. Thus, it appears that the mode of interaction between minactivin and urokinase may involve complex formation or a radical change in the structure of urokinase affecting its electrophoretic mobility (see Section 3 below). HPA36 appeared to be more susceptible to inactivation than HPA52.

The Gibbon ape cell line MLA 144 secreted plasminogen activator into serum free culture media, and after SDS-PAGE and fibrin development, this activity was resolved into two closely spaced bands in the same molecular weight region as the HPA52 from human urokinase (FIG. 6, lane 3). Neither of these bands was affected by preincubation of the MAL 144 culture supernatant with minactivin (FIG. 6, lane 4). The plasminogen activator of $M_r$ 66,000 from human melanoma culture supernatant (FIG. 6, lanes 5 & 6) and that of $M_r$ 48,000 from a rat tumour were also unaffected (FIG. 6, lanes 7 & 8) by treatment with minactivin. These results demonstrate that minactivin specifically inhibits human urokinase-type plasminogen activators (HPA52 and HPA36), and not human tissue-type plasminogen activator (HPA66), nor plasminogen activators from (at least some) other mammalian species.

3. Interaction of Minactivin with Urokinase-type Plasminogen Activator

Figure 7:
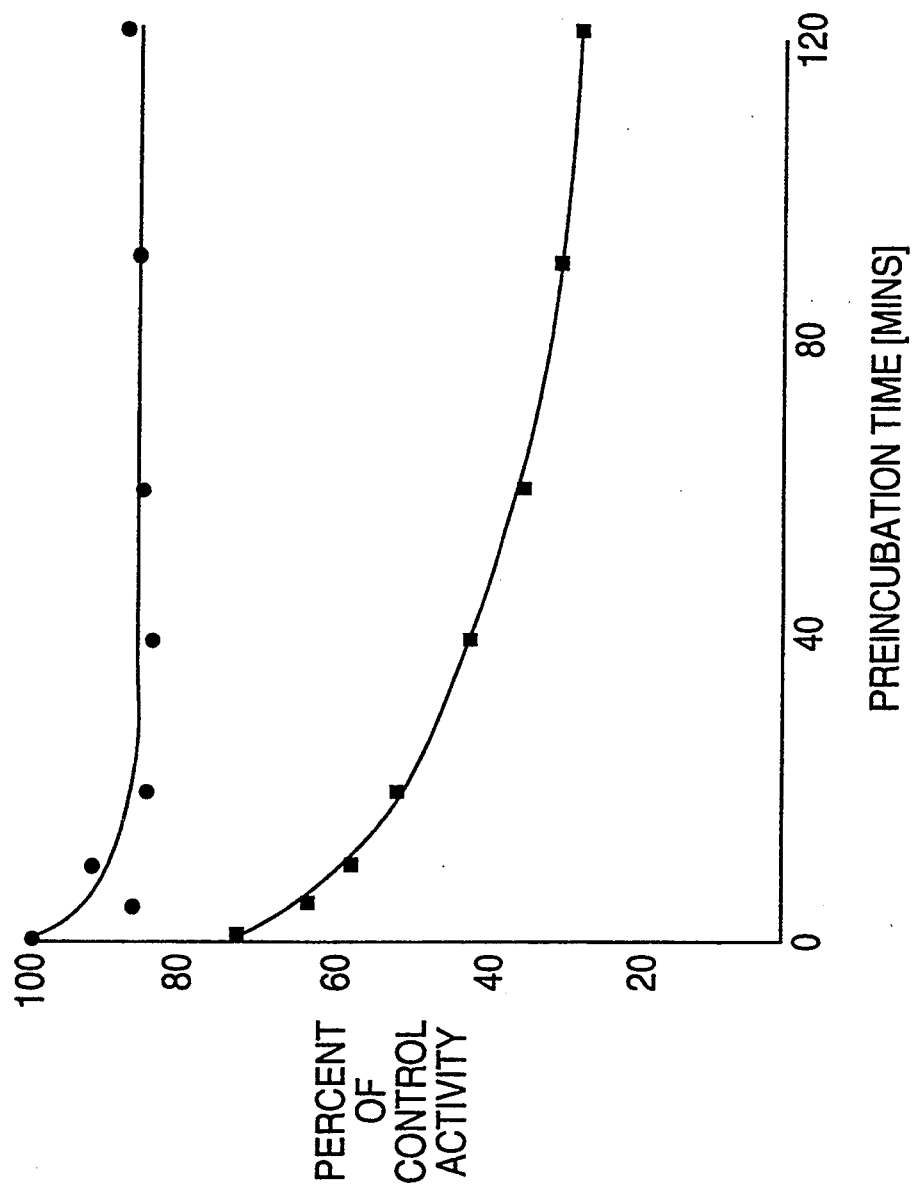
Figure 8:
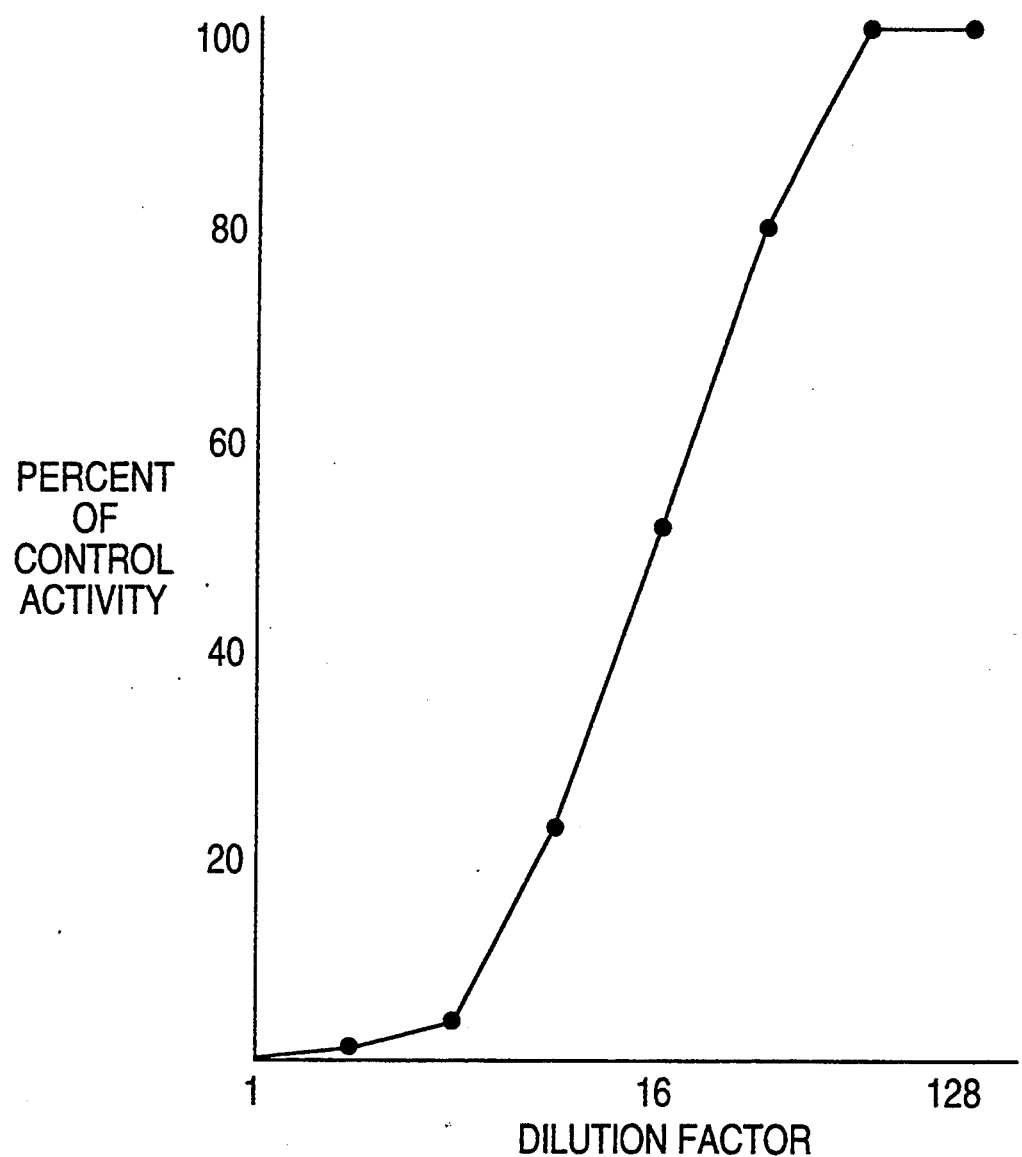

The interaction between minactivin and urokinase was analysed by preincubation of minactivin and CUK in the absence of plasminogen, followed by assay of the residual plasminogen activator activity in the colorimetric assay described above. Inactivation took place over a time course of two hours at 23°, and the final level of residual plasminogen activation activity was less than half that observed when urokinase, minactivin and plasminogen were mixed at zero time (FIG. 7). During the two hour preincubation, inactivation was initially rapid and then plateaued, so that further incubation resulted in no inactivation of the residual urokinase. This result suggested that the reaction was stoichiometric, rather than that, for example, the urokinase was degraded by a protease. Titration of urokinase with dilutions of minactivin containing culture supernatant produced a simple interaction curve shown in FIG. 8. The activity of 4 mPU of urokinase (CUK) could be 50% inactivated by the equivalent of 1.5 ul of the culture supernatant used for this experiment.

Figure 9B:
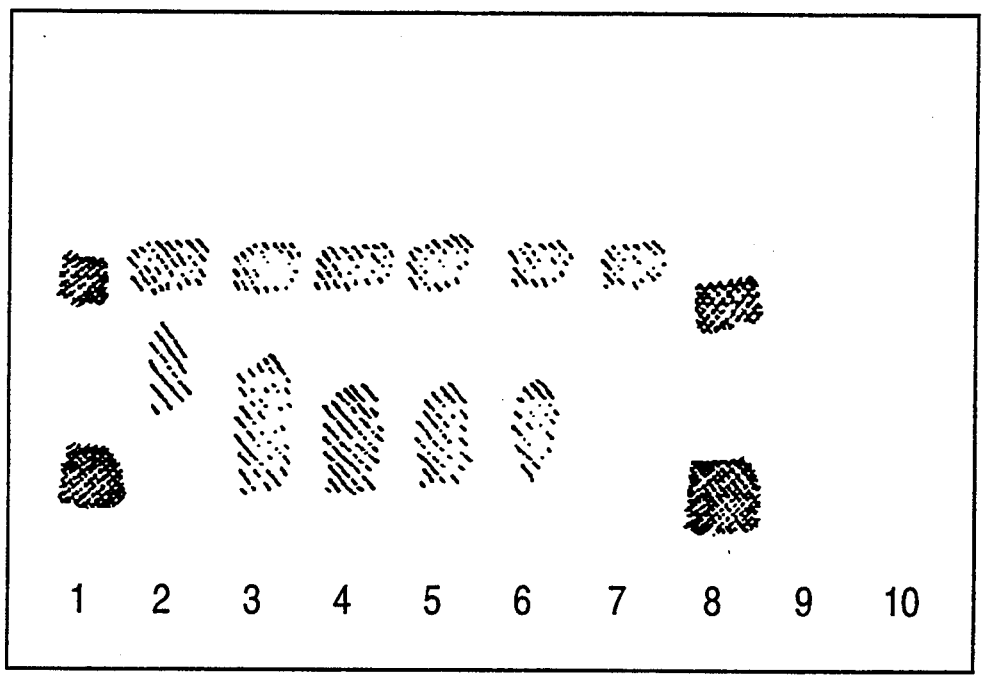

The culture supernatants used for these experiments was devoid of any detectable general proteolytic activity, as shown by the control well in the fibrinolysis experiment above (FIG. 5), and by the lack of detectable lysine thioesterase activity in the highly sensitive colorimetric assay. However, to determine whether the inactivation of urokinase by minactivin involved proteolytic activity on the part of either of these two molecules, CUK was preincubated with and without minactivin, and in the presence of each of a wide range of protease inhibitors. The protease inhibitors and their final concentrations were: Trasylol, 0.2 mg/ml; alpha$_1$-antitrypsin, 16 ug/ml; soybean tripsin inhibitor, 0.16 mg/ml; iodoacetamide, 3 mM; EDTA, 6 mM; SDS, 0.6%; tranexamic acid, 3 mM and benzamidine, 3 mM. These preincubations were then subjected to SDS-PAGE and the urokinase activity visualized by fibrin lysis as above. Control preincubations with each of the protease inhibitors in the absence of minactivin showed that only soybean trypsin inhibitor abolished the usual HPA52 and HPA36 bands visible after electrophoresis (FIG. 9A). When minactivin was included in each preincubation, none of the other protease inhibitors prevented the inactivation of urokinase catalysed by minactivin (FIG. 9B). However, SDS was able to prevent inactivation when added to the urokinase before or immediately after minactivin (FIG. 9, lane 8). Thus minactivin is demonstrated to be an inactivator of plasminogen activator, rather than an inhibitor.

Taken together, these results suggest that the mode of action between minactivin and urokinase involves the initial rapid formation of a reversible complex, followed by a slower SDS-sensitive phase (insensitive to protease inhibitors) which yields an irreversible product of higher molecular weight than the free enzyme but lower than that expected for a 1:1 complex of enzyme and minactivin. Thus, SDS added to the preincubation at zero time was able to completely reverse the inhibitory effect of minactivin, whereas preincubation with minactivin followed by treatment with SDS resulted in complete inhibition of both HPA52 and HPA36. Trace activities appeared at positions of higher molecular weight after prolonged development, which could be inhibited if minactivin was added to the fibrin overlay. These may represent small amounts of partially activated enzyme or a dissociation product from the initial reversible complex formation.

A number of plasminogen activators from transformed cells of the human macrophage lineage were also tested for minactivin inactivation by colorimetric assay. It was clear that minactivin strongly inhibited the plasminogen activators from the human macrophage precursor cell line (HL60) and the human macrophage-like leukemic cell line (RC2A) (Table 3). The plasminogen activators secreted by the human erythroid cell line (K562) and the primate T-lymphocyte cell line (MLA 144), were also inhibited, but not the urokinase of mouse urine.

| PA Source | Urokinase equivalent % Inhibition of 2 mPU |
|---|---|
| Urokinase | 95 |
| Monocyte | 18 |
| RC2A | 80 |
| HL60 | 78 |
| K562 | 75 |
| MLA144 | 60 |
| Mouse urine | 4 |

Inhibition by monocyte minactivin of plasminogen activators from various sources, including human transformed cell lines.

4. Specificity of Minactivin Obtained from Other Cell Populations

Confirmation that the minactivin produced by other macrophage cell populations was identical to minactivin produced by monocytes was obtained using fibrin radical diffusion assays, as monocyte minactivin is highly specific for human urokinase type plasminogen activators.

A selection of protease and plasminogen activators, including plasmin, trypsin, HPA66 (tissue-type activator from human melanoma culture supernatant) and human urokinase (both HPA52 and HPA36) were tested for inhibition by minactivin produced in each cell population.

Figure 11:
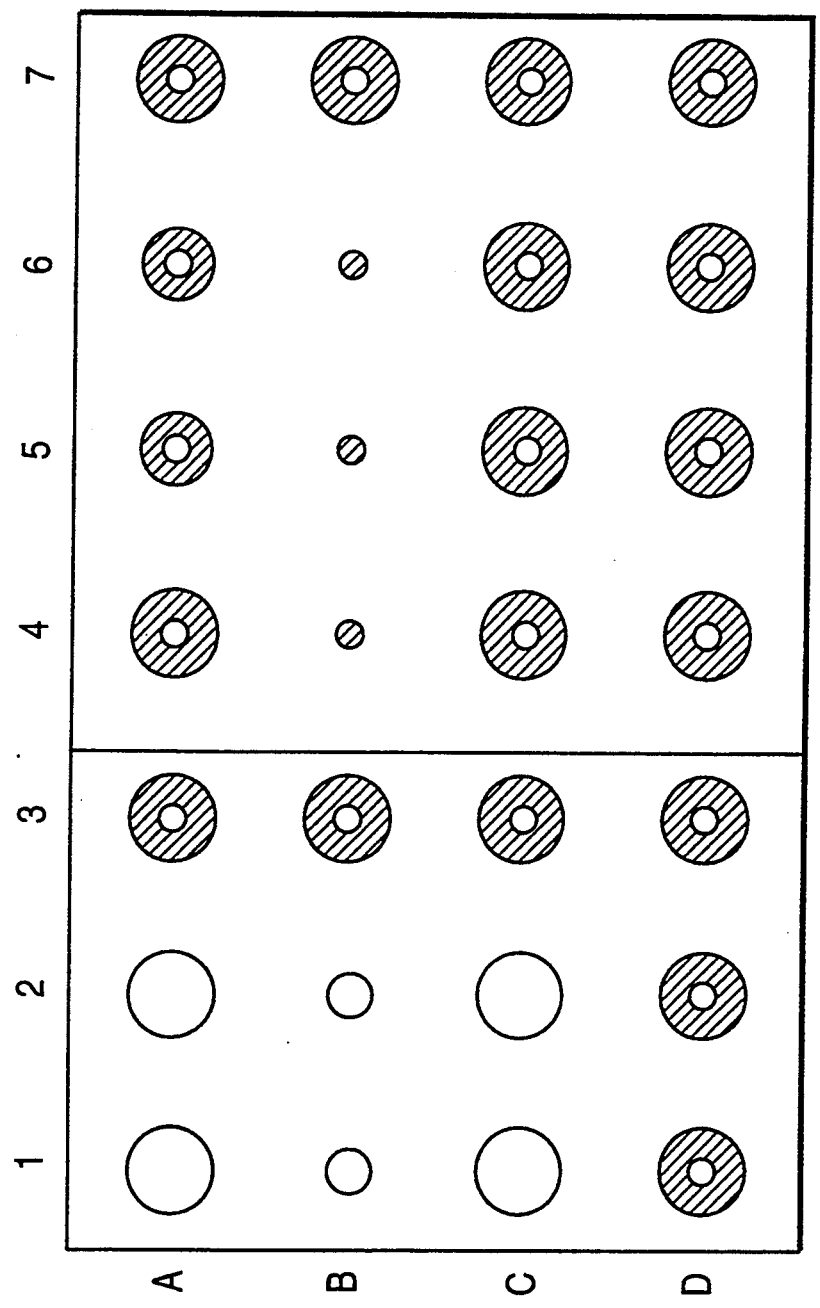

Specific inhibition of urokinase-type plasminogen activator was observed using culture supernatants from both peritoneal macrophages and blood monocytes (FIG. 11). The minactivin produced by these cells had no effect on the activities of plasmin, trypsin or HPA66. Total cell lysates of peritoneal macrophages, blood monocytes and bone marrow macrophages which had been solubilized with Triton X100, all produced inhibition of urokinase-type plasminogen activator, with no detectable inhibition of plasmin or trypsin. The lysates of blood monocytes and peritoneal macrophages did, however, show some weak inhibition of HPA66 (see FIG. 11).

Figure 12:
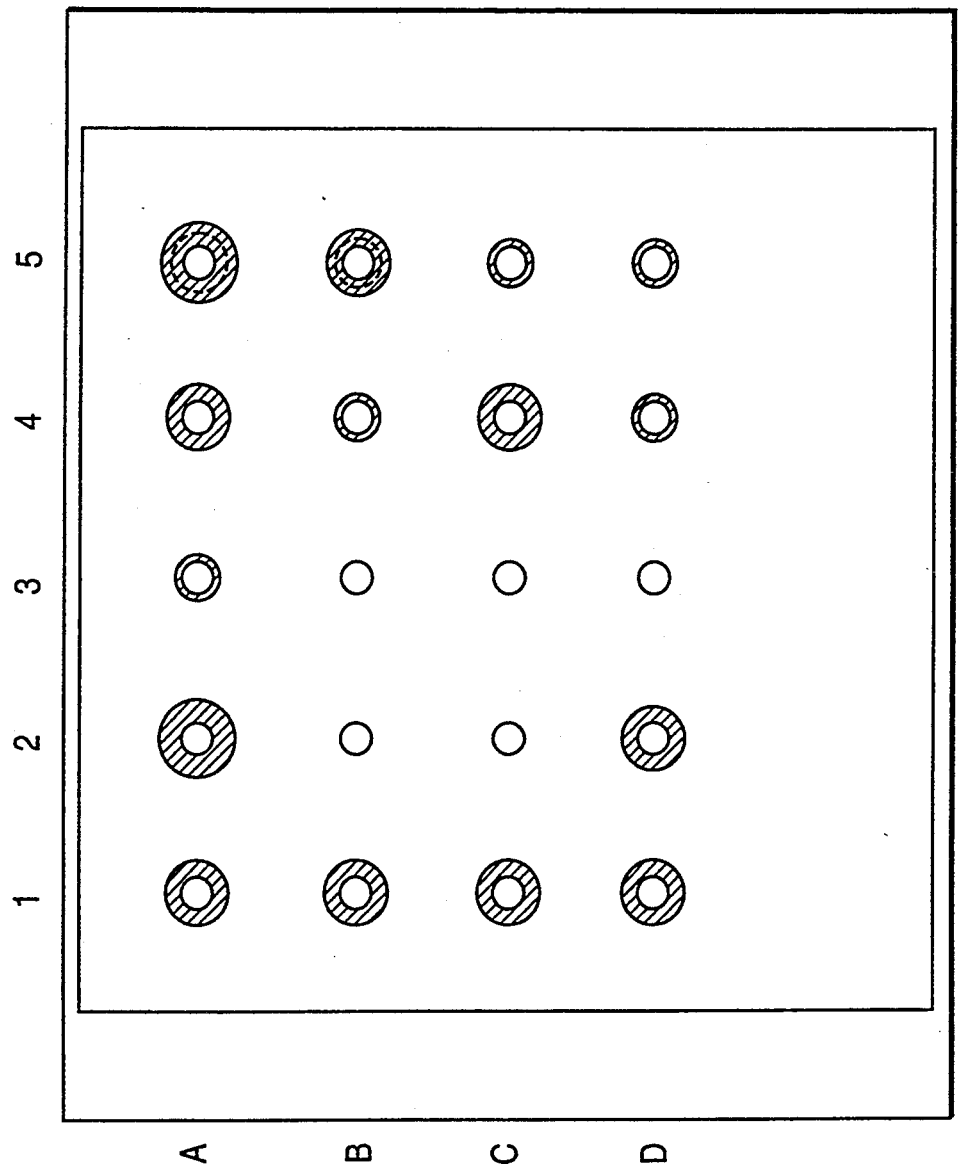

The minactivin produced by U937 cells was found to be identical to monocyte derived minactivin in its general characteristics. A comparison of their specificities by fibrin radial diffusion using purified minactivin from both U937 cells and induced monocytes demonstrated that minactivin from both sources specifically inhibited the urokinase-type plasminogen activators, CUK and SUK, and not tissue-type plasminogen activator (HPA66) (FIG. 12). No inhibition was observed in the plasmin and mouse urokinase controls.

The electrophoretic mobilities of the monocyte and U937 cell derived minactivin preparation were very similar, when compared on a non-denaturing, discontinuous polyacrylamide gel system (see legend FIGS. 13A and 13B). The minactivin inhibition bands were visualized by incubation of the gel with urokinase, followed by fibrin/agarose gel overlay. The minactivin preparation from the U937 cell line appeared to have a slightly greater electrophoretic mobility than that derived from monocytes (FIGS. 13A and 13B). This minor difference may reflect a difference in the amount of lysis detected on the gel or may be due to a difference in glycosylation of the minactivin from the two different sources.

Minactivin isolated from U937 cells or induced monocytes differs in specificity to the plasminogen activator inhibitor isolated from human placenta (23) as demonstrated by fibrin radial diffusion (FIG. 12). The human placental inhibitor (Calbiochem) inactivates both urokinase-type and tissue-type plasminogen activators, whereas minactivin inhibition appears to be specific for the former.

EXAMPLE 2

Process for the Purification of Minactivin

1. Purification of Minactivin from Human Monocyte Cultures

Monocytes were isolated form human blood by first centrifuging to form a white "buffy coat" of the leukocytes on top of the erythrocytes. The leukocytes were separated into granulocytes and lymphocytes plus monocytes by layering on Ficoll-Hypaque. The monocytes were separated from the lymphocytes by centrifugal elutriation.

Figure 14:
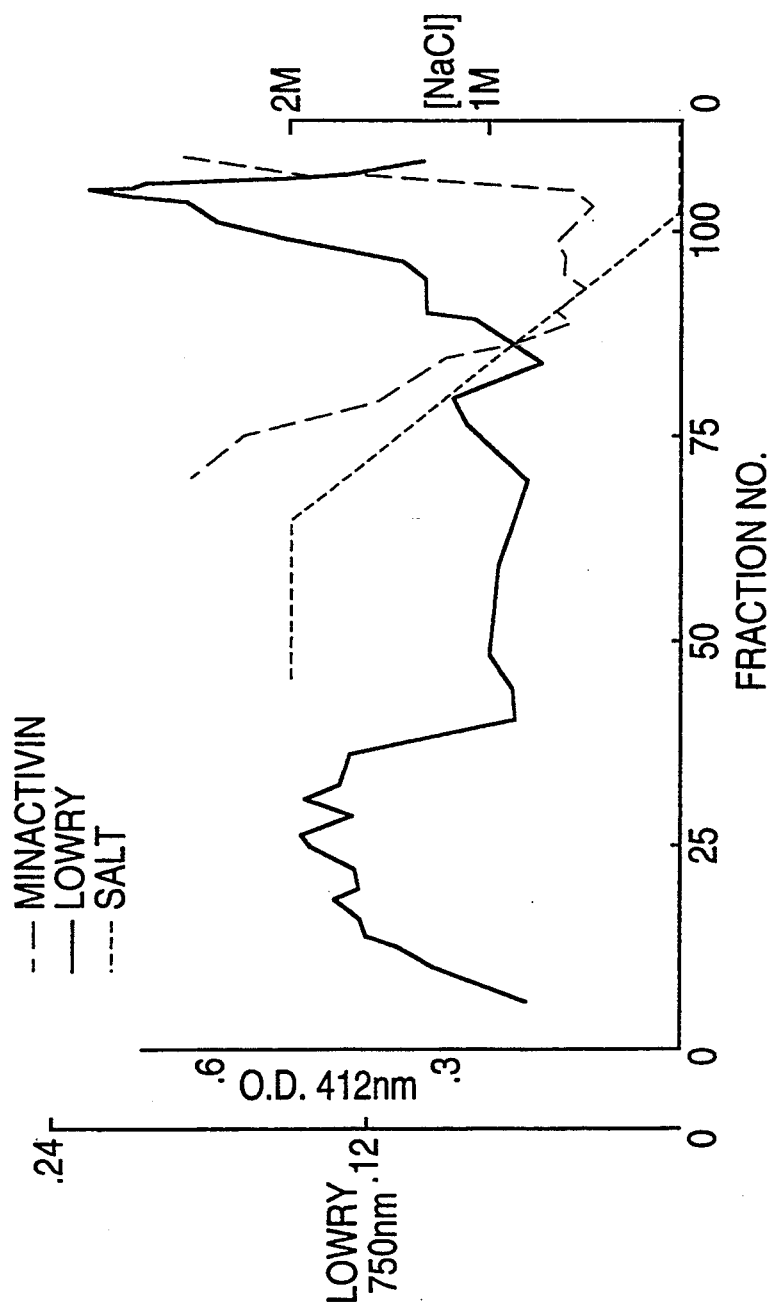

The purified monocytes (typically $5-8 \times 10^8$ cells from 3-4 liters of blood) were adhered to 15 cm plastic dishes (pretreated with gelatin, then human serum and washed) at a density of $0.20-0.34 \times 10^6$ cells/cm$^2$ and cultured with serum-free RPMI-1640 ($0.50-0.75$ ml/$10^6$ cells) containing 0.05 ug/ml of muramyl dipeptide (adjuvant peptide). These cultures were continued for 3 days, after which the media was harvested and clarified by centrifugation. Solid sodium chloride was then added to the supernatant to 2M, and the solution applied to a phenyl-Sepharose affinity (Pharmacia) column at 4° C. The column was washed with two bed volumes of 50 mM glycine, pH 7.8 containing 2M NaCl to remove unbound proteins and then the bound proteins eluted with a descending gradient of NaCl in the same buffer. Fractions from this gradient were assayed for minactivin activity by the method of Coleman and Green (12) and the protein concentrations were determined by Lowry (24). The typical profile for this column is shown in FIG. 14. The most active fractions were pooled, dialysed against 50 mM glycine pH 7.8, and applied (either without further treatment, or after concentration with a Centricon 30 (Amicon)) to an affinity column of Cibacron Blue-Sepharose (Pharmacia) which was equilibrated in the same buffer. Minactivin was not absorbed whereas other protein contaminants were retained by this column. The overall purification achieved by this procedure was of the order of 1000 fold, based on protein concentration (Lowry method) and titration of minactivin activity by colorimetric assay of urokinase inhibition. The interaction between the minactivin product and urokinase was stoichiometric, as previously observed for the minactivin culture supernatants (see FIG. 8). Although typically the minactivin product contained 200–500 units of minactivin per ml, the minactivin component could not be unequivocally identified after SDS-polyacrylamide gel electrophoresis.

Figure 16:
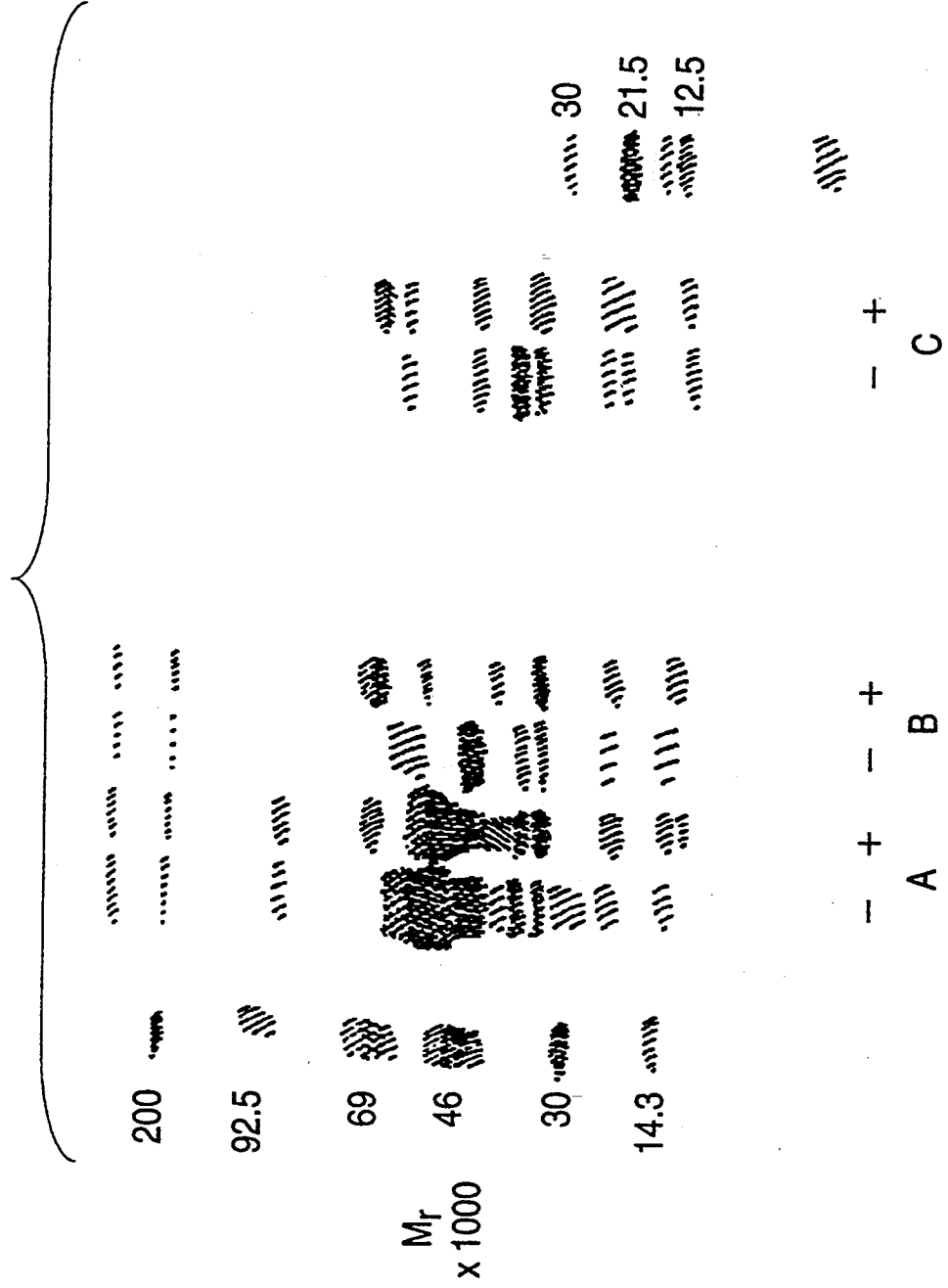

The purification of minactivin by this method was followed by SDS-polyacrylamide gel electrophoresis using in vivo labelled ($^{35}$S-methionine) monocyte preparations in culture. A number of proteins were secreted into the serum-free culture medium over the three day time course and a significant increase in specific activity was obtained following Phenyl-Sepharose chromatography (FIG. 15). Additional protein contaminants are further removed following chromatography on Blue Sepharose (FIG. 16). When urokinase (HPA36) was incubated with these minactivin preparations, a shift in molecular weight was observed yielding a urokinase-minactivin comple corresponding to a $M_r$ of 70–75,000 (FIG. 16). This change in electrophoretic mobility can be used to identify the molecular weight of the protein that is minactivin. The shift correlated with the disappearance of a major protein band in the minactivin preparation of apparent $M_r$ 39–48,000. Minor bands were also observed at $M_r$ 60,000 and 32,000. Under reducing conditions, a single protein band was apparent corresponding to a molecular weight of 30–35,000.

Figure 17:
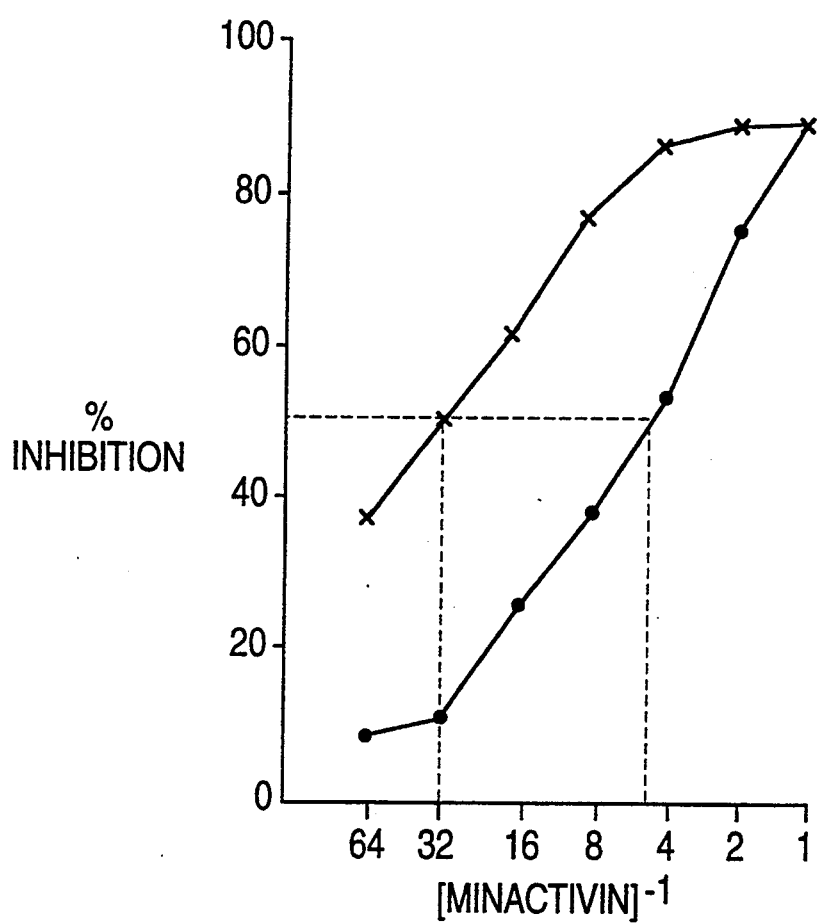

2. Purification of Minactivin from the Human Macrophage Cell Line, U937 Cell Culture The nonadherent human macrophage cell line, U937, was cultured in RPMI 1640 containing 10% foetal calf serum and 1 uM dexamethasone, either in T175 culture flasks or in a 10 liter Braun fermenter. The cells were maintained at densities of $1-3 \times 10^6$ cells/ml. Although minactivin was secreted by the cells during this growth phase, the cells were transferred to serum-free medium to obtain supernatants for minactivin purification. The cells were pelleted, washed once, resuspended in RPMI 1640, containing 1 uM dexamethasone, and cultured for a period of three days. For some of the purification examples given below, 0.7% gelatin was added to the serum-free medium to enhance cell viability. A 4–8 fold increase in minactivin activity was typically obtained in the presence of gelatin (FIG. 17).

The cells were then harvested and the supernatants used in the purification examples which follow. The examples may be used in any combination or order to give a substantially purified minactivin product.

PURIFICATION EXAMPLE 1

Phenyl-Sepharose Chromatography using a Step pH Elution

Figure 18:
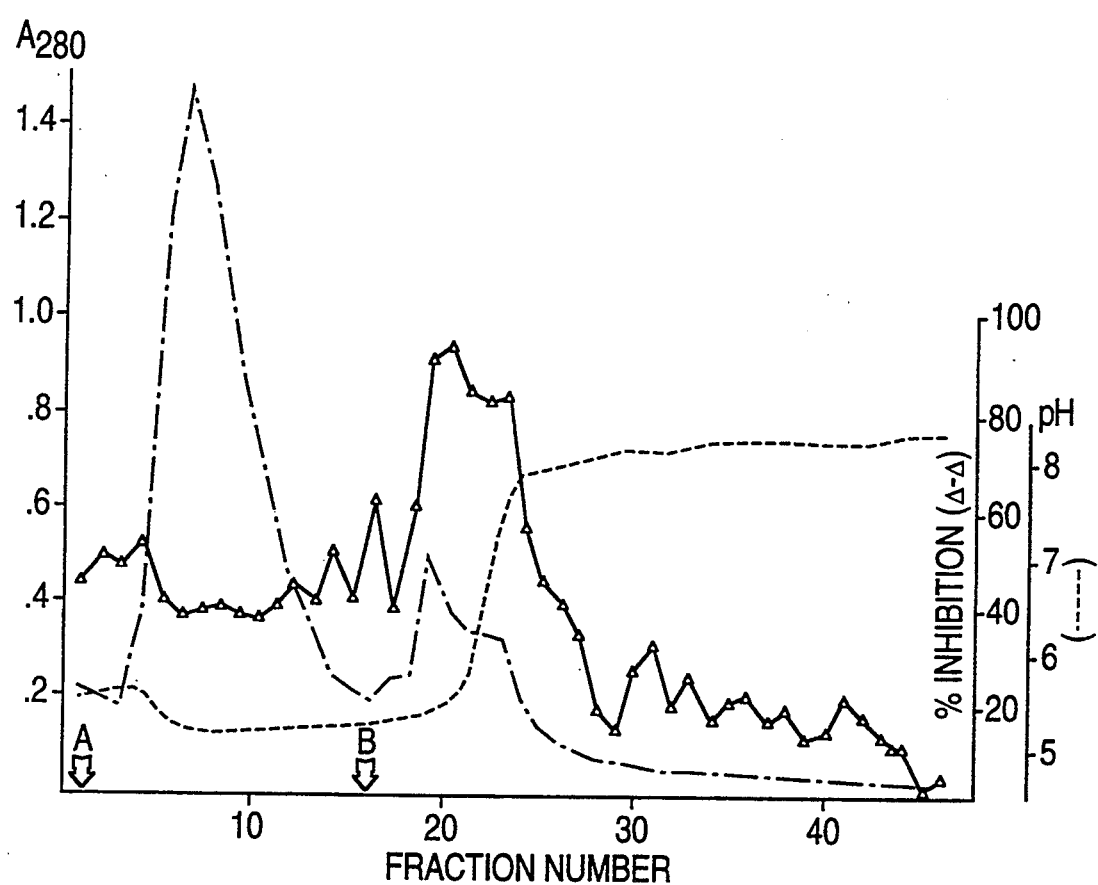

Minactivin was purified from supernatants obtained from U937 cells cultured in the presence of 0.7% gelatin. A 50 ml column of Phenyl-Sepharose was equilibrated with 50 mM citrate, pH 5.5, containing 2M NaCl. 1.6 liters of U937 culture supernatant was adjusted to pH 5.5 with 1M citric acid and solid NaCl added to a concentration of 2M prior to application on the column. The column was then washed thoroughly with the equilibration buffer, and then with 50 mM citrate, pH 5.0, containing 0.5M NaCl. Minactivin was then eluted with 50 mM glycine, pH 7.8, and assayed for activity by the colorimetric method of Coleman and Green (12). Protein content was determined by the Bradford method (25). A typical column profile is shown in FIG. 18.

The yield was 3,360 units of minactivin or 66% having a specific activity of 140 units/mg. This represents a 214 fold increase in specific activity.

PURIFICATION EXAMPLE 2

Batchwise Phenyl Sepharose Chromatography using Salt Elution

Minactivin was purified from supernatants obtained from U937 cells cultured in the absence of gelatin unless otherwise specified.

a) Concentration of Serum Free Minactivin Supernatants

Typically, 4-5 liters of culture supernatant was concentrated 10-fold using an Amicon DC2 Hollow Fiber Dialysis/Concentration unit equipped with a 30,000 MW cut-off cartridge. The concentrate was then dialysed against at least an equal volume of 50 mM glycine, pH 7.8, to remove all traces of dye.

b) Centrifugation of Minactivin Concentrate

The dialysed concentrate was centrifuged in a JA10 rotor at 8,000 rpm for 30 min at 4° C. to pellet residual cell debris and protein that may have precipitated during dialysis. The clarified supernatant is then aliquoted and frozen at −20° C. until required for subsequent purification.

100% of the initial minactivin activity is recovered at this stage, yielding typically 10-20,000 units of minactivin with a specific activity of 20 units/mg.

c) Batchwise Phenyl-Sepharose Chromatography

Minactivin was further purified from the concentrated culture supernatant (obtained from cells cultured in the presence of 0.7% gelatin, specific activity, 1 unit/mg) by batchwise salt elution using Phenyl-Sepharose. The ionic strength of the supernatant (750 mls) was adjusted to 2M with solid NaCl. Phenyl Sepharose which had been pre-equilibrated in 50 mM glycine, pH 7.8, 2M NaCl, was added to the supernatant in a ratio of 1:7.5 (w/v). The suspension was allowed to incubate with agitation for 2 hours at room temperature or overnight at 4° C. The phenyl-Sepharose was removed by filtration under vacuum using a glass-scintered filter, and then washed thoroughly using the same apparatus with the equilibration buffer, followed by buffer containing 50 mM glycine, pH 7.8, 1.4M NaCl to remove contaminating proteins. The minactivin was then eluted from the column with 50 mM glycine, pH 7.8.

The yield of minactivin activity by this method was 4,800 units which corresponds to a 35% yield from the starting material. The specific activity of the minactivin product was increased by approximately 100 fold to 96 units/mg.

PURIFICATION EXAMPLE 3

DEAE-Sepharose Chromatography using Step-wise pH Elution

Figure 19:
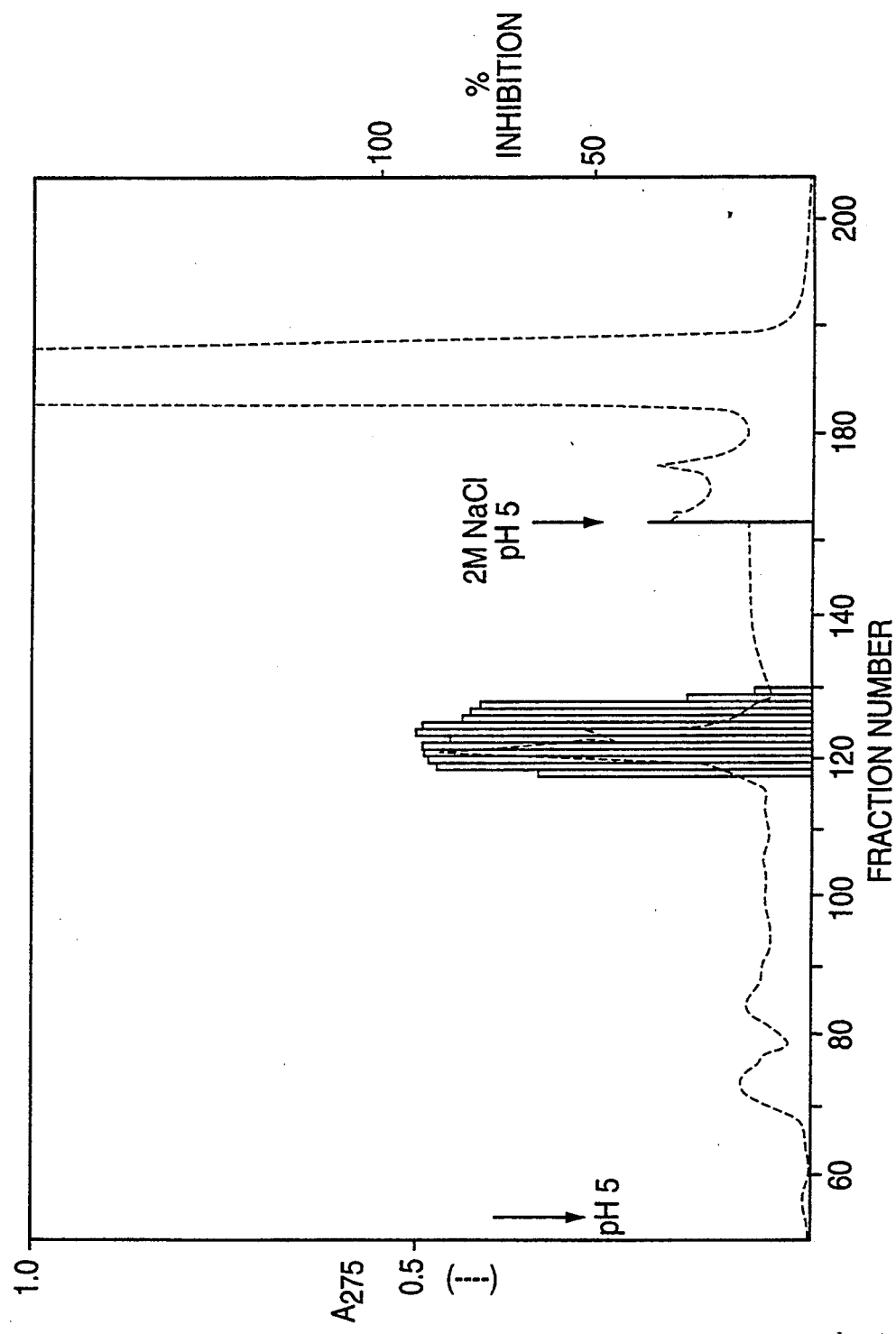

Cell free supernatants were processed through steps (a) and (b) as described in Purification Example 2 using pH elution. The concentrated minactivin supernatant (40 ml, 6.5 units/mg), was applied to a DEAE-Sepharose column which had been pre-equilibrated with 50 mM glycine, pH 7.8. After thorough washing with the equilibration buffer to remove unbound protein, minactivin was eluted using 25 mM citrate-phosphate, pH 5.0. This was followed by a wash with 25 mM citrate phosphate, pH 5.0 containing 2M NaCl to remove any residual protein. A typical column profile is shown in FIG. 19.

The minactivin produced by this method had a specific activity of 63 units/mg and was recovered in a yield of 35%. This represents a 10 fold increase in specific activity.

PURIFICATION EXAMPLE 4

Preparative Nondenaturing Gel Electrophoresis

Figure 20:
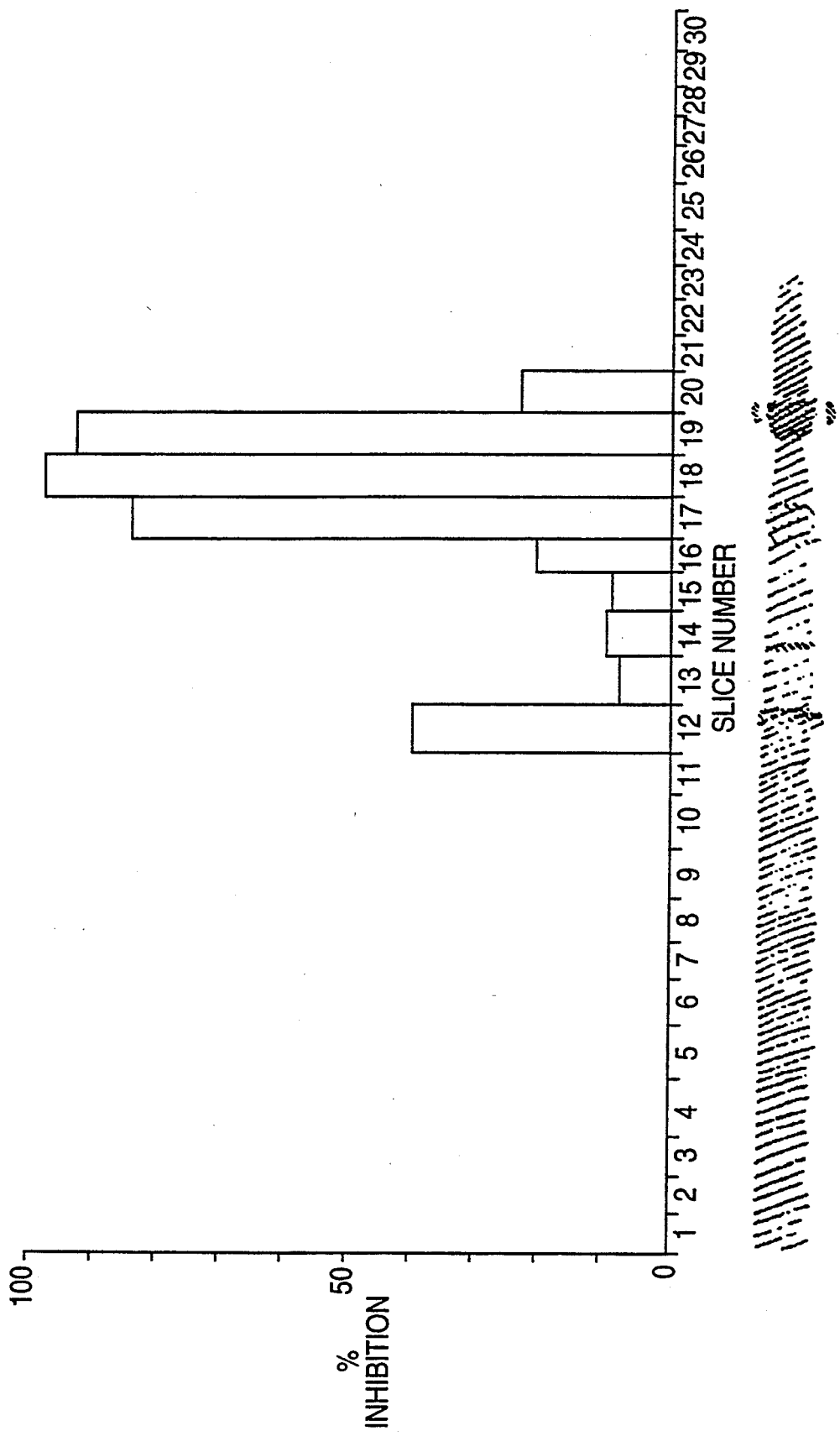

Cell free supernatants were processed through steps (a), (b) and (c) as described in Purification Example 2. Minactivin (3.5 units, specific activity 25 u/mg) and appropriate protein standards were mixed with an equal volume of sample buffer before electrophoresis. The sample buffer consisted of 0.025% bromophenol blue, 0.025% xylene-cyanol, 50 mM Tris HCl, pH 7.5, 18% sucrose and 1% Triton X100. The gel was composed of a 5-15% linear bis-acrylamide gradient and the gel system used was basically that described by Laemmli (26) without the addition of sodium dodecyl-sulphate. 0.15% Triton X100 was substituted for SDS in the running buffer reservoirs only. The sample was applied to the gel and electrophoresed using a constant current of 100 mA. The temperature was maintained below 25° C. using a water-jacketed cooling system. The gel was removed when the tracking dye of lower mobility, xylene-cyanol, travelled the length of the gel. The gel was cut into sections (approximately 0.5×1 cm per track), 150 ul of 50 mM glycine, pH 7.8, was added, and the sample sonicated at 4° C. using a Branson Sonifier cell disrupter for 10-20 seconds at a sonic power of 20. The protein was eluted from the gel sections overnight with constant agitation. The gel was then pelleted by centrifugation of the sample for 10 minutes at 14,930×g, and the supernatant removed for assay of minactivin activity. Duplicate samples were run to allow the protein content to be visualized by silver stain (27) of the appropriate gel track. The results are given in FIG. 20.

The recovery of minactivin from the gel was high: 64% of the initial minactivin activity was recovered after one extraction. An additional 13% was recovered following a second extraction by the same method. The silver stained protein profile shows that the minactivin activity is well separated from a major protein contaminant in the preparation. The specific activity of the minactivin obtained was 2323 units/mg which represents 93 fold purification of minactivin in this step.

PURIFICATION EXAMPLE 5

Blue-Agarose Chromatography

Cell free supernatants were processed through step (a) and (b) described in Purification Example 2. Ten ml of the concentrated supernatant (600U; 20.0 mg; specific activity 30.0) was applied to a 3.2 cm×2.8 cm column of Blue-Agarose equilibrated in 100 mM Na Phosphate, pH 7.0. The column was washed with the same buffer and 8.1 ml fractions collected. Fractions were pooled in groups of seven, dialysed overnight at 4° C. against 50 mM glycine, pH 7.8, and then assayed for protein content and minactivin activity. Minactivin wqas found to elute unretarded from this column and was quantitatively recovered with a four fold increase in specific activity, yielding a value of 120 units/mg.

PURIFICATION EXAMPLE 6

DEAE-Sephacel Chromatography using Salt Gradient Elution

Figure 21:
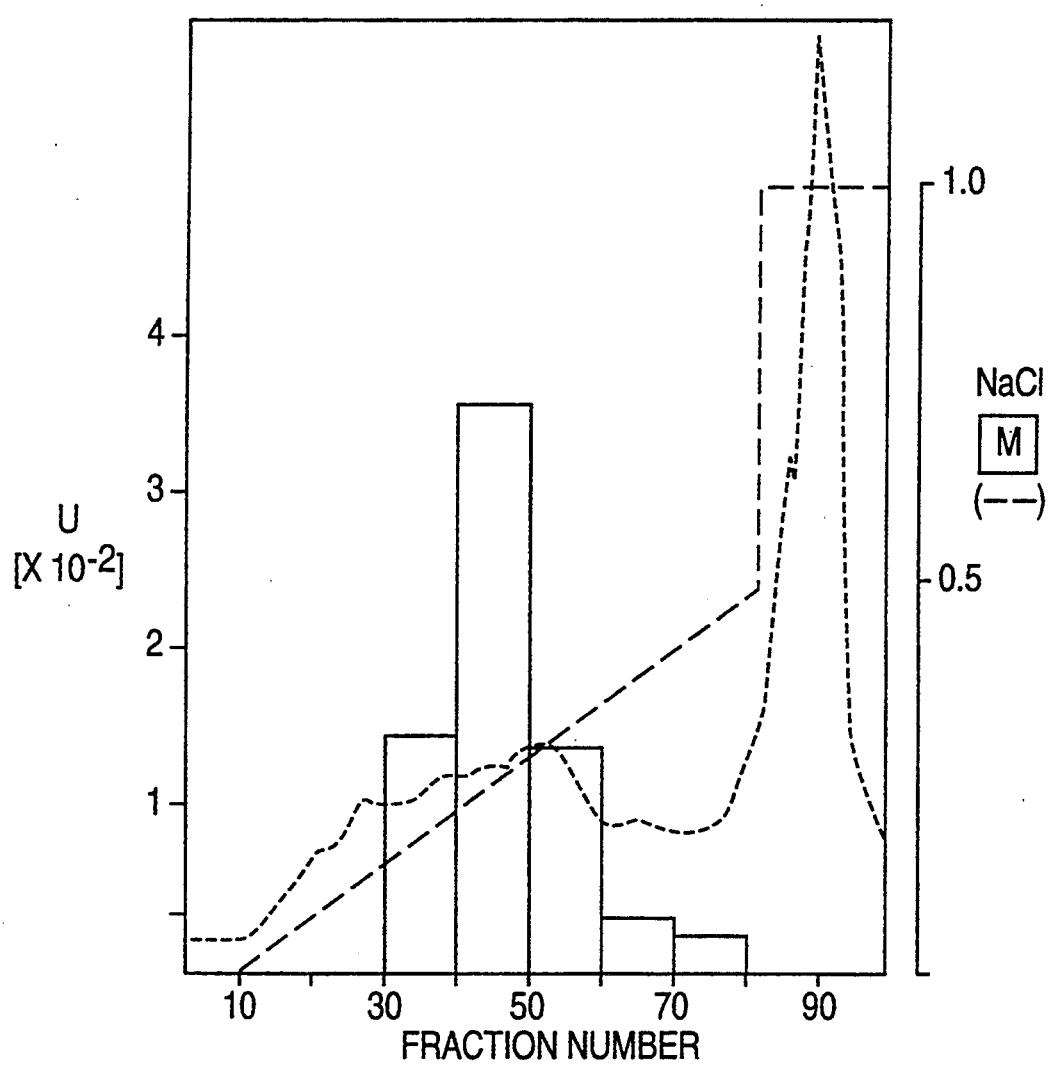

Cell free supernatants were processed through steps (a) and (b) described in Purification Example 2. Ten ml of the concentrated supernatant (640U; 20.0 mg; specific activity 32.0 U/mg) was applied to a 2.6 cm×6 cm column of DEAE-Sephacel equilibrated with 50 mM glycine, pH 7.8. The column was washed with 50 ml of 50 mM glycine, pH 7.8 and then a 500 ml linear gradient of NaCl from 0 to 0.5M in the same buffer applied. Upon completion of the gradient the column was washed with a further 90 ml of 50 mM glycine, pH 7.8 containing 1M NaCl. Fractions of 6 ml were collected. Pools of 10 fractions were made, dialysed against 50 mM glycine, pH 7.8 overnight at 4° C. and assayed for minactivin activity and protein content. The results are shown in FIG. 21. The minactivin eluted at 0.24M NaCl and the peak pools gave 79% recovery with a specific activity of 216 U/mg. This represents a 6.75 fold purification of minactivin.

PURIFICATION EXAMPLE 7

DEAE-Sephacel Chromatography using pH Gradient Elution

Figure 23:
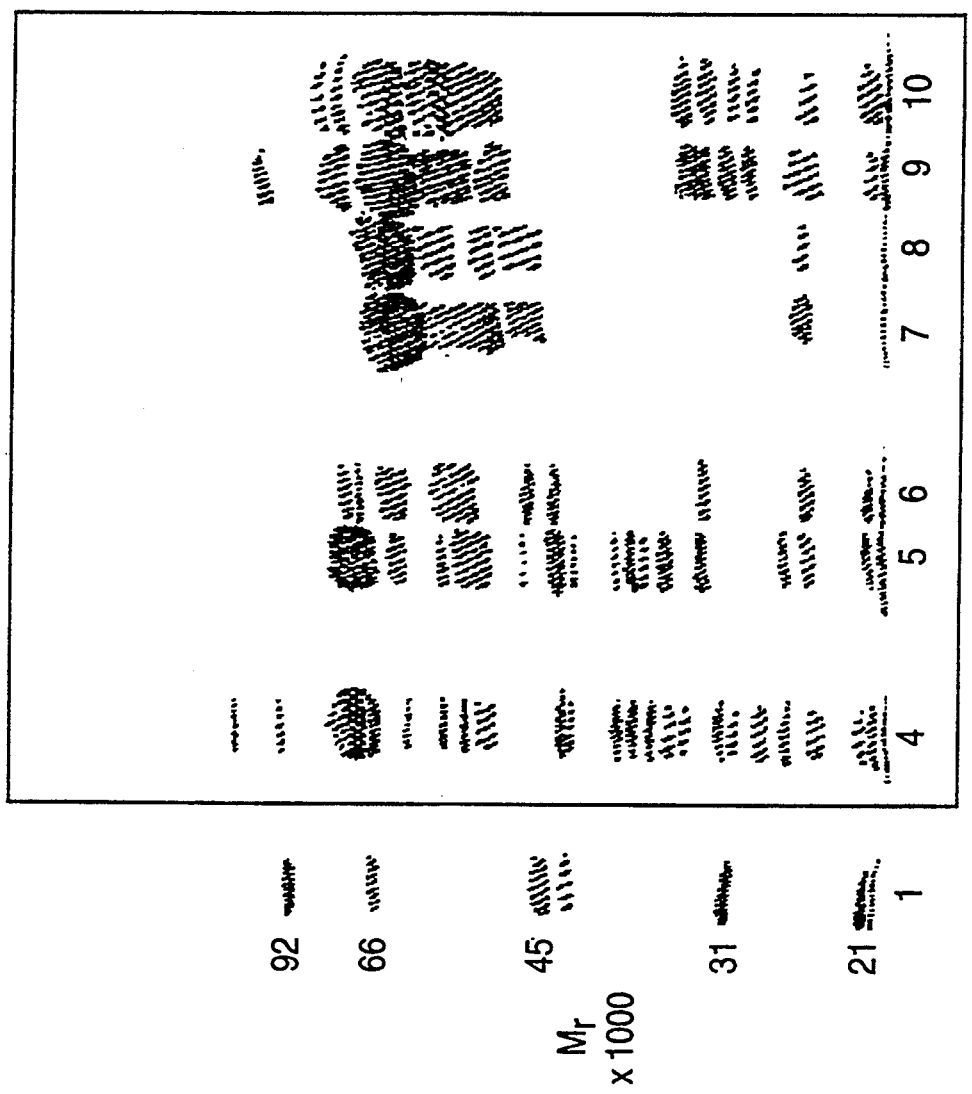

Cell free supernatants were processed through steps (a) and (b) as described in Purification Example 2. Ten ml of the concentrated media (400 U; 20 mg; specific activity 20.0 U/mg) was applied to a 2.6 cm×6 cm column of DEAE-Sephacel equilibrated in 20 mM NH$_4$Ac, pH 6.9. The column was washed with 30 ml of 20 mM NH$_4$Ac, pH 6.9 and then a 500 ml gradient from 20 mM NH$_4$Ac to 20 mM acetic acid was applied to the column to elute the minactivin. Following completion of the gradient the column was washed with 20 mM acetic acid until the absorbance at 275 nm returned to the baseline. Fractions of 5.5 ml were collected. The fractions were pooled in groups of ten and the pH adjusted to between 7 and 8 with NaOH. 5.0 ml aliquots of each pool were dialysed overnight against 50 mM glycine, pH 7.8 at 4° C. and then assayed for minactivin and protein content. The results are shown in FIG. 22. The peak pool of minactivin activity eluted at pH 5.3 and represented 74% of the original material applied to the column. This material had a specific activity of 1966 U/mg which represents a 98 fold purification. An aliquot equivalent to 70 ug of protein was removed from each pool and analysed by SDS-PAGE. The results are shown in FIG. 23.

PURIFICATION EXAMPLE 8

Hydroxylapatite Chromatography

Figure 25:
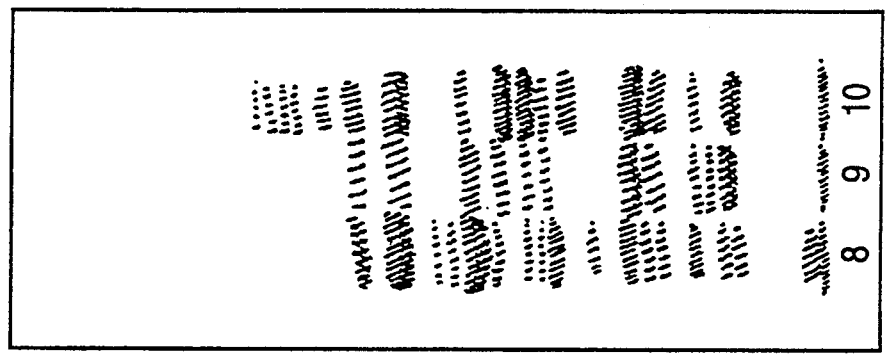

Cell free supernatants were processed through steps (a) and (b) as described in Purification Example 2. Ten ml of the concentrated supernatant (520 U; 16.6 mg; specific activity 31.0 U/mg) was applied to a hydroxylapatite column (2.6 cm×4.5 cm) equilibrated in 50 mM glycine, pH 7.8. The column was washed with 50 mM glycine, pH 7.8 and then a 500 ml gradient from 50 mM glycine, pH 7.8 to 0.5M sodium phosphate, pH 7.0 was applied. The fractions of 5.75 ml were pooled in groups of 10 and aliquots dialysed overnight at 4° C. These aliquots were then assayed for minactivin activity and protein content. FIG. 24 shows that the minactivin eluted at the very end of the gradient and the peak tubes contained 50% of the minactivin applied to the column. This material had a specific activity of 651 U/mg and represents a 21 fold purification. 70 ug aliquots of the minactivin containing fraction were analysed by SDS-PAGE and these are shown in FIG. 25.

EXAMPLE 3

Effect of Minactivin on Tumour Tissue

This example gives the details of the methods used followed by a description of the effect of minactivin on colon tumour cells.

Methods

1. Tissue Samples and Homogenisation

Samples of human colons were obtained immediately after surgical resection. The colonic mucosa was dissected free from muscularis mucosa and washed with Hank's solution. Macroscopically normal mucosa and frank carcinoma were sampled from each colon and stored frozen. Portions of thawed material were later weighed and gently hand homogenised with 50 mM glycine buffer pH 7.8 containing 0.5% Triton X100, using 10 ul of buffer per mg (wet weight) of tissue.

2. Colorimetric Assays of Plasminogen Activators

The plasminogen activator content of tissue homogenates and cell culture supernatants were quantified by the assay method of Coleman and Green (12) as described in Example 1. Homogenates prepared as above were diluted 1:10 with homogenising buffer prior to assay.

3. SDS-PAGE and Fibrin Overlay Zymogram

The method of Granelli-Piperno and Reich (13) was used for this separation technique as described in Example 1. The tissue homogenates were applied to the non-reducing 11% acrylamide gel either (a) without further treatment, (b) after incubation for 30 min at 37° with affinity purified human plasminogen, (c) after incubation for 90 min at 23° with monocyte minactivin, or (d) after incubation first with plasminogen, and then with minactivin. Untreated samples of the above incubations (60 ul) were applied to the gel with SDS sample buffer (40 ul).

4. Radial Diffusion Assays

Radial diffusion assays were performed as described in Example 1. The proteases used for the incubations were kallikrein (1.5 ug), plasmin (150 ng), mouse urokinase (2.5 mPU), HPA66 (melanoma culture supernatant), human urokinase (12.5 mPU) and COLI 394 supernatant (containing 1.3 mPU HPA52). These enzymes were incubated with excess minactivin for 90 min at 23°, then applied to the wells in the diffusion gel.

5. Culture of Colon Carcinoma Cells

The human colon carcinoma cell line COLO 394 (28) was cultured in RPMI-1640 supplemented with 10% foetal calf-serum and passaged twice a week.

For studies of the effect of minactivin and tumour cell culture enzyme, approx. $3 \times 10^6$ cells/well were plated in 6-place multi-well plates (Linbro No. 76-058-05). After adherence overnight, the cells were washed and cultured with serum-free RPMI 1640 for 48 hours. Additions to the three experimental cultures were 1) human plasminogen (15 ug/ml, 2) plasminogen plus minactivin (equivalent to 1 PU of urokinase) or 3) plasminogen, minactivin and trasyol (18 ug/ml).

6. Minactivin Preparation

Minactivin used in these experiments was prepared from human blood monocyte culture supernatants as described in Example 6. Adherent monocyte cultures on plastic dishes were cultured for 3 days with RPMI 1640 containing 0.05 ug/ml of muramyl depeptide.

Results

Effect of Minactivin on Tumour Tissue Homogenates

1. Comparison of the Plasminogen Activator Content of Normal and Tumour Colon Tissues
   a) Colorimetric Assay Diluted homogenates of colon mucosa were assayed for plasminogen activator by the method of Coleman and Green (12). This assay measures the total content of plasminogen activator enzyme (i.e. proenzyme and activate enzyme) because the plasminogen substrate used contains trace amounts of plasmin sufficient to activate proenzyme. Direct hydrolysis of the lysine thioester plasmin substrate by plasminogen-independent neutral proteases in the diluted homogenates did not contribute significantly to colour development. Both histologically normal areas of cancer-bearing colons, and frank color cancer tissue were assayed for plasminogen activator activity as shown in FIGS. 26A and 26B.

The activity of normal tissue homogenates was tightly centred, with a mean value of $0.51 \pm 0.16$. While only a small minority of samples showed active urokinase bands of SDS-PAGE fibrin overlay (see below), the more sensitive colorimetric assay showed that all homogenates of normal tissue contained some plasminogen activator contributing to this assay. In the absence of added fibrin, it seems most likely this contribution was from low levels of urokinase-type plasminogen activator (HPA52) and not from the ubiquitous tissue-type plasminogen activator (HPA66) (29).

Figure 27:
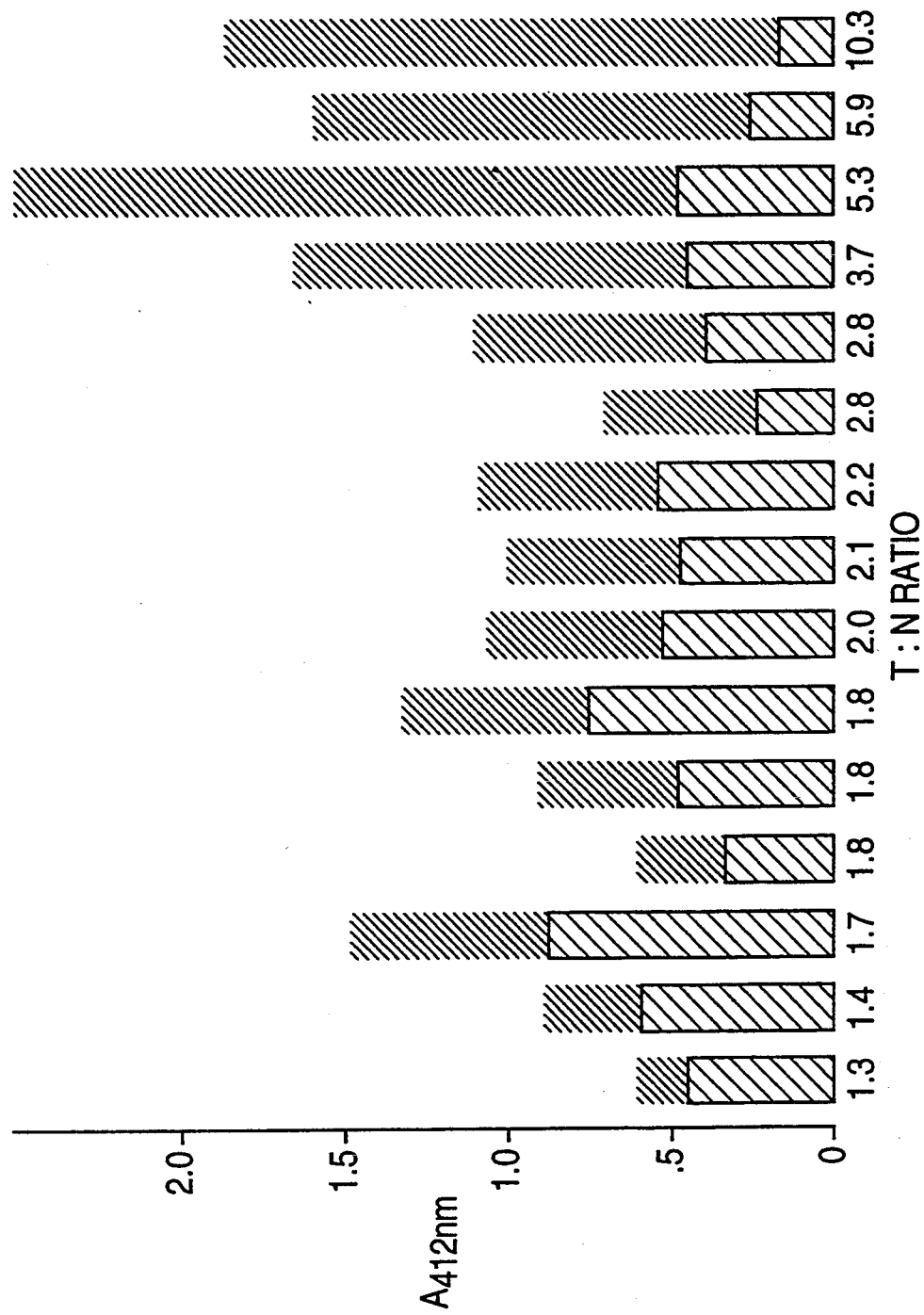

Tumour homogenates, however, showed a wide spectrum of plasminogen activator activity, covering a ten fold absorbance range. The mean absorbance was $1.15 \pm 0.56$, more than double that of the mean for normal tissue homogenates. This ratio however included all material sampled, and if instead the tumour samples were paired with the corresponding samples of normal tissue from each colon (FIG. 27), the mean ratio increased to over three, with some pairs having a ratio of greater than five.

b) SDS-PAGE and Fibrin Overlay

Homogenates of colon mucosa from histologically normal areas of tumour-bearing colons typically produced only one major band of lysis on fibrin-agarose zymograms after SDS-PAGE which corresponded to the tissue-type plasminogen activator (HPA66) of human melanoma culture supernatant (FIG. 28A).

Minor bands were present at molecular weights of approximately 96,000 and 110,000. However, some homogenates of normal tissue also produced a lysis band corresponding to the high molecular weight form of urokinase, i.e. HPA52 (see below). If undiluted homogenates of typically normal colon were incubated with human plasminogen in the assay buffer, some activation of plasminogen occurred and a plasmin band appeared on the zymogram at $M_r$ 85,000 (FIG. 28A, lane 2). HPA66 activity progressively disappeared when samples were removed following a 2 hour incubation with plasminogen. The minor bands at 96,000 and 110,000 also disappeared rapidly.

Homogenates of cancer tissue typically produced a major band of HPA52, with a second band of HPA66 of varying relative intensity (sometimes almost absent) (FIG. 28B). The other minor bands noted above were usually very weak or absent. Pre-incubation with plasminogen resulted in the gradual disappearance of HPA66 after 2 hrs at 37° (FIG. 28B, lanes 2–4). The plasmin produced (lysis at $M_r$ 85,000) then effected the conversion of HPA52 to its active cleavage products with $M_r$ of approx. 33–36,000.

EXAMPLE 4

Interaction of Minactivin with Urokinase-type Plasminogen

1. Activators in Colon Mucosa Homogenates

Treatment of normal colon tissue homogenates with minactivin before electrophoresis had no effect on the lysis band produced by the tissue-type plasminogen activator, HPA66, but led to the loss of nearly all of the minor activity band of HPA52 (FIG. 29A).

Preincubation of the homogenate with plasminogen produced plasmin, which diminished the HPA52 band and led to the appearance of trace bands representing its active degradation products of $M_r$ 33–36,000. When the preincubation with plasminogen was followed by treatment with minactivin, the HPA52 band and the trace bands at 33–36,000 were abolished.

Figure 29B:
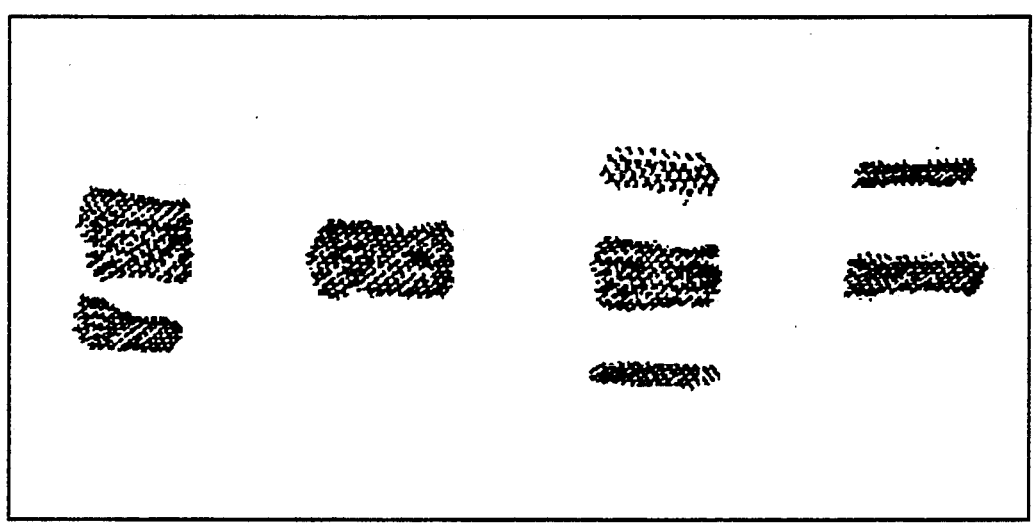

Tumour tissue homogenates produced prominent HPA52 lysis bands which were diminished by incubation with minactivin (FIG. 29B). Pretreatment with plasminogen before electrophoresis produced plasmin and this in turn converted the HPA52 to HPA33–36 as observed previously for the normal tissue homogenate. Thus, although minactivin had no effect on HPA66, the enzymes in homogenates of both tumour colon tissues and those normal colon tissues which produced bands of $M_r$ 52,000 were similarly affected by incubation with human monocyte minactivin. If the homogenates were treated initially with plasminogen and then with minactivin, the HPA52 band normally seen after electrophoresis essentially disappeared and the bands representing HPA33–36 were abolished (FIG. 29B). Thus, it is apparent that inactivation of HPA52 by minactivin following plasminogen treatment is considerably more effective than that observed in untreated homogenates. This suggests that the predominant form of the HPA52 occurring in tissues is in fact the proenzyme, and that reaction with minactivin is dependent on its conversion to active enzyme, probably by means of plasmin.

Figure 30:
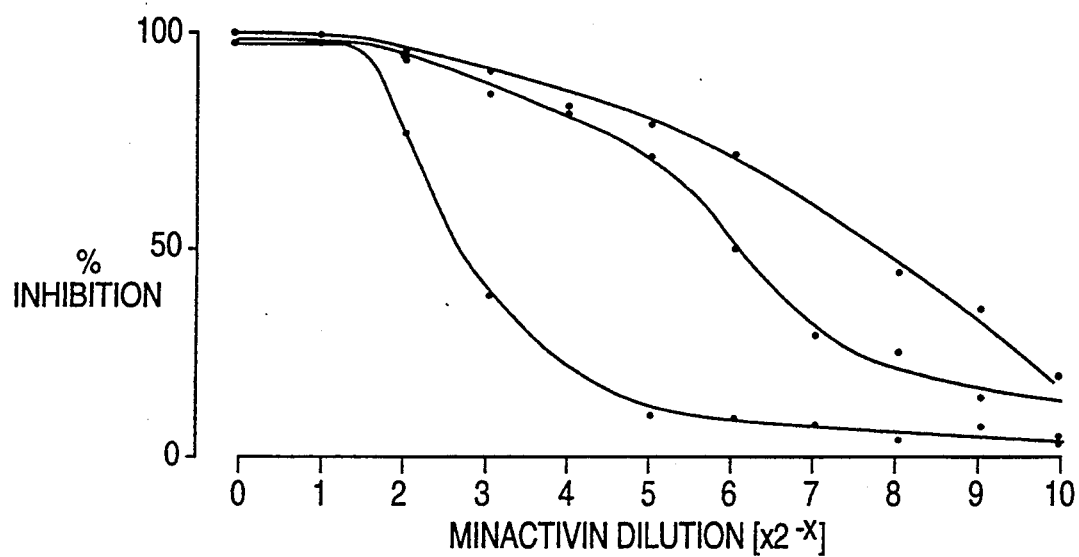
Figure 31:
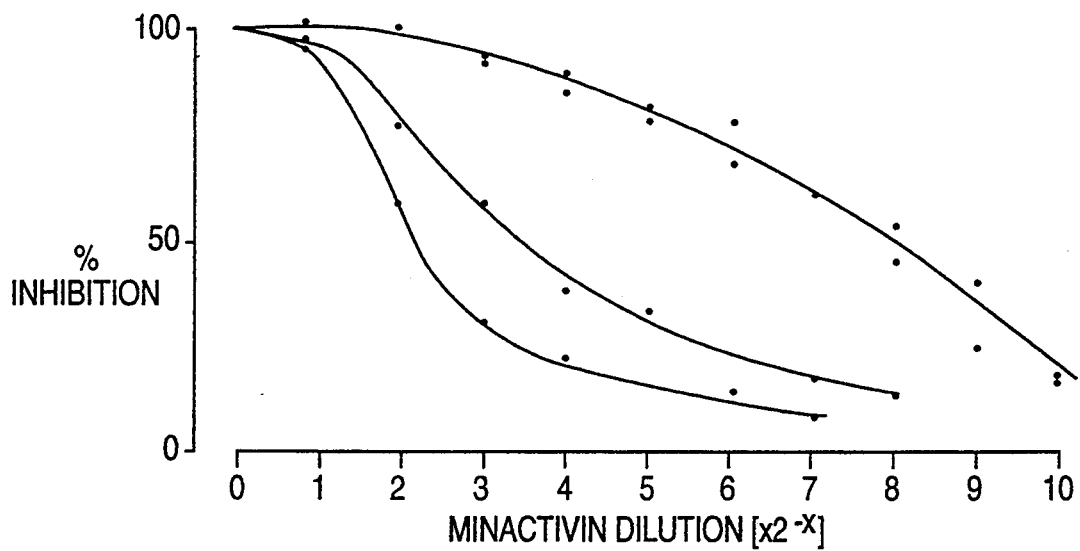

2. Specificity of Minactivin with Respect to the Proenzyme Form of Urokinase-type Plasminogen Activator Colorimetric Assays The stoichiometric relationship between minactivin and urokinase holds over a wide range of urokinase concentrations, from 10 mPU to 1000 mPU (FIG. 30). However, titration of the minactivin inhibition of plasminogen activator in dilute homogenates of colon mucosa did not exhibit this characteristic feature (FIG. 31). Indeed, more minactivin was required to inhibit the low level of activity of HPA 52 in normal tissue than to inhibit the much enhanced activity in tumour tissue homogenates. This is consistent with the presence of the proenzyme form of HPA52 in the tissue homogenates.

Figure 33:
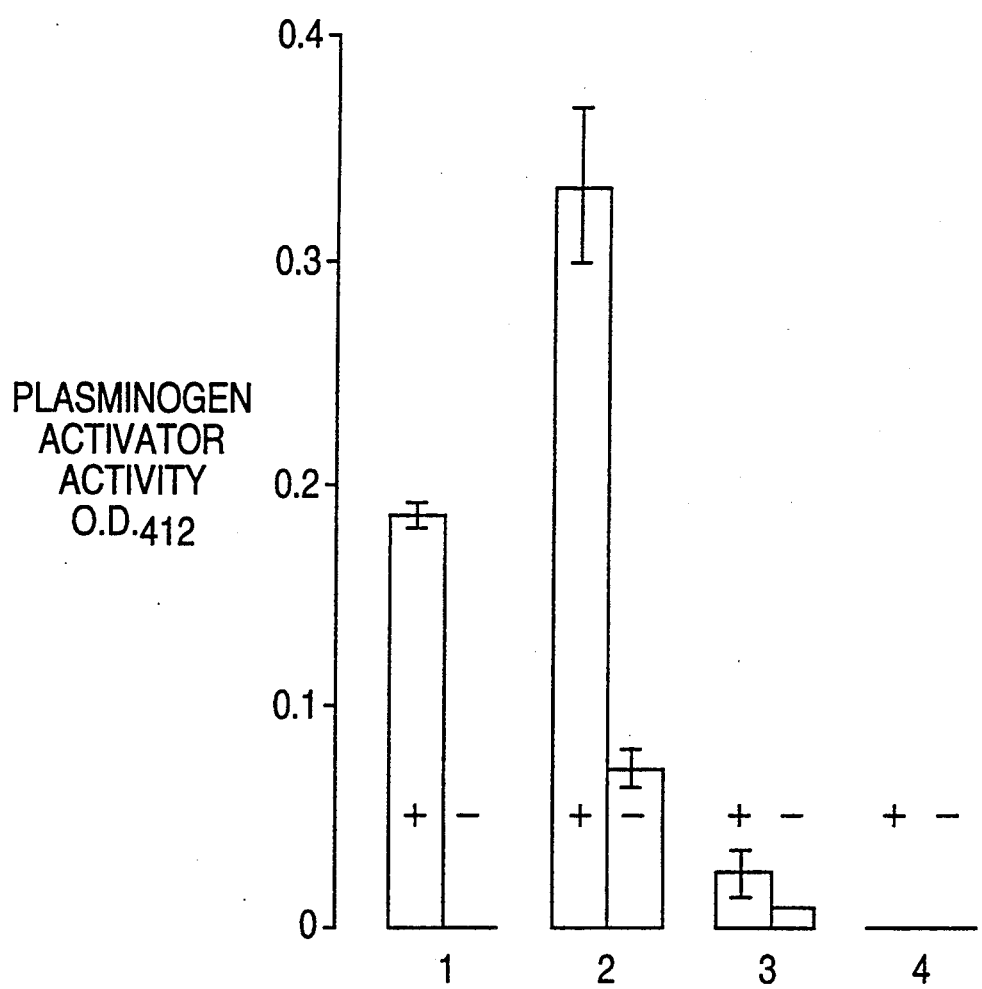

The presence of this HPA52 proenzyme can be demonstrated using serum free supernatants from cultures of the transformed colon tumour cell line COLO394. The plasminogen activator secreted by this cell line consists principally of HPA52 with some other higher $M_r$ bands, presenting a very similar pattern to the tumour tissue homogenates above (FIG. 32). When plasminogen was included in the culture media, some plasmin was produced (shown by colorimetric assay, FIG. 33) which precipitated the conversion of some HPA52 to HPA36. If minactivin and plasminogen were added to the media, all the plasminogen activator produced during the culture was inactivated, as shown by both SDS-PAGE and fibrin overlay development (FIG. 32) and colorimetric assay (FIG. 33). However, if trasylol, a rapid and potent inhibitor of plasmin, was added to cultures together with plasminogen and minactivin, no inactivation occurred (FIG. 32). Since trasylol does not directly affect the reaction between minactivin and urokinase, these results showed that the HPA52 produced by COLO 394 was in the proenzyme form, requiring plasmin for expression of activity and for reaction with minactivin. In the SDS-PAGE fibrin overlay system, activation occured due to the traces of plasmin present in the plasminogen substrate. This did not occur when plasmin was inhibited by trasylol.

These results demonstrate that several major human carcinomas produce significantly greater amounts of urokinase-type plasminogen activator than that occurring in adjacent uninvolved tissue. Minactivin is capable of at least partially inhibiting HPA52, a human urokinase-type plasminogen activator, when added directly to tissue homogenates. This inactivation is specific for the urokinase-type plasminogen activator, HPA66. It is further established that minactivin does not affect the proenzyme form of HPA52, but that protease activity (in this case provided by plasmin) is required for the conversion of HPA52 to an active form before it is available to react with minactivin.

EXAMPLE 5

Minactivin activity was measured by a modification of the method of Coleman and Green N.Y. Acad. Sci. 370, 617 (1981), as described by Stephens et al Eur. J. Biochem. 136, 517-522 (1983), in which the inhibitory activity of minactivin was determined by quantifying the loss of urokinase activity in the colorimetric assay using a urokinase reference standard (Calbiochem). The minactivin samples were preincubated with 4 mPU urokinase for 90 minutes at 23° C. before the addition of plasminogen. One unit of minactivin activity was defined as that amount which inhibited 1 Plough wait of urokinase. Human urokinase was purchased from Calbiochem Behring Corp., La Jolla, Calif. Plasminogen was purified from fresh human plasma by lysine-sepharose (Pharmacia) affinity chromatography (Unkeless, J. C. et al (1974), J. Biol. Chem. 249, 4295–4305).

The protein concentration was determined according to the method of Bradford, M. M., Anat. Biochem. 72, 248–254 (1976) using bovine serum albumin as the standard. Specific activity is defined as the minactivin activity as measured by colorimetric assay divided by the protein concentration.

Proteins were separated by SDS-polyacrylamide gel electrophoresis using 11% Laemmli gels (Laemmli, U. K., Nature 227, 680–685, 1970) or on SDS-urea-gradient polyacrylamide gels using a modified Laemmli buffer system as described by Mattick, J. S. et al Eur. J. Biochem. 114, 643–651 (1981). Western (transfer) blotting was performed by electrophoretic transfer to nitrocellulose as described previously (Towbin, H. et al, Proc. Natl. Acad. Sci. USA, 76, 4350–4354 and Johnson, D. A. et al, Gene Anal. Tech. 1, 3–8, 1984).

Cell Culture

The human macrophage cell line, U937, was cultured in RPMI 1640 containing 10% foetal calf serum and 1 micromolar dexamethasone, either in T175 culture flasks or in a 10 liter Braun fermenter. The cells were maintained at densities of $1-3 \times 10^6$ cells/ml. Although minactivin was secreted by the cells during this growth phase, the cells were transferred to serum-free medium to obtain supernatants for minactivin purification. The cells were pelleted by low speed centrifugation, washed by resuspension in phosphate buffered saline and recentrifugation and then resuspended in serum free RPMI 1640 containing 1 micromolar dexamethasone, and cultured for a period of three days. The level of minactivin secreted by these cells under serum free conditions could be enhanced by approximately an order of magnitude to 0.4% with the addition of PMA.

The cells were then harvested and the supernatants used in the purification scheme which follows.

EXAMPLE 6

Purification of Homogeneous Minactivin a) Concentration of Serum Free Minactivin Supernatants Typically, 4 to 5 liters of culture supernatant was concentrated 10-fold using an Amicon DC2 Hollow Fiber Dialysis/Concentration unit equipped with a 30 000 MW cut-off cartridge. The concentrate was then dialysed using the DC-2 Hollow fibre unit by repeated concentration and dilution using at least an equal volume of 50 mM glycine pH 7.8 for 3 to 6 hours at room temperature, to remove all traces of dye.

b) Centrifugation of Minactivin Concentrate

The dialysed concentrate was centrifuged in a JA10 rotor at 8000 rpm for 30 min at 4° C. to pellet residual cell debris and protein that may have precipitated during dialysis. The clarified supernatant is then aliquoted and frozen at −20° C. until required for subsequent purification.

c) Phenyl-Sepharose Chromatography using a Step pH Elution

Minactivin was further purified from ten-times concentrated culture supernatant obtained from cells cultured in the absence of PMA by step pH elution using phenyl-sepharose as follows.

The ionic strength of the supernatant (200 ml; 12000 units; specific activity 102 units/mg) was adjusted to 2M by the addition of solid NaCl and the pH adjusted to 5.5 with citric acid. This solution was applied to a phenyl-sepharose column (4.4 cm × 5.0 cm) equilibrated in 50 mM Na citrate, pH5.5, 2M NaCl and 1 mM EDTA and eluted with the same buffer until the baseline absorbance at 280 nm (A280) returned to baseline. The column was then eluted with 50 mM sodium citrate, pH5.5 containing 0.5M NaCl and 1 mM EDTA and again the A280 monitored until the absorbance returned to baseline. The minactivin was then eluted from the column with 50 mM glycine, pH9.0. FIG. 47 shows the elution profile.

The recovery of minactivin by this method was 9553 units which represents 80% of the units applied to the column. The material of highest specific activity was pooled (6700 units; specific activity 1343 units/mg) and concentrated to 3 ml on an Amicon YM10 membrane.

d) Sephacryl S-200 Gel Permeation Chromatography

The pooled, concentrated minactivin was applied to a 2.2 cm×78 cm column of Sephacryl S-200 equilibrated with 0.1M sodium borate, pH9.0. Fractions of 5.0 ml were collected at a flow rate of 0.46 ml/min. FIG. 41 shows that minactivin was eluted at the tailing edge of the major protein peak. The fractions containing minactivin activity were pooled (4480 units; specific activity 1355 units/mg) and concentrated to 3 ml using a YM10 membrane. Calibration of this column with known $M_r$ standards indicated that minactivin had an $M_r$ of 45–48 kD.

e) Isoelectric Focussing

The concentrated minactivin solution was applied to a preparative flat bed gel of Ultrodex containing Ampholines in the pH range 4.5–6.0 and electrofocussed for 23 hrs at 10° C. on an LKB Multiphor isoelectric focussing apparatus. Following completion of the run, 30 zones across the length of the gel were scraped out and the protein eluted from each with 10 ml of 1M glycine containing 1 mM EDTA, pH9.0. Aliquots of each fraction were assayed for minactivin activity and electrophoresed on 15% SDS-polyacrylamide gels to locate protein. FIG. 48 illustrates that a significant amount of protein has been removed from the fractions containing the minactivin activity. Under these conditions minactivin focusses between pH5 and pH5.2 and within this region of the gel 15% of the total activity applied to the gel was recovered.

In fact, in the region of the isoelectric focussing gel containing minactivin activity, only two protein bands are visible (FIG. 48). To determine which of these bands is minactivin the protein on an equivalent polyacrylamide gel was transferred onto nitrocellulose and probed with antibodies made in goat to placental inhibitor. Due to similar biological properties it was considered likely that the two proteins would be immunologically related. As shown in FIG. 49 the protein band of $M_r = 45$–$48$ kD specifically cross reacts with the anti-placental inhibitor antibodies suggesting that this protein band is minactivin. Furthermore, this observation is consistent with the $M_r$ of 45–48 kD determined for native minactivin on gel permeation chromatography.

f) High Pressure Liquid Chromatography

The fractions from the isoelectric focussing above which contained minactivin activity were concentrated 10-fold on an Amicon YM10 ultrafiltration membrane and further fractionated on a Vydac C-4 reverse phase column using a Waters high pressure liquid chromatograph. The proteins were eluted from the reverse phase column using a gradient of acetonitrile in 0.1% TFA as shown in FIG. 50. Each of the absorbance peaks was examined by SDS-PAGE and peak 5 was found to contain pure minactivin (FIG. 51).

EXAMPLE 6A (a) Gel Filtration

Cell free supernatants were processed through steps (a) and (b) as described in Purification Example 2 of WO86/01212, and then through Phenyl-Sepharose using a step pH elution as described in Purification Example 1 of WO86/01212. The fractions containing minactivin activity were pooled, concentrated by precipitation with 85% saturated ammonium sulphate and applied to a 2.2 cm×80 cm column of Sephacryl S-200 equilibrated in 0.1M sodium borate, pH9.0. Fractions of 3.5 ml were collected at a flow rate of 0.46 mg/min. FIG. 41 shows that minactivin was eluted at the tailing edge of the major protein peak and had a peak specific activity of 2206 Units/mg representing an overall increase in specific activity of 31 fold. Under these conditions the minactivin behaves as a molecule with a Stokes radius similar to ovalbumin, suggesting a molecular size of 45–49×10³ daltons.

(b) Phenyl-Boronate Agarose Chromatography

Cell free supernatants were processed through steps (a) and (b) as described in Purification Example 2 of WO86/01212. One ml of the supernatant was made to 10 mM in MgCl$_2$ and the pH then adjusted to pH8.5 with sodium hydroxide. This solution was applied to a column of phenyl-boronate agarose —30 (PBA 30) (0.8 cm×2.5 cm) equilibrated in 50 mM glycine, pH8.5 containing 10 mM MgCl$_2$ at 4° C. The column was then washed with 9 ml of the above buffer and then serially as follows:

a) 10 ml of 50 mM glycine, pH8.5 containing 10 mM EDTA b) 10 ml of 50 mM glycine, pH8.5 containing 100 mM sorbitol c) 10 ml of 100 mM Tris-HCl, pH8.5 d) 10 ml of 50 mM sodium acetate, pH5.0.

Fractions of 5 ml were collected and dialysed against 50 mM glycine, pH7.8 overnight at 4° C. prior to minactivin activity and protein determinations. The results shown in FIG. 42 illustrate that two distinct peaks of activity elute from the column under different conditions. The first peak, eluted with EDTA, contains 35% of the total activity loaded onto the column with an increase in specific activity of 14 fold. The second peak represents 32% of the initial activity with a 4.4 fold increase in specific activity.

(c) Chromofocussing

Cell free supernatants were processed through steps (a) and (b) as described in Purification Example 2 of WO86/01212. Four ml of this supernatant was dialysed against 25 mM imidazole-HCl buffer, pH7.4 overnight at 4° C. and then applied to PBE 94 chromofocussing column (1 cm×27 cm) equilibrated in the above buffer. A linear pH gradient was then established by applying 200 ml of polybuffer pH4.0 and 4 ml fractions were collected into 4 ml aliquots of 1M Tris.HCl, pH7.5. Every 10 fractions were pooled, concentrated and washed on a centricon 30 and assayed for minactivin activity and protein concentration. FIG. 43 shows that the majority of the activity eluted near pH5. The overall recovery of activity was 82% and there was a 2 fold increase in specific activity.

(d) Isoelectric Focussing

Cell free supernatants were processed through steps (a) and (b) as described in Purification Example 2 of WO86/01212, and then through phenyl Sepharose using a step pH elution as described in Purification Example 1 of WO86/01212. The fractions containing minactivin activity were pooled, concentrated by precipitation with 85% saturated ammonium sulphate and dialysed overnight against 50 mM glycine pH9.0. This solution was applied to a preparative flat bed gel of Ultrodex containing Ampholines in the pH range 4.5–6.0 and electrofocussed for 23 hrs at 10° C. on an LKB Multiphor isoelectric focussing apparatus. Following completion of the run, 30 zones across the length of the gel were scraped out and the protein eluted from each with 10 ml of 1M glycine containing 1 mM EDTA, pH9.0. Aliquots of each fraction were assayed for minactivin activity and electrophoresed on 15% SDS-polyacrylamide gels to locate protein. FIG. 44 illustrates that a significant amount of protein has been removed from the fractions containing the minactivin activity. Under these conditions minactivin focusses between pH5 and pH5.2 and within this region of the gel 39% of the total activity applied to the gel was recovered.

(e) Immunoaffinity Chromatography

Cell free supernatants were processed as through Purification Example 1. A 4.6 ml aliquot of this minactivin preparation (2300 Units, 2.25 mg, specific activity 1020 U/mg) was made 0.05M in sodium phosphate, 0.5 in NaCl, 0.01% in TritonX-100, 0.1% in sodium azide, 1 mM in EDTA and the pH adjusted to 7.5. This solution was diluted to 15 ml with the above buffer and added to 15 ml of Sepharose 4B to which 10 mg of anti-placental inhibitor antibody had been chemically coupled using the 1,1'-carbonyl-diimidazole method of Bethell, G. S. et al J. of Biol. Chem. 254 (8) 2572–2574 (1979). The slurry was shaken overnight at 4° C. and then poured into 2.5 cm×3.1 cm column. Unbound protein was drained from the column and the column washed with the above buffer until the absorbance at 280 nm returned to baseline. The column was then eluted with 3M KSCN containing 10 mM Tris, HCl, pH8.0. The elution profile is shown in FIG. 45. The fractions eluted by the KSCN were concentrated 8.5 fold on a Centricon 10, washed with 40 mM glycine, ph7.8 and analysed for minactivin activity and by SDS-PAGE. The majority of the minactivin activity did not bind to the antibody column. However, a small amount of minactivin activity (8.5 units) is bound specifically and is eluted with 3M KSCN. This indicates that under these conditions the antibody column has been overloaded with minactivin. Furthermore, minactivin loses over 90% of its activity in the presence of KSCN over a comparable period of time suggesting that the low recovery of minactivin activity may be due to inactivation of the molecules in KSCN. The SDS-PAGE results show that the vast majority of the protein elutes unretarded from the column. The KSCN eluate however contains a major protein band of molecular weight ca 45 000, similar to the molecular size of minactivin on gel filtration (see Example 2A(a)) (FIG. 45A). Western analysis of this minactivin preparation showed a single immunologically cross reactive species migrating identically with the protein band observed following SDS-PAGE (FIGS. 45B and 45C).

Under certain conditions, minactivin has been observed to have a molecular size of approximately 60–70,000 (as detailed in PCT191-85). This discrepancy may be due to altered mobility due to the degree of glycosylation of minactivin.

EXAMPLE 7

Isolation and Sequence of Peptide Fragments from Minactivin

Minactivin was purified from PMA induced U937 cells as described in Example 2 above. The minactivin (3–5 μg) was then digested with endoproteinase Lys C (0.1 μg) in 20 mM Tris-HCl, pH 8.5 containing 5M Urea in a final volume of 50 μl for 8h at 22° C. The resultant peptides were separated by reverse phase high pressure liquid chromatography on a Synchropak RP-P (C-8) column using a gradient of acetonitrile in 0.1% TFA (FIG. 52). The peptides indicated by the asterisks were sequenced on an Applied Biosystems 470A gas phase sequencer and the sequences are as follows (and are also set forth in SEQ. ID. NOs. 1, 2, 3, 4 and 5, respectively):

Peptide 13: AQILELPY-GDV-MFLLLP-E . . .
Peptide 11: GRANFSGMSE-NDLF . . .
Peptide 10: MAE-EVEVYIPQFKLEE-Y . . .
Peptide 6: LNIGYIEDLK
Peptide 9: IPNLLPEG-V

EXAMPLE 8

Molecular Cloning of Minactivin a) Isolation of mRNA

From FIG. 34, the optimal time of transcription for PAM induced U937 cells could be estimated to be between 15 and 25 hours. Therefore, a four liter serum-free culture of U937 cells at a cell density of $1.2 \times 10^6$ cells/ml was incubated for 19 hours in the presence of PMA, the cells harvested, and quick frozen in liquid nitrogen until further use. Non-PMA stimulated U937 cells from three day serum-free cultures were also retained for mRNA isolation. Human blood monocytes prepared as described in international patent application WO86/01212, and cultured for 3 days in vitro were also used as a source of mRNA.

Total RNA from each of the above sources was extracted by a modification of the Guanidin-HCL method [Chirgwin, J. M. et al Biochemistry 18 5294 (1979)]. The cell pellet was homogenized in 20 volumes (per gram weight) of buffer containing 4M guanidine isothiocyanate, 50 mM Tris HCl, ph7.5, 10 mM EDTA, 0.5% Sarkosyl, 0.1M 2-mercaptoethanol in a blender at low speed for three minutes at 4° C. The suspension was then centrifuged at 5 000×g for 10 minutes at 4° C. to remove debris. Subsequent centrifugations were carried out at 5–10 000×g unless specified otherwise. Nucleic acids were precipitated from the supernatant by the addition of acetic acid to 25 mM and 0.75 volumes of cold ethanol, and incubated overnight at −20° C. The suspension was centrifuged again for 30 minutes at −10° C., and the pellet dissolved in buffer containing 7.5M guanidine HCl, 20 mM sodium acetate pH5.0, 1 mM dithiothreitol at 20% of the original volume. After centrifuging to remove any undissolved material, the RNA was reprecipitated with 0.55 volumes of cold ethanol at −20° C. for 1–3 hours. The RNA was recovered by centrifugation, redissolved in the guanidine HCl buffer, and reprecipitated. The last step was repeated 3 times. Following the last precipitation, the pellet was dissolved in 20 ml of 20 mM EDTA, pH7.0 and extracted with an equal volume of chloroform: butanol (4:1). RNA was then precipitated from the aqueous phase by the addition of sodium acetate, pH5.0 to 0.3M and two volumes of cold ethanol at −20° C. overnight. The RNA was recovered by centrifugation and treated with 100 mg/ml proteinase K in 20 mM HEPES, pH7.4, 0.5% sodium dodecyl sulfate for 4 hours at 50° C. to remove any residual protein. The RNA was then recovered by precipitation in the presence of 0.2M sodium acetate, pH5.0 and two volumes of ethanol at −20° C. Following recovery by centrifugation, any residual DNA was removed by precipitation of the RNA in the presence of 3M sodium acetate, pH6.0, overnight at 4° C. The RNA was recovered by centrifugation at 15 000×g at 4° C. for 1 hour and precipitated in the presence of 0.25N sodium chloride and two volumes of ethanol. The RNA was again recovered by centrifugation. Poly A+mRNA was then isolated by two cycles of adsorption and elution from oligo (dT)-cellulose [Aviv, H. Leder, P. Proc. Natl. Acad. Sci. USA 69 1408 (1972)].

The poly A+mRNA was enriched 10 to 20 fold for minactivin mRNA by sucrose density gradient centrifugation. The sample was layered on a 15 to 34% (w/w) sucrose gradient and centrifuged in a Beckman SW41 rotor at 33 000 rpm for 16 hours at 4° C. FIG. 35 shows a gel analysis under denaturing conditions of the size fractionated mRNA preparation. Minactivin mRNA was detected in those fractions (Fractions 16 and 17) centered around the 18S ribosomal RNA standard as determined by in vitro translation and immunoprecipitation (method described below) as shown in FIG. 36.

b) Identification of the Minactivin Translation Product

Minactivin mRNA was identified by in vitro translation in a cell free reticulocyte lysate system followed by immunoprecipitation of the minactivin translation product utilizing its natural substrate, urokinase.

Rabbit reticulocyte lysate commercially available from Amersham, was used primarily according to the manufacturer's instructions with the addition of calf liver tRNA (Boehringer Mannheim) at a concentration of 100 ng/ml. $^{35}$S-methionine (Amersham) was added at a concentration of 2 mCI/ml to allow detection of the translation products by autoradiography. Poly A+-mRNA prepared as described above was translated at a concentration of 50 mg/ml for 90 minutes at 30° C. Twenty-five microliters of the translation mixture was used for each immunoprecipitation. Following incubation and removal of a washed suspension of whole Staphylococcus aureus cells (Pansorbin, Calbiochem) to minimize nonspecific binding, the sample was incubated with 50 mPU of urokinase (Calbiochem) for 90 minutes at room temperature. This step allows complex formation between the minactivin translation product and urokinase. The complex was removed from the solution by the addition of 1-2 microliters or anti-urokinase antiserum (Green Cross Corp.), or antibodies against placental inhibitor and incubated at room temperature for 30 minutes and overnight at 4° C., and then precipitated by the addition of 25 microliters of washed Pansorbin. After centrifugation the minactivin-urokinase-antibody-Pansorbin pellet was washed by repeated centrifugation and resuspension in 0.05% Nonidet-P40, 0.15M NaCl, 5 mM EDTA, 50 mM Tris HCl pH 8.0, 0.02% sodium azide, disrupted by boiling in the presence of 2% SDS, and 2-mercaptoethanol, and the products analysed by gel electrophoresis followed by autoradiography.

Immunoprecipitation of the $^{35}$S-labelled translation products with antibodies against urokinase yielded urokinase specific translation products having $M_r$s of 69 000 and 79 000. These protein bands represent specific complexes of minactivin with urokinase as:

1) they are not present in the absence of urokinase or mRNA;
2) they do not precipitate in the absence of antibody, and;
3) they compete with unlabelled purified minactivin and placental inhibitor (Calbiochem) preparations for urokinase binding (FIG. 4).

The immunoprecipitated product was found to represent 0.05% of the total protein synthesized from mRNA obtained from PMA induced U937 cells. No immunoprecipitation products could be detected from mRNA obtained from non-induced U937 cells, presumably due to the decreased levels of minactivin mRNA in this preparation.

Immunoprecipitation of the urokinase-minactivin translation products using antibodies to placental inhibitor yielded identical results. Several anti-placental inhibitor antibody preparations precipitated the distinctive urokinase-minactivin translation product complexes at 69 000 and 79 000 MW (FIG. 38).

A comparison of the immunoprecipitation products obtained in the presence and absence of urokinase allows direct identification of the minactivin translation product as shown in FIG. 39. It is present as a distinct band at a $M_r$ of 43 000. This molecular weight appears to be slightly less than that observed for the native protein possibly due to glycosylation. In the presence of urokinase, this band disappears and the characteristic urokinase-minactivin translation product is detected at 69 000 $M_r$. The additional protein band at 79 to 80 000 $M_r$ observed previously appears to represent a non-reduced form of the complex as the samples were analyzed under partially reduced conditions.

Furthermore, it was found that complex formation with the minactivin translation product was dependent on the presence of the low molecular weight form of urokinase (HPA 33). Pure preparations of HPA 52 and HPA 33 were obtained (Calbiochem) and verified to be predominantly one species or the other by fibrin overlay (FIG. 40). In addition, plasminogen/plasmin was added to HPA 33 to convert any residual traces of HPA 52 in the preparation to the low molecular weight form. The distinctive urokinase-minactivin translation product complex at 69 000 MW appeared only when the urokinase preparations used contained HPA 33. The explanation for this result is unknown. Addition of trasylol to the lysate mixture to inhibit possible proteolysis had no effect on this result.

In summary, in vitro translation of mRNA from U937 cells clearly yields a biologically active minactivin translation product of $M_r$ approximately 43 000 which can be easily identified by the formation of its complex with urokinase giving a characteristic $M_r$ of 69 000.

c) Construction of Complementary DNA Libraries cDNA libraries were constructed from total poly A+ mRNA or sucrose density gradient fractionated mRNA using a variety of established methods [see in general Maniatis, T. et al Molecular Cloning (1982)]. By way of example, the first strand complementary DNA was generally synthesized from the mRNA using primer initiated reverse transcriptase. Second strand was then synthesized, for example, by (1) conventional hairpin-loop primed DNA synthesis using DNA polymerase or reverse transcriptase [Maniatis, T. et al Molecular Cloning (1982)]; (2) RNase H-DNA polymerase I—mediated second strand synthesis [Grubler, U. Hoffman, B. J. Gene. 25 (1983) 263–269, Laperye, B. Amabric, F. Gene 37 (1985) 215–220]; or (3) 5'-tailed priming method of Land, H. et al Nucleic Acid Research 9 2251–2266 (1981). After treatment with S1 nuclease (if required), the DNA is methylated and blunt ends generated using standard methods of filling-in, e.g. DNA polymerase, the Klenow fragment, or T4-polymerase. Subsequently, the cDNAs can be cloned by joining them to suitable plasmid (e.g. pBR322, pUC or pUR systems) or bacteriophage (e.g. lambda gt 11) vectors through complementary homopolymeric tails or cohesive ends created with synthetic linker segments containing appropriate restriction sites using standard procedures, and then transforming a suitable host.

EXAMPLE 9

A preferred method of constructing the cDNA libraries is as follows. Methods for purifying DNA from both *E. coli* and bacteriophages lambda, and subsequent standard manipulations such as digestion with restriction enzymes, ligations and transformations and radiolabelling of DNA with $^{32}$P-ATP, as well as phenol:-chloroform extraction and ethanol precipitation of DNA which are used in Examples 5 to 10 are as described by Maniatis, T. et al Molecular Cloning (1982). cDNA was synthesized from 6 micrograms of total poly A+ mRNA using Moloney murine leukemia virus reverse transcriptase (BRL, 200 U/microgram mRNA) in the presence of 50 mM Tris HCl, 75 mM KCl, 10 mM DTT, 3 mM MgCl, 1 mM each of dATP, cCTP, dGTP, and dTTP, 10 micrograms/ml Oligo (dT)$_{12-18}$ and 100 micrograms/ml BSA. A 200 microliter reaction volume was incubated at 37° C. for 40 minutes. Second strand was synthesized by hairpin loop primed synthesis using the Klenow fragment of DNA polymerase I. The reaction was heated at 70° C. for 10 minutes to separate DNA/RNA duplexes, diluted to twice the volume and Klenow added to 325 U/ml in the presence of 10 microCuries of dATP (1800 Ci/mmole). The reaction was allowed to incubate for 1 hour at 15° C. Following phenol:chloroform (1:1) extraction and ethanol precipitation [as described by Maniatis, T. et al Molecular Cloning (1982)], the DNA was dissolved and the hairpin loop was removed by treatment with 80 units of S1 Nuclease (P/L Biochemicals) in the presence of 0.2M NaCl, 50 mM sodium acetate pH 4.5, 1 mM ZnSO$_4$ and 0.5% glycerol and precipitated as described previously.

The double stranded cDNA was then methylated using 20 Units of EcoR1 Methylase (Biolabs) in the presence of 100 mM Tris-HCl pH 8.0, 10 mM EDTA and 80 micro-molar S-adenosyl methionine. The DNA was repaired by the addition of 2.5 U of T4 DNA Polymerase in the presence of 33 mM Tris acetate ph8.0, 66 mM potassium acetate, 10 mM magnesium acetate, 0.5 mM dithiothreitol, 0.1 mg/ml BSA and 0.5 mM each of dATP, dCTP, dGTP, and dTTP for 1 hour at 37° C., followed by the addition of T4 polynucleotide kinase (20 U) and 0.1 mM ATP. Following phenol:chloroform (1:1) extraction and ethanol precipitation [as described by Maniatis, T. et al Molecular Cloning (1982)], Eco R1 linkers were added to the redissolved DNA (2 micrograms linkers/microgram cDNA) using T4 DNA ligase (IBI; 1.2 U/microgram, DNA). The reaction was carried out on a concentrated cDNA solution (167 micrograms/ml) at 26° C. for 4 hours. After treatment with EcoR1, the free linkers were separated from the cDNA by gel filtration chromatography on Biogel A 50M, as described by Huynh, T. V. et al DNA Cloning Vol 1 p49–78 (1985). Fractions containing cDNA were analysed by agarose gel electrophoresis followed by autoradiography and those fractions containing cDNA of average length greater than 1 000 b.p.f were pooled and the cDNA concentrated by lyophilization to near dryness and precipitated by the addition of two volumes of ethanol. The yield of cDNA was 2.5 micrograms.

cDNA libraries were prepared in both lambda gt 11 and gt 10. cDNA (100 ng) was ligated to EcoR1-cleaved, phosphatased lambda gt 11 (1 microgram), at a DNA concentration of 220 micrograms/ml at 4° C. for 16 hours. The DNA was packaged using prepared packaging preparations from Vector Cloning Systems. Phages were amplified by adsorption to *E. coli* strain Y1088 and screened in Y1090. The lambda gt 11 library contained approximately $8 \times 10^6$ recombinants per microgram cDNA (94% of total phages). The proportion of recombinants that contained cDNA molecules was determined by screening the library with cDNA synthesized in the presence of alpha[$^{32}$P]-dATP. Around 90% of white plaques hybridized with this probe.

For the library prepared in lambda gt 10, cDNA (200 ng) was ligated to EcoR1 cleaved, phosphatased lambda gt 10 (1 microgram), at a DNA concentration of 240 micrograms/ml at 25° C. for 4 hours. The DNA was packaged as above using *E. coli* strain C600 hfl.

The lambda gt 10 library contained approximately $7.5 \times 10^6$ recombinants per microgram cDNA. The proportion of recombinants that contained cDNA molecules was determined by screening the library with radiolabelled cDNA. Greater than 90% of plaques hybridized with this probe.

EXAMPLE 10

Identification of Clones containing the Minactivin Gene

The clone(s) containing the gene encoding minactivin may be identified with the probes described in the following examples using established techniques [see generally Maniatis, T. et al Molecular Cloning (1982)].

EXAMPLE 10a cDNA clones containing sequences complementary to minactivin mRNA may be identified by hybridization selection [Maniatis, T. et al Molecular Cloning (1982)]. The cloned DNA is denatured, immobilized to a solid matrix such as nitrocellulose, and hybridized to preparations of total mRNA. The RNA/DNA duplex is heated to release the mRNA which is then translated in the in vitro rabbit reticulocyte lysate cell free system as described above. The translation product may then be identified as described in Example 4b.

EXAMPLE 10b

DNA Probes Complementary to the Minactivin Gene Sequence

Using the amino acid sequence obtained for peptides of minactivin as described in Example 3, oligonucleotide sequences which would code for the amino acid sequence can then be predicted and oligonucleotide probes synthesised using conventional established technology [Beaucage, S. L. and Carruthers, N. H. Tetrahedron Letts 1859–1862 (1981)]. Using this sequence data, a number of oligonucleotide probes were synthesized using an Applied Biosystems 380A DNA synthesizer. The sequences of these oligonucleotides are set forth in SEQ. ID. NOs. 6, 7, 8, 9, 10, 11, 12, 13, 14 and 15, respectively, and as follows:

```
                  (C)
      (A)   (T)   (G)        (A)
1.    TT(G) AA(C) TG(A)  ACI  AT(G) TA
                  (T)

(A)         (A)
      (G)   (T)   (G)   (C)
2.    TA(T) AC(C) TC(T) AC(T) TC
      (C)         (C)

(A)         (A)
      (G)   (A)   (T)   (G)
3.    TC(T) A(G)I AT(C) TG(C) GC
      (C)         (T)

(T)                        (T)       (T)
4.  TTG  AA(C)  TGI  ACI  ATG  TAI  AC(C)  TCI  AC(C)  TC (T)
      (T)         (A)   (C)         (A)
5.    TC(C) TCI   AT(G) TA(A) CCI   AT(G) TT
                              (G)

(T)         (T)
            (C)         (G)(C)
6.    AAI   TT(A) GCI   C(T)(A) CC
            (G)         (G)

7.    ATA TGT TTC CTC GAG CTT GAA CTG AGG GAT GTA CAC CTC GAC TTC GCT CTC
      TGC CAT

8.    TTC ATC AGG CAA CAG GAG GAA CAT GCT CAC ATC TCC GGC GTA AGG GAG TTC
      CAG GAT CTT CAT TTT

9.    CTC CTC CAG CTT GAA CTG GGG GAT GTA GAC CTC CAC CTC (A)   (G)        (C)
10.   CTT GAA CTG  (G)GG (A)AT GTA (G)AC CTC CAC CTC
```

The specific oligonucleotide probe may be radiolabelled and then used to screen cDNA libraries by in situ hybridization of bacterial colonies or bacteriophage plaques using standard techniques [Maniatis, T. et al Molecular Cloning (1982)] to identify clones containing all or part of the minactivin gene.

EXAMPLE 10c

Immunological Screening

The clones may be screened using established procedures (Young, R. A. and Davis, R. W. Science 222 778–782) with antibodies which cross-react with the native minactivin protein.

Antibodies to minactivin are prepared by standard methods, for example, each rabbit is immunized with 10 to 100 micrograms of purified minactivin in the presence of a suitable adjuvant, such as Freunds complete or montanide. Following a boost of an equivalent amount approximately four weeks later, the rabbit is bled and rabbit serum obtained which is assayed for antibodies to minactivin. Antiserum prepared in this way was used to immunoprecipitate the minactivin translation product as shown in FIG. 38 using Ab2 (bled 1 week after boost) and Ab3 (bled 2 weeks after boost) antisera. These antisera could be used to screen expression libraries prepared in lambda gt 11 according to published methods [Huynh, T. V. et al DNA Cloning Vol 1 49–78 (1985)].

EXAMPLE 10d

Screening for Biological Activity

Clones containing the minactivin gene may be tested or screened for minactivin activity using either radiolabelled urokinase or urokinase and antibodies to urokinase. This would be accomplished using standard techniques of immunological screening, as described in Example 6c. Urokinase and antibodies to urokinase may be obtained commercially. Radiolabelled urokinase may be prepared as described below.

Commercially obtained urokinase (Calbiochem) was affinity purified by chromatography on p-aminobenzamidine sepharose according to published protocols [Holmberg, L., Bladh, B., Astedt, B. Biochim. Biophys. Acta 445, 215–222 (1976), and Goldfarb, R. H., Quigley, J. P. Biochemistry 19, 5463–5471 (1980)]. Seventy-five Ploug units of the purified urokinase was iodinated by conjugation with N-succinimidyl 3-(4-hydroxy, 5-[$I^{125}$] iodophenyl) proprionate according to the Bolton Hunter procedure. The $I^{125}$-labelled urokinase was separated from the free label by chromatography on Sephadex G-25M equilibrated in 0.1M sodium phosphate, pH 7.0, 0.4M sodium chloride, 0.1% Triton X100 and 1% carrier bovine serum albumin.

Analysis of the $I^{125}$-labelled urokinase preparation by SDS-polyacrylamide gel electrophoresis under non-reducing conditions showed the presence of the characteristic high ($M_r$ 55 000) and low ($M_r$ 33 000) molecular weight forms of urokinase (FIG. 46). Under reducing conditions, the high molecular weight form is dissociated into its characteristic 33 000 and 22 000 $M_r$ subunits. Iodination of the urokinase preparation resulted in a loss of 10 to 15% plasminogen activator activity as measured by the assay of Coleman and Green [Ann. N.Y. Acad. Sci. 370, 617 (1981)], but had no effect on minactivin inhibition of the enzyme. Dot blot assays in which various dilutions of minactivin were spotted on nitrocellulose paper, incubated overnight with radiolabelled urokinase, washed, dried, and autoradiographed, showed that the radiolabelled urokinase could detect minactivin bound to a solid phase at a sensitivity of 10 mU or approximately 0.1 ng minactivin.

EXAMPLE 11

Identification of the Minactivin Gene

The preferred method of identifying the minactivin gene is as follows. Following synthesis, the oligonucleotide probes 7–10 described in Example 6b and set forth in SEQ. ID. NOs. 7, 8, 9 and 10 were purified by polyacrylamide gel electrophoresis, and labelled with polynucleotide kinase (IBI, 1 U/pmole DNA) and gamma-$^{32}$P-ATP and purified by ion exchange chromatography using standard procedures [see generally Maniatis, T. et al Molecular Cloning (1982)].

The lambda gt10 library as described in Example 5 was screened by in situ hybridization according to standard experimental procedures [see generally Maniatis, T. et al Molecular Cloning (1982)]. Hybridization conditions were adjusted to allow specific binding with minimum background and were determined to be as follows:

Probes 7 and 8 (SEQ ID NOs. 7 and 8): 3 hours at 50° C. in 6×SSC, 5×Denhardt's, 0.1% SDS, 20 μg/ml tRNA, following prehybridization for 1 hour at 42° C. in 6×SSC, 5×Denhardt's 0.5% SDS, 0.2 mg/ml sheared calf thymus DNA.

Probes 9 and 10 (SEQ ID NOs. 9 and 10): 16 hours at 37° C. in 10× Denhardt's, 5×SSC, 0.05% sodium pyrophosphate.

$^{32}$P-labelled oligonucleotide probes of specific activity greater than $10^8$ cpm/μg were used at approximately 0.5 pmole/ml. The filters were washed in 0.5× or 2×SSC containing 0.1% SDS at increasing temperatures to raise the stringency for selection of positive clones.

Plaques giving positive signals were picked, rescreened, and the phage DNA purified using standard procedures (see for example Maniatis et al. Molecular Cloning 1982).

Two recombinant bacteriophage clones MIN1D and MIN611, containing sequences which cross-hybridized to each other were obtained, with EcoRI-linkered cDNA inserts of 2100 and 1060 base pairs respectively. These inserts were subcloned into plasmid pUC18 to create plasmids pBTA440 and pBTA441 respectively and mapped by restriction enzyme analysis as shown in FIG. 53. Southern blot analysis of clone MIN1D located the binding region of oligonucleotide probes 7 and 8 (SEQ ID NOs. 7 and 8) within a 320 base pair XbaI-NcoI restriction fragment as illustrated in FIG. 53.

That these clones contained genes which code for minactivin was verified by hybrid-select translation and DNA sequence analysis.

Hybrid Select Translation

Purified pBTA440 was immobilized on nitrocellulose filters at a concentration of 20 μg per 3 mm×3 mm filter according to the procedure described by Maniatis et al. (Molecular Cloning 1982). After washing, each filter was incubated with 50 μg of total mRNA and hybridized for 3 hours at 50° C. After thorough washing, the specifically hybridized mRNA was eluted at 65° C. and then translated in vitro using a commercial rabbit reticulocyte lysate preparation (Amersham).

As illustrated in FIG. 54, the hybridized mRNA was shown to specifically code for a translation product of $M_r$ 43 000 by gel electrophoresis, characteristic of the minactivin translation product described in Example 4b. Furthermore in the presence of urokinase, this band disappeared and the characteristic urokinase-minactivin complex was detected at 69 000 $M_r$.

DNA Sequence Analysis

Restriction fragments of pBTA440 were subcloned into the single stranded phage vectors M13mp9, M13mp18 and M13mp19 and the DNA sequence of the 2 100 bp inserted was determined using the Sanger chain termination method. Examination of the DNA sequence indicated that the 2100 bp insert did not contain the entire coding sequence of the minactivin gene.

Primer Extension

To obtain the remainder of the DNA sequence encoding the N-terminal region of minactivin a second cDNA library was constructed using primer extension [Luse, D. S. et al, Nucleic Acid Research 9 (17) 4339–4355 (1981)]. The library was prepared by priming 5 micrograms of poly A+mRNA with the oligonucleotide (SEQ ID NO. 16) 5' TTC CAG TAA ATA ATT CCC TGT GGA TGC ATT 3' being complementary to the previously sequenced nucleotides 391 to 420. EcoRI-linkered cDNA inserts were subsequently cloned in lambda gt10 using standard techniques.

Approximately $5.3 \times 10^3$ of the $7.2 \times 10^4$ clones obtained were screened with a second oligonucleotide (SEQ. ID. NO. 17) 5' GCC TGC AAA ATC GCA TCA GGA TAA CTA CC 3' (complementary to nucleotides 310–335). Of the 100 positive clones obtained, 15 were purified and the clone (clone 13) with the largest cDNA insert (430 bp) was subcloned into plasmid pUC18 to create plasmid pBTA442. The DNA sequence of pBTA442 was determined as described above (see also FIG. 53).

The coding sequence of the minactivin gene, contained in pBTA440 and pBTA443, a plasmid containing the 430 bp 5' minactivin sequence in pUC18 in opposite orientation to pBTA442, was made contiguous by recombining certain DNA restriction fragments to create pBTA438 as shown in FIG. 55. *E. coli* K-12, strain JM109 containing pBTA438 has been deposited with the American Type culture collection, 12301 Parklawn Drive, Rockville, Md. 20852, United States of America on 11 Feb. 1987 under accession number ATCC 53585.

The complete cDNA sequence (SEQ. ID NO:18) of the minactivin gene and the deduced amino acid sequence (SEQ ID NO:19) of the minactivin protein are given in FIG. 56. The complete translation product consists of 415 amino acids ($M_r$ 46 543). The gene encodes the 5 peptides (set forth in SEQ. ID. NOs. 1, 2, 3, 4 and 5, respectively) obtained from the amino acid sequence analysis of native minactivin as illustrated in FIG. 56.

The DNA sequence analysis reveals that minactivin is a member of the serine protease inhibitor superfamily, (known as serpins) albeit specific for urokinase type plasminogen activators.

EXAMPLE 12

Expression of Biologically Active Minactivin

High-level expression of the biologically active molecule is obtained, for example, by integration of the full-length cDNA present in pBTA438 into various vectors which can direct the synthesis of the protein in a variety of hosts such as bacteria or eukarotic cells (such as mammalian cells transfected or transformed with the vector). The vector preferably contains a nucleotide sequence capable of controlling expression of the nucleotide sequence coding for minactivin. This second nucleotide sequence may include, by way of example, a promoter sequence, polyadenylation sequences, or nucleotide sequences which allow the protein to be expressed as a hybrid molecule fused with another protein.

EXAMPLE 13

Bacterial Expression of Minactivin

The general approach is the preparation of an expression vector or cloning vehicle replicable in *E. coli*, which contains a DNA sequence which codes for the expression of minactivin.

Minactivin may be expressed in its native form or as a hybrid molecule fused to another protein. These constructions are shown in FIGS. 57 and 59.

One series of plasmid constructs used the lambda $P_L$ expression vectors pLK57, and pLK58 (Botterman et al. Gene 37; 229–239, 1985) to express native or near-native (N-terminal amino acid modified) minactivin.

As shown in FIG. 57, the plasmid pBTA438 was digested with EcoRI and DraI and a 1610 bp EcoRI-DraI restriction fragment was isolated from an agarose gel. This fragment was ligated with T4 ligase to vector pLK57 which had been digested with EcoRI and EcoRV. The derivative plasmid pBTA444 contains the lambda $P_L$ promoter controlling the expression of native minactivin.

The expression vector pBTA444 was used to transform *E. Coli* K-12 strain N4830 (Joyce et al. PNAS 80, 1830–1834, 1983) which contains the thermolabile CI repressor of lambda. Cells transformed with pBTA444 were grown overnight in MEB medium (Mott et al PNAS 82, 88–92, 1985) 100 micrograms/ml ampicillin at 28° C. Cells were diluted in MEB medium, grown at 28° C. to an $OD_{600}$ of 1.0 when prewarmed (65° C.) MEB medium was added in equal volume to equilibrate the temperature to 42° C.

Following 4 hours of growth at 42° C. the cells were harvested and membrane and soluble protein fractions prepared by resuspending washed cells (after −70° C. freezing and thawing) in 200μ of 20% sucrose 30 mM Tris-HCl pH8.1, and mg/ml lysozyme solution followed by the addition of 3 mls of 3M EDTA pH7.3. The cell extract was clarified by brief sonification and membrane and insoluble proteins pelleted by centrifugation (27,000×g), 60 mins). The soluble proteins were precipitated by the addition of trichloroacetic acid (10% w/v) to the supernatant and the pellet dissolved in water. The pelleted membranes wee also dissolved in water. Samples of these fractions for both uninduced (28° C.) and induced (42° C.) cells were analysed by SDS-polyacrylamide gel electrophoresis and immunological detection of minactivin by western transfer using antiserum against human placental inhibitor. As shown in FIG. 58 a minactivin protein band (Mr 40–50K), visualized by western transfer using antibodies to human placental inhibitor and rabbit anti-goat IgG coupled to alkaline phosphatase (Sigma) is present in both the induced (42° C.) soluble and membrane fractions.

An alternative method for producing native minactivin is also shown in FIG. 57. The plasmid pBTA442 was digested with XhoII and a 243 bp XhoII restriction fragment was purified from an agarose gel. This fragment was ligated with T4 ligase to vector pLK58 digested with BglII. The derivative plasmid pBTA445 was digested with PvuII and SmaI and a 2800 bp fragment purified and ligated with T4 ligase to a purified 1320 bp PvuII-DraI restriction fragment from pBTA438. The derivative plasmid pBTA446 was linearized with BglII and ligated to a synthetic double stranded 26 mer oligonucleotide containing a bacterial ribosome binding site and the initial nucleotides of the native minactivin gene, creating plasmid pBTA447. When pBTA447 is transformed into an appropriate host, such as N4830, induced and analysed as described above, minactivin is again produced as shown in FIG. 58. In both cases, for pBTA444 and pBTA447 containing cells, minactivin was present in both the induced (42° C.) soluble and membrane fractions.

To assess the biological activity of minactivin produced in *E. coli* N4830, soluble and membrane fractions were incubated for 90 mins with high and low molecular weight urokinase as described in Example 4. Samples were then precipitated with acetone, resuspended in water, and run on a reducing SDS-polyacrylamide gel. Minactivin and minactivin-urokinase complexes were visualized by Western transfer as described above. As shown in FIG. 58 minactivin in the soluble fraction from induced *E. coli* N4830 containing pBTA447 complexes with urokinase under standard assay conditions. This indicates that minactivin produced from these bacterial cells retains biological activity.

Two examples of a method for producing a protein that is the fusion of all or part of one protein coding sequence and all or part of the minactivin coding sequence follows. As shown in FIG. 59, the plasmid pBTA440 was digested with SspI and DraI and a 1110 bp fragment was isolated from an agarose gel. This fragment was ligated to the vector pBTA449 digested with EcoRV creating pBTA450. pBTA450 was then digested with AvaI and a purified 2800 bp fragment ligated to the plasmid pLK57 digested with AvaI to create plasmid pBTA586. This places part of the minactivin coding sequence under the control of the lambda $P_L$ promoter and fused to the coding sequence of the first 80 amino acids of traT gene, the first 20 of which constitutes a signal sequence that results in the fusion appearing in the outer membrane of *E. coli*. This signal sequence is cleaved off during transport to the outer membrane, which is the normal location of the traT protein.

When plasmid pBTA586 is transformed into an appropriate host, such as N4830, and induced with temperature shift as above, the TraT-Minactivin fusion protein appears in the outer membrane, as shown in FIG. 60.

A second example of a method for producing a fusion is shown in FIG. 59. In plasmid pBTA440, the minactivin coding sequence is fused in frame with a portion of the β-galactosidase gene present on plasmid pUC18.

When plasmid pBTA440 is transformed into an appropriate host, such as JM101, or any *E. coli* strain which contains the lacI$^q$ gene, and induced by addition of isopropyl-thio-β-D-galactopyranoside (final concentration 1 mM), minactivin production can be detected as described above (FIG. 60).

EXAMPLE 14

Expression of Recombinant Minactivin in Eukaryotic Cells

A fragment of pBTA438 containing the entire coding region of minactivin was inserted into a series of vectors capable of stable integration and expression of eukaryotic genes in mammalian cells. These included 1) pKC3 (derived from pKO-neo, Van Doren, Hanahan, D., Gluzman, Y., J. Virol. 50 606–614 (1984)) wherein the minactivin cDNA sequence is placed under the control of the SV40 early promoter; 2) pZipNeoSV(X)1 (Cepko, C. L., Roberts, B. E., Mulligan, R. C., Cell 37 1053–1062 (1984)), a Molony Murine Leukemia virus-derived retroviral shuttle system in which the minactivin gene is placed downstream from the retroviral LTR promoter and selection is based on the neo gene which confers kanamycin resistance in prokaryotes and G418 resistance in eukaryotes; and 3) pMSG (commercially available from Pharmacia), wherein regulated expression of minactivin is achieved by utilizing a dexamethasone inducible promoter contained within the Mouse Mammary Tumor-Virus (MMTV) 5'-LTR.

The construction of these three vectors is shown in FIG. 61 and the details are as follows. The coding region of the minactivin gene was isolated from pBTA438 as a 1610 bp EcoRI-DraI fragment and inserted into the following vectors as described below.

The 1610 bp EcoRI-DraI fragment was ligated into pKC3 which had been digested with EcoRI and SmaI, and then transformed into E. coli C600γ. The resultant plasmid was designated pBTA587.

In the second construction, the 1610 bp EcoRI-DraI fragment was rendered flush-ended using the Klenow fragment of DNA polymerase I, ligated into the SmaI site of pMSG, and transformed into a suitable E. coli K-12 host. Colonies containing the minactivin gene in pMSG were detected by colony hybridization using the $^{32}P$-labelled oligonucleotide (29 mer) previously described in Example 7 (complementary to nucleotides 310–335). The resultant plasmid was designated pBTA588.

In the third construction, the flush-ended EcoRI/DraI fragment described above was ligated into pUC7 which had been digested with HincII giving the construction designated pBTA589. As the HincII site in pUC7 is flanked by BamHI sites, this allowed the minactivin gene to be isolated following BamHI digestion and ligated into the BamHI site of pZIPNeo SV(X) 1. Following transformation into a suitable E. coli K-12 host, colonies containing the minactivin gene were detected by colony hybridization as described above. The resultant plasmid was designated pBTA590.

Transfection of Eukaryotic Cells

All plasmids were transfected into eukaryotic cells by the calcium phosphate method. Approximately $1-2 \times 10^5$ cells were seeded into a T25 flask in 5 ml of Dulbecco modified Eagle medium supplemented with 10% (v/v) foetal calf serum, 3.6 mM glutamine 200 mM, 45 IU/ml penicillin and 45 mg/ml streptomycin (complete medium). Approximately 1 to 5 μg of CsCl gradient purified DNA was precipitated with calcium phosphate and added to the cells. After 4 hours, the cells were treated to a glycerol shock, and cultured in complete medium for 3 days. The culture supernatant was then removed for measurement of transient expression. The cells were then trypsinized and split ⅓ into T75 flasks with complete medium containing the appropriate antibiotic selection (see below). The cells were washed every 6 to 7 days with the same medium and transfectants picked at 14 to 28 days and cultured individually until confluent growth was achieved.

The conditions of transfection for each of pBTA587, pBTA588 and pBTA590 were as follows:

pBTA587. As pKC3 does not contain a selectable marker, pBTA587 was cotransfected with pZIPNeo SV(X)1 at a molar ratio of 7.5:1, pBTA587: pZIPNeo SV(X)I. Transfectants were selected with complete medium containing 0.4 mg/ml G418. Transfections were carried out in COS cells.

pBTA588. As pMSG contains the E. coli xanthine-guanine phosphoribosyltransferase (gpt) gene expressed from the SV40 early promotors, stably transfected cells were selected in HAT medium containing hypoxanthine, aminopterin and mycophenolic acid. Transfections were carried out using NIH3T3 cells.

pBTA590. Transfectants were selected using complete medium containing 0.4 mg/ml G418. Transfections were carried out in NIH3T3 cells.

Analysis of Expression of Recombinant Minactivin in Eukaryotic Cells

Following transfection, transient expression of recombinant minactivin is detected by culturing the cells in the presence of $^{35}S$-methionine and specific immunoprecipitation of the recombinant radiolabelled minactivin using antibodies to placental inhibitor essentially according to the method described in Example 4b. For example, forth-eight hours after transfection of pBTA587 into COS cells, the supernatant was removed and the cells cultured in the presence of 1 ml methionine-free EMEM (Flow), supplemented with $^{35}S$-methionine (Amersham). Following immunoprecipitation with 50 mg goat anti-placental inhibitor antibodies and 200 ml washed Pansorbin, the complexes were analysed by SDS-polyacrylamide gel electrophoresis (reducing conditions) and visualized by autoradiography as shown in FIG. 62. Recombinant minactivin is detected as a band of Mr 45–48,000, which is not observed in the corresponding control transfection containing the vector (pKC3) alone. When urokinase (15 Plough units, Calbiochem) is added to the supernatant prior to immunoprecipitation, this band disappears which is characteristic of biologically active minactivin. A band is observed at $M_r$ 69,000 which is indicative of the minactivin urokinase complex, but is somewhat obscured by a nonspecific protein band at the same position. Some of the recombinant minactivin also appears to have been proteolytically nicked following the addition of the urokinase preparation, as evidenced by the $M_r$ 35–37,000 band detected.

That the recombinant minactivin produced as biologically active was determined by culturing the cells in the absence of serum for 4 hours and quantitating the inhibition of urokinase activity by the colorimetric assay essentially as described in Example 1. A level of inhibition was detected which correspond to approximately 1 unit/ml minactivin activity above background.

Transfectants containing the minactivin gene can also be analyzed for minactivin activity using radiolabelled urokinase prepared as described in Example 6 or according to the method of Baker. Culture supernatants are incubated with the radiolabelled urokinase in order to allow complex formation between the recombinant minactivin and urokinase. The complex is then removed from the solution by the addition of rabbit antibodies prepared against urokinase (Green Cross Corp.) and precipitated by the addition of washed Pansorbin or anti-rabbit antibodies covalently attached to immunobeads (Biorad). After centrifugation, the minactivin-urokinase-antibody pellet is washed, disrupted by boiling with 2% SDS and the products analysed by gel electrophoresis followed by autoradiography. The presence of biologically active recombinant minactivin produced by the transfected cells is evidenced by the shift in molecular weight of urokinase from Mr 55 000 (or 33 000) to a higher Mr (69 to 92 000) (see Example 4b) characteristic of the formation of the minactivin-urokinase complex.

EXAMPLE 15

Purification and Recovery of Biologically Active Protein

Following the establishment of conditions for the expression of minactivin in *E. coli* at high levels the cells harbouring the plasmid enclosing the minactivin gene are harvested at late log phase. One volume of packed cells are suspended in two volumes of lysis buffer (0.1M sodium phosphate, pH7.0 containing 1 mM EDTA and 1 mM phenyl methyl sulphonyl fluoride) and lysed by three passages through a French Press at 15,000 psi. The suspension is centrifuged at $23,000 \times g$ for 20 minutes and the pellet resuspended in two volumes of lysis buffer containing 5% Triton X-100. The suspension is again centrifuged at $23,000 \times g$ for 20 minutes and the pellet suspended in three volumes of 0.1M Tris-Cl, pH8.0 containing 8M urea and 0.1M DTT. The solution is flushed with nitrogen and incubated in a sealed tube at 37° C. for 2 hours. Following incubation the pH of the solution is lowered to approximately pH3.5 by the addition of 50 ml of glacial acetic acid for every ml of solution. The suspension is clarified by centrifuging as above and the supernatant applied to a Sephadex G-75 column (3.2 cm×90 cm) equilibrated in 0.1M acetic acid. The fractions containing the minactivin are located by SDS-PAGE. The fractions containing the minactivin are pooled and dialysed against 10 mM Tris-Cl, pH8.0 containing 8M Urea and 0.1 mM DTT at room temperature for 16 hours. The analysed solution is then applied to a DEAE-Sephadex column (2.2 cm×25 cm) equilibrated in the above buffer and the column washed to elute unbound material. The minactivin is then eluted from the column using a linear gradient of sodium chloride from 0 to 0.5M in the same buffer. The fractions containing the minactivin are identified by SDS-PAGE and dialysed extensively against distilled water. The protein, which precipitates during this procedure, is recovered by lyophilization. The lyophilized protein is redissolved in 0.1% trifluoroacetic acid and applied to a Vydac C-4 reverse phase column attached to a Waters high pressure liquid chromatograph. The pure minactivin is eluted from the column using a linear gradient of acetonitrile from 0 to 80% in 0.1% trifluoroacetic acid. The $A_{220}$ peak corresponding to minactivin is identified by SDS-PAGE, the fractions pooled and lyophilized.

The lyophilized, purified minactivin is dissolved in 0.1M Tric-Cl, pH8.0 containing 8M urea at a concentration of 10 mg/ml and diluted to 10 mgm/ml into 0.1M Tris Cl, pH8.0 containing 1 mM reduced glutathione and 0.1 mM oxidized glutathione. The refolding reaction is allowed to proceed at room-temperature for 24 hrs and then the solution concentrated and diafiltered against 0.1M sodium phosphate pH7.0 on an Amicon stirred cell using a YM10 membrane. The resultant solution containing active minactivin is assayed using the assay described above (Example 1).

The recovery of biologically active minactivin secreted at high levels from mammalian cells employs the same procedures as described in Example 2 for the purification of the native minactivin from U937 cells. This involves initially a ten fold concentration of the cell free supernatant using an Amicon DC-2 hollow fibre concentrator equipped with a 30,000 dalton cut-off cartridge. The concentrate is then dialysed against at least an equal volume of 50 mM glycine, pH7.8, to remove all traces of dye. The dialysed concentrate is centrifuged in a JA10 rotor at 8000 rpm for 30 min at 4° C. to pellet residual cell debris and protein that may have precipitated during dialysis. The clarified supernatant is then aliquoted and frozen at −20° C. until required for subsequent purification.

Minactivin is further purified from ten-time concentrated culture supernatant by step pH elution using Phenyl-Sepharose as follows.

The ionic strength of the supernatant is adjusted to 2M by the addition of solid NaCl and the pH adjusted to 5.5 with citric acid. This solution is applied to a Phenyl-Sepharose column (4.4 cm×5.0 cm) equilibrated in 50 mM Na citrate, pH5.5, 2M Nacl and 1 mM EDTA and eluted with the same buffer until the baseline absorbance at 280 nm (A280) returned to baseline. The minactivin is then eluted from the column with 50 mM glycine, pH9.0. Fractions containing the highest specific activity minactivin are pooled and concentrated on an Amicon YM10 membrane.

The pooled, concentrated minactivin is then applied to a 2.2 cm×78 cm column of Sephacryl S-200 equilibrated with 0.1M sodium borate, pH9.0. Fractions of 5.0 ml are collected at a flow rate of 0.46 ml/min. The fractions containing minactivin activity were pooled and concentrated to 3 ml using a YM10 membrane. Calibration of this column with known $M_r$ standards indicates that minactivin has a $M_r$ of 45–48 kD.

The concentrated minactivin solution is applied to a preparative flat bed gel of Ultrodex containing Ampholines in the pH range 4.5–6.0 and electrofocussed for 23 hrs at 10° C. on an LKB Multiphor isoelectric-focussing apparatus. Following completion of the run, 30 zones across the length of the gel are scraped out and the protein eluted from each with 10 ml of 1M glycine containing 1 mM EDYA, pH9.0. Aliquots of each frction are assayed for minactivin activity and electrophoresed on 15% SDS-polyacrylamide gels to locate protein. Under these conditions minactivin focusses between pH5 and pH5.2 and is highly purified. This material is again concentrated on an Amicon YM10 membrane and stored at −20° C. in 50 mM glycine, pH9.0, containing 1 mM EDTA and 50% glycerol.

INDUSTRIAL APPLICATION

As a specific inactivator of urokinase-type plasminogen activators, minactivin has a range of potential industrial applications as a clinical reagent for the diagnosis and possible treatment of various human carcinomas and inflammatory conditions.

Similarly, oligonucleotide probes derived from the amino acid sequence of peptides derived from purified minactivin or antibodies to minactivin can be used as diagnostic tools in assays for monitoring the status of diseases such as inflammation and cancer metastasis particularly during prescribed courses of treatment.

Studies of cell transformation in vitro by tumor viruses (Ossowski, let al. J. Exp. Med. 137, 112, 1973) and by chemical carcinogens (Sisskin, et al. Int. J. Cancer, 26, 331, 1980) both show that plasminogen activator secretion is the most consistent early biochemical event associated with transformation. Furthermore, the ability of cell lines to metastasize in vivo has been found to correlate with their ability to express plasminogen activator (Wang et al. Cancer Research 40,288, 1980). It is also well established that tumor cells of several of the most prevalent human cancers, i.e. carcinoma of the lung, breast, prostate and colon, produce high levels of urokinase-type plasminogen activator (Duffy, M. J., O'Grady, P.Eur.J. Clin. Oncol. 20(5)577–582, 1984).

Our previous studies (Stephens, R. S. et al. Blood 66, 333–337, 1985) on malignancy in colon mucosa and conditions which predispose to malignancy, i.e. adenomatous polyps, polyposis coli and inflammatory conditions of the colon such as Crohn's disease and ulcerative colitis, have demonstrated that human colon cancers produce significantly greater amount of urokinase-type plasminogen activator than that occurring in adjacent noninvolved tissue. Minactivin was found to be capable of binding to and inhibiting this tumor associated plasminogen activator (Stephens et al. Blood 66, 333–337, 1985). Thus, it follows that minactivin has industrial application as a reagent for identifying and defining tumors both in vivo and in histological specimens. For imaging tumors in vivo, minactivin may be labelled with an appropriate isotope, such as Technetium-99m (Richardson, V. J. Brit.J. Cancer 40, 35, 1979) or Iodine-131 (Begent, R. H. J. Lancet, Oct. 2, 1982). Following administration of the minactivin preparation, the location and boundaries of the tumor may be determined by known radioisotopic methods, such as gamma-camera imaging. Thus, minactivin offers a sensitive method for enabling the identification of small metastatic cancers particularly those arising after surgical intervention. In the analysis of histochemical specimens, minactivin or its antibody, may be labelled with an isotope such a $I^{131}$, or conjugated to an appropriate enzyme or other chemical reagent. On contact with a histological specimen, such as a biopsy section, minactivin will bind to the tumor type plasminogen activator at its place of secretion, thereby identifying the tumor boundaries and potentially the metastatic state of the tumor. In addition to its diagnostic applications, minactivin is also indicated for use in the direct treatment of tumors. As a specific inhibitor of the enzyme implicated in the process by which tumors invade surrounding tissues (Dano, K. et al., Adv. in Cancer Res. 44, 139, 1985), regulation and, in particular, inhibition of tumor growth and metastases can be achieved. Furthermore, minactivin can be used as a drug delivery system to deliver lectins or toxins directly to growing tumors. It will be appreciated that this system could offer many advantages in terms of specificily and extremely potent tumoricidal capability.

Other biological processes in which urokinase-type plasminogen activators have been implicated involve those physiological events associated with invasion and tissue destruction, such as chronic inflammatory conditions including rheumatoid arthritis. As minactivin is part of the natural host response to tissue degradation, it will prove a useful marker for monitoring the status of the disease particularly during prescribed courses of treatment. Labelled antibodies or DNA probes derived from minactivin have industrial application as diagnostic reagents for monitoring minactivin levels in blood plasma, in macrophages of tissue biopsies and in synovial fluid for correlations with diseased states. Similarly, minactivin itself is also indicated to have a therapeutic effect when administered in vivo in amellorating such conditions.

REFERENCES

1. Hume, D., Gordon, S. (1983). J. Cell Physiol. 117: 189
2. Golder, J. P., Doe, W. F. 91983). Gastroenterology 84: 795.
3. Doe, W. F., Henson, P. M. (1978). J. Exp. Med. 148: 544.
4. Sundstrom, C., Nilsson, K. (1976). Int. J. Cancer 17: 565.
5. Gallagher, R. S., Collins, S., Trujillo, J. (1979). Blood 54: 713.
6. Bradley, T. R., Pilkington, G. R., Garson, M., Hogdson, G. S., Kraft, N. (1982). Br. J. Haematol. 51: 595.
7. Rabin, H., Hopkins R. F., Ruscetti, F. W., Neubauer, R. H., Brown, R. L. kawakami, T. G. (1981). J. Immunol. 127: 1852.
8. Lozzio, C. B., Lozzio, B. B. (1975). Blood 45: 321, 1975.
9. Koerten, H. K., Ploem, J. S., Daems, W. R. (1980). Exp. Cell Res. 128: 470.
10. Yam, L. T., Li, C. Y., Crosby, W. H. (1971). Am. J. Clin. Path. 55: 282.
11. Ornstein, L., Ansley, H., Saunders, A. (1976). Blood Cells 2: 557.
12. Coleman, P. L., Green, G. D. J. (1981). Ann. NY Acad Sci 370: 617.
13. Unkeless, J., Dano, K., Kellermann, G., Reich, E. (1974). J. Biol. Chem. 249: 4295.
14. Granelli-Piperno, A. & Reich, E. (1978). J. Exp. Med. 148: 223–234.
15. Crutchely, D. J., Conanan, L. B. & Maynard, J. R. (19821). Ann. N.Y. Acad. Sci. 370: 609–616.
16. Hoylaerts, M., Rijken, D. C., Lijnen, H. R. & Collen, D. (1982) J. Biol. Chem. 257: 2912-2919.
17. Barlow, G. H., Francis, C. W. & Narder, V. J. (1981). Thromb. Res. 23: 541–547.
18. Loskutoff, D. J. & Edgington, T. S. (1981). J. Biol. Chem. 246: 4142–4145
19. Aggeler, J., Risch, J. & Werb, A. (1981). Biochem. Biophys. Acta. 675: 62–68.
20. Ellouz, F., Adam, A., Ciorbaru, R. & Lederer, R., (1974). Biochem. Biophys. Res. Commun. 59: 1317–1325.
21. Reich, E. (1978). In *Molecular Basis of Biological Degradative Processes* (Berlin, R. D., Herman, L. L., Lepow, I. H. & Tranzer, J. M. Eds.) Academic Press, New York, p.155–159.
23. Holmberg, L., Lecander, I., Persson, B., Astedt, B. (1978). Biochem. Biophy. Acta. 544: 128–137.
24. Lowry, O. H., Rosebrough, N. J., Farr, A. L., Randall, R. J. (1951). J. Biol. Chem. 193: 265.
25. Bradford, M. M. (1976). Anal. Biochem. 72: 248–254.
26. Laemmlli, U. K. (1970). Nature 227, 680–685.
27. Merril, C. R., Goldman, D., Sedman, S. A., Ebert, M. H. (1981). Science 211: 1437.

28. Quinn, L. A., Moore, G. E., Morgan, R. T. and Woods, L. K. (1979). Cancer Res. 39: 4914–4924.
29. Rijken, D. C., Hoylaerts, M., Collen, D. (1982). J. Biol. Chem. 257: 2920–2925.
30. Camiolo, S. M., Markus, G., Evers, J. L., Hobika, G. H., De Pasquale, J. L., Beckley, S., Grimaldi, J. P. (1981). Int. J. Cancer 97: 191–198.
31. Corasanti, J. G., Celik, C., Camiolo, S. M., Mittelman, A., Evers, J. L., Barbasch, A., Hobika, G. H., Markus, G. (1980). J. Nat. Cancer Inst. 65: 345–351.
32. Evers, J. E., Patel, J., Madeja, J. M., Schneider, S. L., Hobika, G. H., Camiolo, S. M., Markus, G. (1982). Cancer Res. 42: 219–226.
33. Markus, G., Takita, H., Camiolo, S. M., Corasanti, J. G., Evers, J. L., Hobika, G. H. (1980). Cancer Res. 40: 841–848.
34. Camiolo, S. M., Markus, G., Englander, L. S., Siuta, M. R., HObika, G. H., Kohga, S. (1984). Cancer Res. 44: 311–318.
35. Marcus, G., Camiolo, S. M., Kohga, S., Madeja, J. M., Mittelman, A. (1983). Cancer Res. 43: 5517–5525.
36. Strassburger, W., Wollmer, A., Pitts, J. E., Glover, I. D., Tickle, I. J., Blundell, T. L., Steffens, G. J., Gunzler, W. A., Otting, F., Flohe, L. (1983). FEBS Letters 157: 219–223.
37. Kristensen, P., Larsson, L-I, Nielsen, L. S., Grondahl-Hansen, J., Andreasen, P. A., Dano, K. (1984). FEBS Letters 168: 33–37.
38. Duffy, M. J., O'Grady, P. (1984). Eur. J. Cancer Clin. Oncol. 20: 577–582.
39. Blumberg, P. M., Robbins, P. W. (1975). Cell 6: 137–147.
40. Sutherland, D. J. A. (1980). J.N.C.I. 64: 3–7
41. Ossowski, L., Quigley, J. P., Reich, E. (1975) in *Proteases and Biological Control* (Reich, E., Rifkin, D. B., Shaw, E. eds.) New York, Cold Spring Harbor Laboratory, p.901–913.
42. Day, E. D., Planinsek, J. A., Pressman, D. (1959). J.N.C.I. 22: 413–426.
43. O'Grady, R. L., Upfold, L. I., Stephens, R. W. (1981). Int. J. Cancer 28: 509–515.
44. Skriver, L., Larsson, L.-I., Kielberg, V., Nielsen, L. S., Andersen, P. B., Kristensen, P., Dano, K. (1984). J. of Cell Biol. 99: 752–757.
45. Taylor, C. R. (1978). Arch. Pathol. Lab. Med. 102: 113–121.
46. Soule, H. R., Linder E., Edgington, T. S. (1983). Proc. Natl.. Acad. Sci. 80: 1332–1336.
47. Ryman, B. E., Barratt, G. M., Begent, R. H. J. (1983). Biol. Cell 47: 71–80.
48. Richardson, V. J., Ryman, B. E., Jewkes, R. F., Jeyasingh, K., Tattersasll, M. H. N., Newlands, E. S., Kaye, S. B. (1979). B. J. Cancer 40: 35–43.
49. Osborne, M. P., Richardson, V. J., Jeyasingh, K., Ryman, B. E. (1982). Int. J. Nucl. Med. Biol. 9: 47–51.
50. Begent, RH. J., Keep, P. A., Green, A. J., Searle, F., Bagshawe, K. D., Jewkes, R. F., Jones, B. E., Barratt, G. M., Ryman, B. E. (1982). Lancet 739–742.

---

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 21 amino acids
        ( B ) TYPE: amino acid
        ( D ) TOPOLOGY: unknown ( i i ) MOLECULE TYPE: peptide ( v ) FRAGMENT TYPE: internal ( x i ) SEQUENCE DESCRIPTION: SEQ ID NO:1:

```
Ala Gln Ile Leu Glu Leu Pro Tyr Xaa Gly Asp Val Xaa Met Phe Leu
1               5                   10                  15

Leu Leu Pro Xaa Glu
            20
```

( 2 ) INFORMATION FOR SEQ ID NO:2:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( v ) FRAGMENT TYPE: internal ( x i ) SEQUENCE DESCRIPTION: SEQ ID NO:2:

```
Gly Arg Ala Asn Phe Ser Gly Met Ser Glu Xaa Asn Asp Leu Phe
1               5                   10                  15
```

(2) INFORMATION FOR SEQ ID NO:3:

(i) SEQUENCE CHARACTERISTICS:
        (A) LENGTH: 19 amino acids
        (B) TYPE: amino acid
        (D) TOPOLOGY: unknown (ii) MOLECULE TYPE: peptide (v) FRAGMENT TYPE: internal (xi) SEQUENCE DESCRIPTION: SEQ ID NO:3:

```
Met Ala Glu Xaa Glu Val Glu Val Tyr Ile Pro Gln Phe Lys Leu Glu
 1               5                  10                  15
Glu Xaa Tyr
```

(2) INFORMATION FOR SEQ ID NO:4:

(i) SEQUENCE CHARACTERISTICS:
        (A) LENGTH: 10 amino acids
        (B) TYPE: amino acid
        (D) TOPOLOGY: unknown (ii) MOLECULE TYPE: peptide (v) FRAGMENT TYPE: internal (xi) SEQUENCE DESCRIPTION: SEQ ID NO:4:

```
Leu Asn Ile Gly Tyr Ile Glu Asp Leu Lys
 1               5                  10
```

(2) INFORMATION FOR SEQ ID NO:5:

(i) SEQUENCE CHARACTERISTICS:
        (A) LENGTH: 10 amino acids
        (B) TYPE: amino acid
        (D) TOPOLOGY: unknown (ii) MOLECULE TYPE: peptide (v) FRAGMENT TYPE: internal (xi) SEQUENCE DESCRIPTION: SEQ ID NO:5:

```
Ile Pro Asn Leu Leu Pro Glu Gly Xaa Val
 1               5                  10
```

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Synthetic DNA oligonucleotide (iv) ANTI-SENSE: YES (ix) FEATURE:
        (A) NAME/KEY: modified_base
        (B) LOCATION: 12
        (D) OTHER INFORMATION: /mod_base=i (xi) SEQUENCE DESCRIPTION: SEQ ID NO:6:

TTRAAYTGNA CNATRTA                                17

(2) INFORMATION FOR SEQ ID NO:7:

(i) SEQUENCE CHARACTERISTICS:
        (A) LENGTH: 14 base pairs
        (B) TYPE: nucleic acid ( C ) STRANDEDNESS: single
( D ) TOPOLOGY: linear ( i i ) MOLECULE TYPE: Other nucleic acid;
( A ) DESCRIPTION: Synthetic DNA oligonucleotide ( i v ) ANTI-SENSE: YES ( x i ) SEQUENCE DESCRIPTION: SEQ ID NO:7:

TANACYTCNA CYTC 14

( 2 ) INFORMATION FOR SEQ ID NO:8:

( i ) SEQUENCE CHARACTERISTICS:
( A ) LENGTH: 14 base pairs
( B ) TYPE: nucleic acid
( C ) STRANDEDNESS: single
( D ) TOPOLOGY: linear ( i i ) MOLECULE TYPE: Other nucleic acid;
( A ) DESCRIPTION: Synthetic DNA oligonucleotide ( i v ) ANTI-SENSE: YES ( i x ) FEATURE:
( A ) NAME/KEY: modified_base
( B ) LOCATION: 6
( D ) OTHER INFORMATION: /mod_base=i ( x i ) SEQUENCE DESCRIPTION: SEQ ID NO:8:

TCBARNATNT GVGC 14

( 2 ) INFORMATION FOR SEQ ID NO:9:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: Other nucleic acid;
( A ) DESCRIPTION: Synthetic DNA olgonucleotide ( i v ) ANTI-SENSE: YES ( i x ) FEATURE:
( A ) NAME/KEY: modified_base
( B ) LOCATION: 9
( D ) OTHER INFORMATION: /mod_base=i ( i x ) FEATURE:
( A ) NAME/KEY: modified_base
( B ) LOCATION: 12
( D ) OTHER INFORMATION: /mod_base=i ( i x ) FEATURE:
( A ) NAME/KEY: modified_base
( B ) LOCATION: 18
( D ) OTHER INFORMATION: /mod_base=i ( i x ) FEATURE:
( A ) NAME/KEY: modified_base
( B ) LOCATION: 24
( D ) OTHER INFORMATION: /mod_base=i ( x i ) SEQUENCE DESCRIPTION: SEQ ID NO:9:

TTGAAYTGNA CNATGTANAC YTCNACYTC 29

( 2 ) INFORMATION FOR SEQ ID NO:10:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear (i i) MOLECULE TYPE: Other nucelic acid;
    (A) DESCRIPTION: Synthetic DNA oligonucleotide (i v) ANTI-SENSE: YES (i x) FEATURE:
    (A) NAME/KEY: modified_base
    (B) LOCATION: 6
    (D) OTHER INFORMATION: /mod_base=i (i x) FEATURE:
    (A) NAME/KEY: modified_base
    (B) LOCATION: 15
    (D) OTHER INFORMATION: /mod_base=i (x i) SEQUENCE DESCRIPTION: SEQ ID NO:10:

TCYTCNATRT ANCCNATRTT                                           20

(2) INFORMATION FOR SEQ ID NO:11:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (i i) MOLECULE TYPE: Other nucleic acid;
        (A) DESCRIPTION: Synthetic DNA oligonucleotide (i v) ANTI-SENSE: YES (i x) FEATURE:
        (A) NAME/KEY: modified_base
        (B) LOCATION: 3
        (D) OTHER INFORMATION: /mod_base=i (i x) FEATURE:
        (A) NAME/KEY: modified_base
        (B) LOCATION: 9
        (D) OTHER INFORMATION: /mod_base=i (x i) SEQUENCE DESCRIPTION: SEQ ID NO:11:

AANTTNGCNC KNCC                                                 14

(2) INFORMATION FOR SEQ ID NO:12:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (i i) MOLECULE TYPE: Other nucleic acid;
        (A) DESCRIPTION: Synthetic DNA oligonucleotide (i v) ANTI-SENSE: YES (x i) SEQUENCE DESCRIPTION: SEQ ID NO:12:

ATATGTTTCC TCGAGCTTGA ACTGAGGGAT GTACACCTCG ACTTCGCTCT CTGCCAT       57

(2) INFORMATION FOR SEQ ID NO:13:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (i i) MOLECULE TYPE: Other nucleic acid;
        (A) DESCRIPTION: Synthetic DNA oligonucleotide (i v) ANTI-SENSE: YES (x i) SEQUENCE DESCRIPTION: SEQ ID NO:13:

TTCATCAGGC AACAGGAGGA ACATGCTCAC ATCTCCGGCG TAAGGGAGTT CCAGGATCTT    60

CATTTT 66

( 2 ) INFORMATION FOR SEQ ID NO:14:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( i v ) ANTI-SENSE: YES ( x i ) SEQUENCE DESCRIPTION: SEQ ID NO:14:

CTCCTCCAGC TTGAACTGGG GGATGTAGAC CTCCACCTC 39

( 2 ) INFORMATION FOR SEQ ID NO:15:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( i v ) ANTI-SENSE: YES ( x i ) SEQUENCE DESCRIPTION: SEQ ID NO:15:

CTTGAACTGR GGRATGTASA CCTCCACCTC 30

( 2 ) INFORMATION FOR SEQ ID NO:16:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( i v ) ANTI-SENSE: YES ( x i ) SEQUENCE DESCRIPTION: SEQ ID NO:16:

TTCCAGTAAA TAATTCCCTG TGGATGCATT 30

( 2 ) INFORMATION FOR SEQ ID NO:17:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( i v ) ANTI-SENSE: YES ( x i ) SEQUENCE DESCRIPTION: SEQ ID NO:17:

GCCTGCAAAA TCGCATCAGG ATAACTACC 29

( 2 ) INFORMATION FOR SEQ ID NO:18:

( i ) SEQUENCE CHARACTERISTICS:
        ( A ) LENGTH: 2409 base pairs
        ( B ) TYPE: nucleic acid
        ( C ) STRANDEDNESS: double 5,422,090

69 70

-continued ( D ) TOPOLOGY: unknown ( i i ) MOLECULE TYPE: cDNA to genomic RNA ( i x ) FEATURE:
    ( A ) NAME/KEY: CDS
    ( B ) LOCATION: 49..1296

( x i ) SEQUENCE DESCRIPTION: SEQ ID NO:18:

```
GTCAGACAGC AACTCAGAGA ATAACCAGAG AACAACCAGA TTGAAACA ATG GAG GAT        57
                                                        Met Glu Asp
                                                         1

CTT TGT GTG GCA AAC ACA CTC TTT GCC CTC AAT TTA TTC AAG CAT CTG        105
Leu Cys Val Ala Asn Thr Leu Phe Ala Leu Asn Leu Phe Lys His Leu
     5                  10                  15

GCA AAA GCA AGC CCC ACC CAG AAC CTC TTC CTC TCC CCA TGG AGC ATC        153
Ala Lys Ala Ser Pro Thr Gln Asn Leu Phe Leu Ser Pro Trp Ser Ile
 20              25                  30                  35

TCG TCC ACC ATG GCC ATG GTC TAC ATG GGC TCC AGG GGC AGC ACC GAA        201
Ser Ser Thr Met Ala Met Val Tyr Met Gly Ser Arg Gly Ser Thr Glu
                 40                  45                  50

GAC CAG ATG GCC AAG GTG CTT CAG TTT AAT GAA GTG GGA GCC AAT GCA        249
Asp Gln Met Ala Lys Val Leu Gln Phe Asn Glu Val Gly Ala Asn Ala
             55                  60                  65

GTT ACC CCC ATG ACT CCA GAG AAC TTT ACC AGC TGT GGG TTC ATG CAG        297
Val Thr Pro Met Thr Pro Glu Asn Phe Thr Ser Cys Gly Phe Met Gln
         70                  75                  80

CAG ATC CAG AAG GGT AGT TAT CCT GAT GCG ATT TTG CAG GCA CAA GCT        345
Gln Ile Gln Lys Gly Ser Tyr Pro Asp Ala Ile Leu Gln Ala Gln Ala
     85                  90                  95

GCA GAT AAA ATC CAT TCA TCC TTC CGC TCT CTC AGC TCT GCA ATC AAT        393
Ala Asp Lys Ile His Ser Ser Phe Arg Ser Leu Ser Ser Ala Ile Asn
100                 105                 110                 115

GCA TCC ACA GGG AAT TAT TTA CTG GAA AGT GTC AAT AAG CTG TTT GGT        441
Ala Ser Thr Gly Asn Tyr Leu Leu Glu Ser Val Asn Lys Leu Phe Gly
                 120                 125                 130

GAG AAG TCT GCG AGC TTC CGG GAA GAA TAT ATT CGA CTC TGT CAG AAA        489
Glu Lys Ser Ala Ser Phe Arg Glu Glu Tyr Ile Arg Leu Cys Gln Lys
             135                 140                 145

TAT TAC TCC TCA GAA CCC CAG GCA GTA GAC TTC CTA GAA TGT GCA GAA        537
Tyr Tyr Ser Ser Glu Pro Gln Ala Val Asp Phe Leu Glu Cys Ala Glu
         150                 155                 160

GAA GCT AGA AAA AAG ATT AAT TCC TGG GTC AAG ACT CAA ACC AAA GGC        585
Glu Ala Arg Lys Lys Ile Asn Ser Trp Val Lys Thr Gln Thr Lys Gly
165                 170                 175

AAA ATC CCA AAC TTG TTA CCT GAA GGT TCT GTA GAT GGG GAT ACC AGG        633
Lys Ile Pro Asn Leu Leu Pro Glu Gly Ser Val Asp Gly Asp Thr Arg
180                 185                 190                 195

ATG GTC CTG GTG AAT GCT GTC TAC TTC AAA GGA AAG TGG AAA ACT CCA        681
Met Val Leu Val Asn Ala Val Tyr Phe Lys Gly Lys Trp Lys Thr Pro
                 200                 205                 210

TTT GAG AAG AAA CTA AAT GGG CTT TAT CCT TTC CGT GTA AAC TCG GCT        729
Phe Glu Lys Lys Leu Asn Gly Leu Tyr Pro Phe Arg Val Asn Ser Ala
             215                 220                 225

CAG CGC ACA CCT GTA CAG ATG ATG TAC TTG CGT GAA AAG CTA AAC ATT        777
Gln Arg Thr Pro Val Gln Met Met Tyr Leu Arg Glu Lys Leu Asn Ile
         230                 235                 240

GGA TAC ATA GAA GAC CTA AAG GCT CAG ATT CTA GAA CTC CCA TAT GCT        825
Gly Tyr Ile Glu Asp Leu Lys Ala Gln Ile Leu Glu Leu Pro Tyr Ala
245                 250                 255

GGA GAT GTT AGC ATG TTC TTG TTG CTT CCA GAT GAA ATT GCC GAT GTG        873
Gly Asp Val Ser Met Phe Leu Leu Leu Pro Asp Glu Ile Ala Asp Val
260                 265                 270                 275
```

| | |
|---|---|
| TCC ACT GGC TTG GAG CTG CTG GAA AGT GAA ATA ACC TAT GAC AAA CTC<br>Ser Thr Gly Leu Glu Leu Leu Glu Ser Glu Ile Thr Tyr Asp Lys Leu<br>280                    285                      290 | 921 |
| AAC AAG TGG ACC AGC AAA GAC AAA ATG GCT GAA GAT GAA GTT GAG GTA<br>Asn Lys Trp Thr Ser Lys Asp Lys Met Ala Glu Asp Glu Val Glu Val<br>          295                      300                      305 | 969 |
| TAC ATA CCC CAG TTC AAA TTA GAA GAG CAT TAT GAA CTC AGA TCC ATT<br>Tyr Ile Pro Gln Phe Lys Leu Glu Glu His Tyr Glu Leu Arg Ser Ile<br>          310                      315                      320 | 1017 |
| CTG AGA AGC ATG GGC ATG GAG GAC GCC TTC AAC AAG GGA CGG GCC AAT<br>Leu Arg Ser Met Gly Met Glu Asp Ala Phe Asn Lys Gly Arg Ala Asn<br>325                    330                      335 | 1065 |
| TTC TCA GGG ATG TCG GAG AGG AAT GAC CTG TTT CTT TCT GAA GTG TTC<br>Phe Ser Gly Met Ser Glu Arg Asn Asp Leu Phe Leu Ser Glu Val Phe<br>340                    345                      350                      355 | 1113 |
| CAC CAA GCC ATG GTG GAT GTG AAT GAG GAG GGC ACT GAA GCA GCC GCT<br>His Gln Ala Met Val Asp Val Asn Glu Glu Gly Thr Glu Ala Ala Ala<br>                    360                      365                      370 | 1161 |
| GGC ACA GGA GGT GTT ATG ACA GGG AGA ACT GGA CAT GGA GGC CCA CAG<br>Gly Thr Gly Gly Val Met Thr Gly Arg Thr Gly His Gly Gly Pro Gln<br>                    375                      380                      385 | 1209 |
| TTT GTG GCA GAT CAT CCT TTT CTT TTT CTT ATT ATG CAT AAG ATA ACC<br>Phe Val Ala Asp His Pro Phe Leu Phe Leu Ile Met His Lys Ile Thr<br>          390                      395                      400 | 1257 |
| AAC TGC ATT TTA TTT TTC GGC AGA TTT TCC TCA CCC TAAAACTAAG<br>Asn Cys Ile Leu Phe Phe Gly Arg Phe Ser Ser Pro<br>405                    410                      415 | 1303 |
| CGTGCTGCTT CTGCAAAAGA TTTTTGTAGA TGAGCTGTGT GCCTCAGAAT TGCTATTTCA | 1363 |
| AATTGCCAAA AATTTAGAGA TGTTTTCTAC ATATTTCTGC TCTTCTGAAC AACTTCTGCT | 1423 |
| ACCCACTAAA TAAAAACACA GAAATAATTA GACAATTGTC TATTATAACA TGACAACCCT | 1483 |
| ATTAATCATT TGGTCTTCTA AAATGGGATC ATGCCCATTT AGATTTTCCT TACTATCAGT | 1543 |
| TTATTTTTAT AACATTAACT TTTACTTTGT TATTTATTAT TTTATATAAT GGTGAGTTTT | 1603 |
| TAAATTATTG CTCACTGCCT ATTTAATGTA GCTAATAAAG TTATAGAAGC AGATGATCTG | 1663 |
| TTAATTTCCT ATCTAATAAA TGCCTTTAAT TGTTCTCATA ATGAAGAATA AGTAGGTATC | 1723 |
| CCTCCATGCC CTTCTGTAAT AAATATCTGG AAAAAACATT AAACAATAGG CAAATATATG | 1783 |
| TTATGTGCAT TTCTAGAAAT ACATAACACA TATATATGTC TGTATCTTAT ATTCAATTGC | 1843 |
| AAGTATATAA TGTCATAATT TCAAGACCAG CCTGGCCAAC ATAGCGAAAC CCTACCTCCA | 1903 |
| CTAAAAATAC AGAAATGAGC CGGGAGTGGT GGCAAAGTGG TGAGCACCTG TGATCCCAGC | 1963 |
| CACTGTGGAG GCCGAGGCAG GACAATCACT TGAACCCAGG AGGCGGAGGC TGCAGTGAGC | 2023 |
| TGAGATCGCT CCACTGCACT CCAGCCTGGG CAACAGAGCA GATTCCATC TCAAAATACA | 2083 |
| TTAAAAAAAA AAACCTATCT GAGGACTCTG AAAAGTAAAT GGTAGCAGAT AGATTTGAGA | 2143 |
| AGGGAACTAG AACTTGAAGC ACAATCTATC TGGTGCTCTT TCTTACTTTT GCTTGTTTTC | 2203 |
| TCCCAATCTT CCAGTCTGGA TACAAAGGCA GCCCAATTTC TAGAAATGTA TACCAGCCAT | 2263 |
| GAAGAGATAA AGCTCCAAGA GGAGATTTCT CTTTCTGGTA TAAGGTATGT GTGTGTATAT | 2323 |
| GGGGGGCGAT AAGGTTGGGA GTGTGAGGAA TACAGAGTCG GAGAAATCCA TTATTTCCAC | 2383 |
| CCTCTCTCTT GCCATTGCAA CCAGAC | 2409 |

( 2 ) INFORMATION FOR SEQ ID NO:19:

( i ) SEQUENCE CHARACTERISTICS:
        ( A ) LENGTH: 415 amino acids
        ( B ) TYPE: amino acid
        ( D ) TOPOLOGY: linear ( i i ) MOLECULE TYPE: protein ( x i ) SEQUENCE DESCRIPTION: SEQ ID NO:19:

| Met | Glu | Asp | Leu | Cys | Val | Ala | Asn | Thr | Leu | Phe | Ala | Leu | Asn | Leu | Phe |
|---|---|---|---|---|---|---|---|---|---|---|---|---|---|---|---|
| 1 | | | | 5 | | | | | 10 | | | | | 15 | |
| Lys | His | Leu | Ala | Lys | Ala | Ser | Pro | Thr | Gln | Asn | Leu | Phe | Leu | Ser | Pro |
| | | | 20 | | | | | 25 | | | | | 30 | | |
| Trp | Ser | Ile | Ser | Ser | Thr | Met | Ala | Met | Val | Tyr | Met | Gly | Ser | Arg | Gly |
| | | | 35 | | | | 40 | | | | | 45 | | | |
| Ser | Thr | Glu | Asp | Gln | Met | Ala | Lys | Val | Leu | Gln | Phe | Asn | Glu | Val | Gly |
| | 50 | | | | | 55 | | | | | 60 | | | | |
| Ala | Asn | Ala | Val | Thr | Pro | Met | Thr | Pro | Glu | Asn | Phe | Thr | Ser | Cys | Gly |
| 65 | | | | | 70 | | | | 75 | | | | | | 80 |
| Phe | Met | Gln | Gln | Ile | Gln | Lys | Gly | Ser | Tyr | Pro | Asp | Ala | Ile | Leu | Gln |
| | | | | 85 | | | | | 90 | | | | | 95 | |
| Ala | Gln | Ala | Ala | Asp | Lys | Ile | His | Ser | Ser | Phe | Arg | Ser | Leu | Ser | Ser |
| | | | 100 | | | | | 105 | | | | | 110 | | |
| Ala | Ile | Asn | Ala | Ser | Thr | Gly | Asn | Tyr | Leu | Leu | Glu | Ser | Val | Asn | Lys |
| | | | 115 | | | | | 120 | | | | | 125 | | |
| Leu | Phe | Gly | Glu | Lys | Ser | Ala | Ser | Phe | Arg | Glu | Glu | Tyr | Ile | Arg | Leu |
| | | 130 | | | | | 135 | | | | | 140 | | | |
| Cys | Gln | Lys | Tyr | Tyr | Ser | Ser | Glu | Pro | Gln | Ala | Val | Asp | Phe | Leu | Glu |
| 145 | | | | | 150 | | | | | 155 | | | | | 160 |
| Cys | Ala | Glu | Glu | Ala | Arg | Lys | Lys | Ile | Asn | Ser | Trp | Val | Lys | Thr | Gln |
| | | | | 165 | | | | | 170 | | | | | 175 | |
| Thr | Lys | Gly | Lys | Ile | Pro | Asn | Leu | Leu | Pro | Glu | Gly | Ser | Val | Asp | Gly |
| | | | 180 | | | | | 185 | | | | | 190 | | |
| Asp | Thr | Arg | Met | Val | Leu | Val | Asn | Ala | Val | Tyr | Phe | Lys | Gly | Lys | Trp |
| | | 195 | | | | | 200 | | | | | 205 | | | |
| Lys | Thr | Pro | Phe | Glu | Lys | Lys | Leu | Asn | Gly | Leu | Tyr | Pro | Phe | Arg | Val |
| 210 | | | | | | 215 | | | | | 220 | | | | |
| Asn | Ser | Ala | Gln | Arg | Thr | Pro | Val | Gln | Met | Met | Tyr | Leu | Arg | Glu | Lys |
| 225 | | | | | 230 | | | | | 235 | | | | | 240 |
| Leu | Asn | Ile | Gly | Tyr | Ile | Glu | Asp | Leu | Lys | Ala | Gln | Ile | Leu | Glu | Leu |
| | | | | 245 | | | | | 250 | | | | | 255 | |
| Pro | Tyr | Ala | Gly | Asp | Val | Ser | Met | Phe | Leu | Leu | Leu | Pro | Asp | Glu | Ile |
| | | | 260 | | | | | 265 | | | | | 270 | | |
| Ala | Asp | Val | Ser | Thr | Gly | Leu | Glu | Leu | Leu | Glu | Ser | Glu | Ile | Thr | Tyr |
| | | 275 | | | | | 280 | | | | | 285 | | | |
| Asp | Lys | Leu | Asn | Lys | Trp | Thr | Ser | Lys | Asp | Lys | Met | Ala | Glu | Asp | Glu |
| | 290 | | | | | 295 | | | | | 300 | | | | |
| Val | Glu | Val | Tyr | Ile | Pro | Gln | Phe | Lys | Leu | Glu | Glu | His | Tyr | Glu | Leu |
| 305 | | | | | 310 | | | | | 315 | | | | | 320 |
| Arg | Ser | Ile | Leu | Arg | Ser | Met | Gly | Met | Glu | Asp | Ala | Phe | Asn | Lys | Gly |
| | | | | 325 | | | | | 330 | | | | | 335 | |
| Arg | Ala | Asn | Phe | Ser | Gly | Met | Ser | Glu | Arg | Asn | Asp | Leu | Phe | Leu | Ser |
| | | | 340 | | | | | 345 | | | | | 350 | | |
| Glu | Val | Phe | His | Gln | Ala | Met | Val | Asp | Val | Asn | Glu | Glu | Gly | Thr | Glu |
| | | | 355 | | | | | 360 | | | | | 365 | | |
| Ala | Ala | Ala | Gly | Thr | Gly | Gly | Val | Met | Thr | Gly | Arg | Thr | Gly | His | Gly |
| | | 370 | | | | | 375 | | | | | 380 | | | |
| Gly | Pro | Gln | Phe | Val | Ala | Asp | His | Pro | Phe | Leu | Phe | Leu | Ile | Met | His |
| 385 | | | | | 390 | | | | | 395 | | | | | | 400 |
| Lys | Ile | Thr | Asn | Cys | Ile | Leu | Phe | Phe | Gly | Arg | Phe | Ser | Ser | Pro | |
| | | | | 405 | | | | | 410 | | | | | 415 | |

We claim:

1. Isolated human PAI-2 having an apparent molecular size of 60–70,000 by gel filtration, identical to the serum albumin standard, characterized by its specific inhibition of urokinase-type plasminogen activator and by being heat labile at temperatures above 56° C., stable to freezing at −20° C. and thawing, and stable in the pH range of 5 to 9 at 4° C.

2. PAI-2 defined by claim 1 further characterized by its formation of a detergent resistent complex with urokinase or urokinase-type plasminogen activator.

3. A reagent for locating and defining the boundaries of tumours in histological specimens or in vitro comprising suitably labelled human PAI-2.

4. A reagent according to claim 3 wherein said PAI-2 is labelled with a radioactive isotope.

5. A reagent according to claim 3 wherein said PAI-2 is labelled with fluorescein.

6. A composition of matter comprising purified human PAI-2, which:
   a) specifically inhibits human urokinase-type plasminogen activator but not tissue-type plasminogen activator in the presence of fibrin;
   b) is heat labile at temperatures above 56° C.;
   c) is stable to freezing at −20° and thawing;
   d) is stable in a pH range of 5 to 9 at 4° C.;
   e) has a pI between 5.0 and 5.6;
   f) forms a detergent resistant complex with human urokinase or human urokinase-type plasminogen activator; and,
   g) produces at least one band with a $M_r$ of 32 kD, 39–48 kD, or 60 kD on non-reducing SDS-PAGE, wherein said at least one band disappears when said PAI-2 is incubated with urokinase.

7. A reagent for locating and defining the boundaries of tumours in histological specimens in vitro, said reagent comprising purified human PAI-2 in suitably labelled form.

8. The reagent as defined by claim 7, wherein said PAI-2 is labelled with a radioactive isotope.

9. The reagent as defined by claim 7, wherein said PAI-2 is labelled with fluorescein.

10. Human PAI-2, purified to homogeneity, comprising the amino acid sequence illustrated in FIG. 56 (SEQ ID NO:19).

11. An isolated polypeptide having an amino acid sequence comprising a part of the amino acid sequence illustrated in FIG. 56 (SEQ ID NO:19), wherein said part is an antigen or biologically active amino acid sequence of human PAI-2.

12. The polypeptide as defined by claim 11, having substantially the biological activity of said PAI-2.

13. The polypeptide as defined by claim 11, wherein said polypeptide acts as an immunogen for producing antibodies to said PAI-2 in an appropriate host.

14. The polypeptide as defined by claim 11, prepared by a method comprising the steps of:
   a) purifying human PAI-2 to homogeneity, whereby purified human PAI-2 is obtained;
   b) fragmenting said purified PAI-2, whereby polypeptides comprising parts of PAI-2 are produced; and
   c) isolating a polypeptide, from said polypeptides comprising an antigen or biologically active amino acid sequence of human PAI-2.

15. The polypeptide as defined by claim 14, wherein fragmenting of said purified PAI-2 is achieved by digesting said purified PAI-2 with endoproteinase LysC to produce said polypeptides, and further wherein said polypeptides having amino acid sequences unique to human PAI-2 are isolated by reverse phase high pressure liquid chromatography.

16. Substantially pure human plasminogen activator inhibitor that
   (a) inhibits human urokinase-type plasminogen activator but not tissue-type plasminogen activator in the presence of fibrin; and
   (b) consists of a substantially pure protein selected from the group consisting of protein with a $M_r$ of 32 kD, 39–48 kD and 60 Kd, respectively, as determined by electrophoretic mobility on non-reducing SDS-PAGE, wherein said substantially pure protein, upon inhibiting a human urokinase-type plasminogen activator, forms a detergent-resistant complex with said human urokinase-type plasminogen activator.

17. Substantially pure PAI-2 having the amino acid sequence illustrated in FIG. 56 (SEQ. ID. NO:19).

18. A human polypeptide purified to homogeneity, said polypeptide comprising at least one amino acid sequence of human PAI-2 selected from the group of sequences consisting of:

Ala Gln Ile Leu Glu Leu Pro Tyr—Gly Asp Val—Met Phe
Leu Leu Leu Pro—Glu; Gly Arg Ala Asn Phe Ser Gly
Met Ser Glu—Asn Asp Leu Phe; Met Ala Glu—Glu
Val Glu Val Tyr Ile Pro Gln Phe Lys Leu Glu Glu—Tyr;
Leu Asn Ile Gly Tyr Ile Glu Asp Leu Lys; and Ile
Pro Asn Leu Leu Pro Glu Gly—Val, wherein a hyphen in a sequence represents an indeterminate residue (SEQ.ID.NOS:1–5).

19. Substantially pure human PAI-2 having the following amino acid sequence:

| Met | Glu | Asp | Leu | Cys | Val | Ala | Asn | Thr | Leu |
|---|---|---|---|---|---|---|---|---|---|
| Phe | Ala | Leu | Asn | Leu | Phe | Lys | His | Leu | Ala |
| Lys | Ala | Ser | Pro | Thr | Gln | Asn | Leu | Phe | Leu |
| Ser | Pro | Trp | Ser | Ile | Ser | Ser | Thr | Met | Ala |
| Met | Val | Tyr | Met | Gly | Ser | Arg | Gly | Ser | Thr |
| Glu | Asp | Gln | Met | Ala | Lys | Val | Leu | Glu | Phe |
| Asn | Glu | Val | Gly | Ala | Asn | Ala | Val | Thr | Pro |
| Met | Thr | Pro | Glu | Asn | Phe | Thr | Ser | Cys | Gly |
| Phe | Met | Gln | Gln | Ile | Gln | Lys | Gly | Ser | Tyr |
| Pro | Asp | Ala | Ile | Leu | Gln | Ala | Gln | Ala | Ala |
| Asp | Lys | Ile | His | Ser | Ser | Phe | Arg | Ser | Leu |
| Ser | Ser | Ala | Ile | Asn | Ala | Ser | Thr | Gly | Asn |
| Tyr | Leu | Leu | Glu | Ser | Val | Asn | Lys | Leu | Phe |
| Gly | Glu | Lys | Ser | Ala | Ser | Phe | Arg | Glu | Glu |
| Tyr | Ile | Arg | Leu | Cys | Gln | Lys | Tyr | Tyr | Ser |
| Ser | Glu | Pro | Gln | Ala | Val | Asp | Phe | Leu | Glu |
| Cys | Ala | Glu | Glu | Ala | Arg | Lys | Lys | Ile | Asn |
| Ser | Trp | Val | Lys | Thr | Gln | Thr | Lys | Gly | Lys |
| Ile | Pro | Asn | Leu | Leu | Pro | Glu | Gly | Ser | Val |
| Asp | Gly | Asp | Thr | Arg | Met | Val | Leu | Val | Asn |
| Ala | Val | Tyr | Phe | Lys | Gly | Lys | Trp | Lys | Thr |
| Pro | Phe | Glu | Lys | Lys | Leu | Asn | Gly | Leu | Tyr |
| Pro | Phe | Arg | Val | Asn | Ser | Ala | Gln | Arg | Thr |
| Pro | Val | Gln | Met | Met | Tyr | Leu | Arg | Glu | Lys |
| Leu | Asn | Ile | Gly | Tyr | Ile | Glu | Asp | Leu | Lys |
| Ala | Gln | Ile | Leu | Glu | Leu | Pro | Tyr | Ala | Gly |

-continued

| Asp | Val | Ser | Met | Phe | Leu | Leu | Leu | Pro | Asp |
| Glu | Ill | Ala | Asp | Val | Ser | Thr | Gly | Leu | Glu |
| Leu | Leu | Glu | Ser | Glu | Ile | Thr | Tyr | Asp | Lys |
| Leu | Asn | Lys | Trp | Thr | Ser | Lys | Asp | Lys | Met |
| Ala | Glu | Asp | Glu | Val | Glu | Val | Tyr | Ile | Pro |
| Gln | Phe | Lys | Leu | Glu | Glu | His | Tyr | Glu | Leu |
| Arg | Ser | Ile | Leu | Arg | Ser | Met | Gly | Met | Glu |
| Asp | Ala | Phe | Asn | Lys | Gly | Arg | Ala | Asn | Phe |
| Ser | Gly | Met | Ser | Glu | Arg | Asn | Asp | Leu | Phe |
| Leu | Ser | Glu | Val | Phe | His | Gln | Ala | Met | Val |

-continued

| Asp | Val | Asn | Glu | Glu | Gly | Thr | Glu | Ala | Ala |
| Ala | Gly | Thr | Gly | Gly | Val | Met | Thr | Gly | Arg |
| Thr | Gly | His | Gly | Gly | Pro | Gln | Phe | Val | Ala |
| Asp | His | Pro | Phe | Leu | Phe | Leu | Ile | Met | His |
| Lys | Ile | Thr | Asn | Cys | Ile | Leu | Phe | Phe | Gly |
| Arg | Phe | Ser | Ser | Pro(SEQ. ID. NO: 19). | | | | | |

20. A reagent for locating or defining the boundaries of tumors in histological specimens or in vivo, said reagent comprising human PAI-2 as defined by claim 19 in association with a suitable label.

* * * * *